US012685725B2

(12) United States Patent (10) Patent No.: US 12,685,725 B2
Hayden et al. (45) **Date of Patent: *Jul. 21, 2026**

(54) PRIDOPIDINE FOR THE TREATMENT OF MITOCHONDRIAL-ASSOCIATED DISEASES AND DISORDERS AND ENDOPLASMIC RETICULUM (ER) STRESS

(71) Applicant: PRILENIA NEUROTHERAPEUTICS LTD., Herzliya (IL)

(72) Inventors: Michael Hayden, Herzliya (IL); Michal Geva, Even-Yehuda (IL); Ana Cristina Carvalho Rego, Coimbra (PT); Gerardo Lederkremer, Shoham (PT)

(73) Assignee: PRILENIA NEUROTHERAPEUTICS LTD., Yakum (IL)

( * ) Notice: Subject to any disclaimer, the term of this patent is extended or adjusted under 35 U.S.C. 154(b) by 777 days.

This patent is subject to a terminal disclaimer.

(21) Appl. No.: 17/182,605

(22) Filed: Feb. 23, 2021

(65) Prior Publication Data

US 2021/0220342 A1 Jul. 22, 2021

Related U.S. Application Data

(63) Continuation-in-part of application No. PCT/IL2020/050308, filed on Mar. 15, 2020.

(60) Provisional application No. 62/818,796, filed on Mar. 15, 2019.

(51) Int. Cl.
*A61K 31/44* (2006.01)
*A61P 25/28* (2006.01)

(52) U.S. Cl.
CPC .............. *A61K 31/44* (2013.01); *A61P 25/28* (2018.01)

(58) Field of Classification Search
CPC ................................. A61K 31/44; A61P 25/28
See application file for complete search history.

(56) References Cited

U.S. PATENT DOCUMENTS

| | | | |
|---|---|---|---|
| 6,903,120 | B2 | 6/2005 | Sonesson |
| 7,417,043 | B2 | 8/2008 | Sonesson |
| 7,923,459 | B2 | 4/2011 | Gauthier et al. |
| 9,006,445 | B2 | 4/2015 | Sonesson et al. |
| 9,012,476 | B2 | 4/2015 | Zimmermann et al. |
| 9,139,525 | B2 | 9/2015 | Wikstrom |
| RE46,117 | E | 8/2016 | Sonesson et al. |
| 9,796,673 | B2 | 10/2017 | Wu et al. |
| 9,814,706 | B2 | 11/2017 | Zimmermann et al. |
| 10,047,049 | B2 | 8/2018 | Barel et al. |
| 10,130,621 | B2 | 11/2018 | Schmidt |
| 10,322,119 | B2 | 6/2019 | Bassan |
| 10,406,145 | B2 | 9/2019 | Schmidt |
| 2013/0197031 | A1 | 8/2013 | Sonesson |
| 2013/0267552 | A1 | 10/2013 | Waters |

| | | | | |
|---|---|---|---|---|
| 2014/0024677 | A1* | 1/2014 | Schnellmann | ....... A61K 31/138 |
| | | | | 514/312 |
| 2014/0088145 | A1* | 3/2014 | Hayden | ................ A61K 31/451 |
| | | | | 514/317 |
| 2015/0202302 | A1 | 7/2015 | Licht | |
| 2015/0374677 | A1* | 12/2015 | Schmidt | ................. G01N 30/88 |
| | | | | 546/217 |
| 2016/0095847 | A1 | 4/2016 | Sonesson | |
| 2016/0166559 | A1 | 6/2016 | Sonesson | |
| 2016/0243098 | A1 | 8/2016 | Geva et al. | |
| 2017/0020854 | A1* | 1/2017 | Licht | ........................ A61K 9/28 |
| 2017/0266170 | A1 | 9/2017 | Waters | |
| 2018/0055832 | A1 | 3/2018 | Hayden | |
| 2018/0235950 | A1 | 8/2018 | Sonesson | |
| 2019/0015401 | A1 | 1/2019 | Sonesson | |
| 2019/0046516 | A1 | 2/2019 | Russ | |
| 2019/0192496 | A1 | 6/2019 | Borowsky | |
| 2019/0209542 | A1 | 7/2019 | Bassan | |
| 2019/0231768 | A1 | 8/2019 | Geva | |
| 2019/0336488 | A1 | 11/2019 | Hayden | |
| 2019/0350914 | A1 | 11/2019 | Geva | |
| 2019/0350915 | A1 | 11/2019 | Bassan | |

FOREIGN PATENT DOCUMENTS

| | | |
|---|---|---|
| WO | WO 2001/046145 | 6/2001 |
| WO | WO 2006/040155 | 4/2006 |
| WO | WO 2008/127188 | 10/2008 |
| WO | WO 2012/002863 | 3/2012 |
| WO | WO 2013/034622 | 3/2013 |
| WO | WO 2013/086425 | 6/2013 |
| WO | WO 2013/152105 | 10/2013 |
| WO | WO 2014/205229 | 12/2014 |
| WO | WO 2015/112601 | 7/2015 |
| WO | WO 2016/003919 | 1/2016 |

(Continued)

OTHER PUBLICATIONS

Yannai et. al. (BioRxiv (Jan. 19, 2019) 1-23). (Year: 2019).*
Al-Saif, A. et al. (2011). A mutation in sigma-1 receptor causes juvenile amyotrophic lateral sclerosis. Annals of neurology, 70(6), 913-919.
Area-Gomez, E. et al. (2012). Upregulated function of mitochondria-associated ER membranes in Alzheimer disease. The EMBO journal, 31(21), 4106-4123.
Avezov, E. et al. (2008). Endoplasmic reticulum (ER) mannosidase I is compartmentalized and required for N-glycan trimming to Man5-6GlcNAc2 in glycoprotein ER-associated degradation. Molecular biology of the cell, 19(1), 216-225.

(Continued)

*Primary Examiner* — Marcos L Sznaidman
(74) *Attorney, Agent, or Firm* — Mark S. Cohen; PEARL COHEN LLP

(57) ABSTRACT

The subject invention provides a method for treating a subject afflicted with a disease, disorder, or condition associated with mitochondrial dysfunction or ER stress, comprising administering to the subject a composition comprising pridopidine or a pharmaceutically acceptable salt thereof.

6 Claims, 37 Drawing Sheets
(6 of 37 Drawing Sheet(s) Filed in Color)
Specification includes a Sequence Listing.

(56) References Cited

FOREIGN PATENT DOCUMENTS

| WO | WO 2016/138130 | | 9/2016 |
|----|----------------|---|--------|
| WO | WO 2016/138135 | | 9/2016 |
| WO | WO 2017/015609 | | 1/2017 |
| WO | WO 2017/015615 | | 1/2017 |
| WO | WO 2017/147366 | * | 8/2017 |
| WO | WO 2018/039475 | | 3/2018 |
| WO | WO 2018/039477 | | 3/2018 |
| WO | WO 2018/053275 | | 3/2018 |
| WO | WO 2018/053280 | | 3/2018 |
| WO | WO 2018/053287 | | 3/2018 |
| WO | WO 2018/136600 | | 7/2018 |
| WO | WO 2018/200323 | | 11/2018 |
| WO | WO 2018/207192 | | 11/2018 |
| WO | WO 2019/036358 | | 2/2019 |
| WO | WO 2019/046568 | | 3/2019 |
| WO | WO 2019/050775 | | 3/2019 |

OTHER PUBLICATIONS

Basso, V. et al. (2018). Regulation of ER-mitochondria contacts by Parkin via Mfn2. Pharmacological research, 138, 43-56.

Benyair, R. et al. (2015, May). Glycan regulation of ER-associated degradation through compartmentalization. In Seminars in cell & developmental biology (vol. 41, pp. 99-109). Academic Press.

Berge, S. M. et al. (1977). Pharmaceutical salts. Journal of pharmaceutical sciences, 66(1), 1-19.

Bernard-Marissal, N. et al. (2015). Dysfunction in endoplasmic reticulum-mitochondria crosstalk underlies SIGMAR1 loss of function mediated motor neuron degeneration. Brain, 138(4), 875-890.

Bernard-Marissal, N. et al. (2019). Altered interplay between endoplasmic reticulum and mitochondria in Charcot-Marie-Tooth type 2A neuropathy. Proceedings of the National Academy of Sciences, 116(6), 2328-2337.

Bolshakova, A. V. et al. (2017). Neuroprotective effect of σ1-receptors on the cell model of Huntington's disease. Bulletin of experimental biology and medicine, 164(2), 252-258.

Branco-Santos, J. et al. (2017). Protein phosphatase 1 regulates huntingtin exon 1 aggregation and toxicity. Human molecular genetics, 26(19), 3763-3775.

Brimson, J. M. et al. (2020). Using Sigma-ligands as part of a multi-receptor approach to target diseases of the brain. Expert Opinion on Therapeutic Targets, 24(10), 1009-1028.

Carnemolla, A. et al. (2009). Rrs1 is involved in endoplasmic reticulum stress response in Huntington disease. Journal of Biological Chemistry, 284(27), 18167-18173.

Caron, N. S. et al. (2018). Therapeutic approaches to Huntington disease: from the bench to the clinic. Nature Reviews Drug Discovery, 17(10), 729-750.

Carri, A. D. et al. (2013). Human pluripotent stem cell differentiation into authentic striatal projection neurons. Stem cell reviews and reports, 9(4), 461-474.

Cavendish, J. Z. et al. (2019). Mitochondrial Movement and Number Deficits in Embryonic Cortical Neurons from 3xTg-AD Mice. Journal of Alzheimer's Disease, 70(1), 139-151.

Chambers, S. M. et al. (2009). Highly efficient neural conversion of human ES and iPS cells by dual inhibition of SMAD signaling. Nature biotechnology, 27(3), 275-280.

Chang, E. et al. (2008). Detection and quantification of tau aggregation using a membrane filter assay. Analytical biochemistry, 373(2), 330-336.

Cherubini, M. et al. (2020). Mitochondrial fission in Huntington's disease mouse striatum disrupts ER-mitochondria contacts leading to disturbances in Ca2+ efflux and Reactive Oxygen Species (ROS) homeostasis. Neurobiology of disease, 136, 104741.

Cho, K. J. et al. (2009). Inhibition of apoptosis signal-regulating kinase 1 reduces endoplasmic reticulum stress and nuclear huntingtin fragments in a mouse model of Huntington disease. Neuroscience, 163(4), 1128-1134.

De Yebenes, J. G. et al. & MermaiHD study investigators. (2011). Pridopidine for the treatment of motor function in patients with Huntington's disease (MermaiHD): a phase 3, randomised, double-blind, placebo-controlled trial. The Lancet Neurology, 10(12), 1049-1057.

Diaz-Vegas, A. R. et al. (2018). Mitochondrial calcium increase induced by RyR1 and IP3R channel activation after membrane depolarization regulates skeletal muscle metabolism. Frontiers in physiology, 9, 791.

Dickinson, B. C. et al. (2013). Preparation and use of MitoPY1 for imaging hydrogen peroxide in mitochondria of live cells. Nature protocols, 8(6), 1249-1259.

Duennwald, M. L. et al. (2008). Impaired ERAD and ER stress are early and specific events in polyglutamine toxicity. Genes & development, 22(23), 3308-3319.

Dyhring, T. et al. (2010). The dopaminergic stabilizers pridopidine (ACR16) and (−)-OSU6162 display dopamine D2 receptor antagonism and fast receptor dissociation properties. European journal of pharmacology, 628(1-3), 19-26.

Eddings, C. R. et al. (2019). Pridopidine protects neurons from mutant-huntingtin toxicity via the sigma-1 receptor. Neurobiology of disease, 129, 118-129.

Ehrnhoefer, D. E. et al. (2018). HACE1 is essential for astrocyte mitochondrial function and influences Huntington disease phenotypes in vivo. Human molecular genetics, 27(2), 239-253.

Ferreira, I. L. et al. (2018). Assessing mitochondrial function in in vitro and ex vivo models of Huntington's disease. In Huntington's Disease (pp. 415-442). Humana Press, New York, NY.

Francardo, V. et al. (2014). Pharmacological stimulation of sigma-1 receptors has neurorestorative effects in experimental parkinsonism. Brain, 137(7), 1998-2014.

Francardo, V. et al. (2019). Pridopidine induces functional neurorestoration via the sigma-1 receptor in a mouse model of Parkinson's disease. Neurotherapeutics, 16(2), 465-479.

Fu, Z. X. et al. (2017). Dendritic mitoflash as a putative signal for stabilizing long-term synaptic plasticity. Nature communications, 8(1), 1-12.

Fujimoto, M. et al. (2011). New insights into the role of mitochondria-associated endoplasmic reticulum membrane. International review of cell and molecular biology, 292, 73-117.

Ganz, J. et al. (2020). A novel specific PERK activator reduces toxicity and extends survival in Huntington's disease models. Scientific reports, 10(1), 1-15.

Garcia-Huerta, P. et al. (2020). Insulin-like growth factor 2 (IGF2) protects against Huntington's disease through the extracellular disposal of protein aggregates. Acta neuropathologica, 140(5), 737-764.

Garcia-Miralles, M. et al. (2017). Early pridopidine treatment improves behavioral and transcriptional deficits in YAC128 Huntington disease mice. JCI insight, 2(23).

Geva, M. et al. (2016). Pridopidine activates neuroprotective pathways impaired in Huntington Disease. Human molecular genetics, 25(18), 3975-3987.

Gomez-Suaga, P. et al. (2019). The VAPB-PTPIP51 endoplasmic reticulum-mitochondria tethering proteins are present in neuronal synapses and regulate synaptic activity. Acta neuropathologica communications, 7(1), 1-13.

Gregianin, E. et al. (2016). Loss-of-function mutations in the SIGMAR1 gene cause distal hereditary motor neuropathy by impairing ER-mitochondria tethering and Ca2+ signalling. Human molecular genetics, 25(17), 3741-3753.

Gromek, K. A. et al. (2014). The oligomeric states of the purified sigma-1 receptor are Stabilized by ligands. Journal of Biological Chemistry, 289(29), 20333-20344.

Hamilton, J. et al. (2015). Oxidative metabolism in YAC128 mouse model of Huntington's disease. Human molecular genetics, 24(17), 4862-4878.

Hanner, M. et al. (1996). Purification, molecular cloning, and expression of the mammalian sigma1-binding site. Proceedings of the National Academy of Sciences, 93(15), 8072-8077.

Hayashi, T. (2015). Sigma-1 receptor: the novel intracellular target of Neuropsychotherapeutic drugs. Journal of pharmacological sciences, 127(1), 2-5.

(56) References Cited

OTHER PUBLICATIONS

Hayashi, T. et al. (2000). Ca2+ Signaling via ç1-Receptors: novel regulatory mechanism affecting intracellular Ca2+ concentration. Journal of Pharmacology and Experimental Therapeutics, 293(3), 788-798.

Hayashi, T. et al. (2003) Sigma-1 receptors (sigma(1) binding sites) form raft-like microdomains and target lipid droplets on the endoplasmic reticulum: roles in endoplasmic reticulum lipid compartmentalization and export. The Journal of pharmacology and experimental therapeutics 306, 718-725.

Hayashi, T. et al. (2007). Sigma-1 receptor chaperones at the ER-mitochondrion interface regulate Ca2+ signaling and cell survival. Cell, 131(3), 596-610.

Hayashi, T. et al. (2009). MAM: more than just a housekeeper. Trends in cell biology, 19(2), 81-88.

Hayashi, T. et al. (2010). Detergent-resistant microdomains determine the localization of σ-1 receptors to the endoplasmic reticulum-mitochondria junction. Molecular pharmacology, 77(4), 517-528.

Hedskog, L. et al. (2013). Modulation of the endoplasmic reticulum-mitochondria interface in Alzheimer's disease and related models. Proceedings of the National Academy of Sciences, 110(19), 7916-7921.

Herbert, A. D. et al. (2014). FindFoci: a focus detection algorithm with automated parameter training that closely matches human assignments, reduces human inconsistencies and increases speed of analysis. PloS one, 9(12), e114749.

Herrera, F. et al. (2011). Visualization of cell-to-cell transmission of mutant Ihuntingtin oligomers. PLoS currents, 3.

Hong, W. et al. (2004). Modulation of bradykinin-induced calcium changes in SH-SY5Y cells by neurosteroids and sigma receptor ligands via a shared mechanism. Synapse, 54(2), 102-110.

Huntington Study Group HART Investigators. (2013). A randomized, double-blind, placebo-controlled trial of pridopidine in Huntington's disease. Movement Disorders, 28(10), 1407-1415.

Hyrskyluoto, A. et al. (2013). Sigma-1 receptor agonist PRE084 is protective against mutant huntingtin-induced cell degeneration: involvement of calpastatin and the NF-κ B pathway. Cell death & disease, 4(5), e646-e646.

International Search Report for PCT Application No. PCT/IL2020/050308 dated Jun. 21, 2020.

Ionescu, A. et al. (2019). Targeting the sigma-1 receptor via pridopidine ameliorates central features of ALS pathology in a SOD1 G93A model. Cell death & disease, 10(3), 1-19.

Izumi, Y. et al. (2018) Compound heterozygote mutations in the SIGMAR1 gene in an oldest-old patient with amyotrophic lateral sclerosis. Geriatr Gerontol Int 18, 1519-1520.

Johnston, T. H. et al. (2019). Pridopidine, a clinic-ready compound, reduces 3, 4-dihydroxyphenylalanine-induced dyskinesia in Parkinsonian macaques. Movement Disorders, 34(5), 708-716.

Kamhi-Nesher, S. et al. (2001). A novel quality control compartment derived from the endoplasmic reticulum. Molecular biology of the cell, 12(6), 1711-1723.

Kawamata, H. et al. (2018). Correction: Proteinopathies and OXPHOS dysfunction in neurodegenerative diseases. Journal of Cell Biology, 217(1), 429-429.

Kobayashi, T. et al. (1996). Enhancement of acetylcholine release by SA4503, a novel sigma 1 receptor agonist, in the rat brain. Journal of Pharmacology and Experimental Therapeutics, 279(1), 106-113.

Kondratyev, M. et al. (2007). PERK-dependent compartmentalization of ERAD and unfolded protein response machineries during ER stress. Experimental cell research, 313(16), 3395-3407.

Kourrich, S. et al. (2012). The sigma-1 receptor: roles in neuronal plasticity and disease. Trends in neurosciences, 35(12), 762-771.

Kusko, R. et al. (2018). Large-scale transcriptomic analysis reveals that pridopidine reverses aberrant gene expression and activates neuroprotective pathways in the YAC128 HD mouse. Molecular neurodegeneration, 13(1), 1-15.

Lajoie, P. et al. (2010). Formation and toxicity of soluble polyglutamine oligomers in living cells. PloS one, 5(12), e15245.

Leal, N. S. et al. (2018). Alterations in mitochondria-endoplasmic reticulum connectivity in human brain biopsies from idiopathic normal pressure hydrocephalus patients. Acta neuropathologica communications, 6(1), 1-9.

Leal, N. S. et al. (2020). Amyloid β-Peptide Increases Mitochondria-Endoplasmic Reticulum Contact Altering Mitochondrial Function and Autophagosome Formation in Alzheimer's Disease-Related Models. Cells, 9(12), 2552.

Lee, K. S. et al. (2018). Altered ER-mitochondria contact impacts mitochondria calcium homeostasis and contributes to neurodegeneration in vivo in disease models. Proceedings of the National Academy of Sciences, 115(38), E8844-E8853.

Leitman, J. et al. (2013). Soluble forms of polyQ-expanded huntingtin rather than large aggregates cause endoplasmic reticulum stress. Nature communications, 4(1), 1-10.

Leitman, J. et al. (2014). ER stress-induced elF2-alpha phosphorylation underlies sensitivity of striatal neurons to pathogenic huntingtin. PloS one, 9(3), e90803.

Lewis, T. L. e tal. (2018). MFF-dependent mitochondrial fission regulates presynaptic release and axon branching by limiting axonal mitochondria size. Nature communications, 9(1), 1-15.

Li, X. et al. (2015). A SIGMAR1 splice-site mutation causes distal hereditary motor neuropathy. Neurology, 84(24), 2430-2437.

Lucas, G. et al. (2008). Further evidence for an antidepressant potential of the selective δ1 agonist SA 4503: electrophysiological, morphological and behavioural studies. International Journal of Neuropsychopharmacology, 11(4), 485-495.

Matsuno, K. et al. (1994). Ameliorating effects of σ receptor ligands on the impairment of passive avoidance tasks in mice: involvement in the central acetylcholinergicsystem. European journal of pharmacology, 261(1-2), 43-51.

Matsuno, K. et al. (1997). SA4503, a novel cognitive enhancer, with σ1 receptor agonistic properties. Behavioural brain research, 83(1-2), 221-224.

Maurice, T. (2001). Beneficial effect of the σ1 receptor agonist PRE-084 against the spatial learning deficits in aged rats. European journal of pharmacology, 431(2), 223-227.

Maurice, T. (2020). Bi-phasic dose response in the preclinical and clinical developments of sigma-1 receptor ligands for the treatment of neurodegenerative disorders. Expert Opinion on Drug Discovery, 1-17.

McGarry, A. et al. (2017). Safety and exploratory efficacy at 36 months in Open-HART, an open-label extension study of pridopidine in Huntington's disease. Journal of Huntington's disease, 6(3), 189-199.

Miki, Y. et al. (2015). Sigma-1 receptor is involved in degradation of intranuclear inclusions in a cellular model of Huntington's disease. Neurobiology of disease, 74, 25-31.

Mishina, M. et al. (2008). Low density of sigma 1 receptors in early Alzheimer's disease. Annals of nuclear medicine, 22(3), 151-156.

Mitsuda, T. et al. (2011). Sigma-1Rs are upregulated via PERK/elF2α/ATF4 pathway and execute protective function in ER stress. Biochemical and biophysical research communications, 415(3), 519-525.

Monnet, F. P. (2005). Sigma-1 receptor as regulator of neuronal intracellular Ca2+: clinical qand therapeutic relevance. Biology of the Cell, 97(12), 873-883.

Monnet, F. P. et al. (1992). Neuropeptide Y potentiates the N-methyl-D-aspartate response in the CA3 dorsal hippocampus. II. Involvement of a subtype of sigma receptor. Journal of Pharmacology and Experimental Therapeutics, 263(3), 1219-1225.

Morris, G. et al. (2018). The endoplasmic reticulum stress response in neuroprogressive diseases: emerging pathophysiological role and translational implications. Molecular neurobiology, 55(12), 8765-8787.

Naia, L. et al. (2017). Mitochondrial Ca2+ handling in Huntington's and Alzheimer's diseases—Role of ER-mitochondria crosstalk. Biochemical and biophysical research communications, 483(4), 1069-1077.

Naia, L. et al. (2018). Isolation and Maintenance of Striatal Neurons. Bio-protocol, 8(8), e2823-e2823.

Naia, L. et al. (Jun. 2018). Pridopidine improves overall mitochondrial function in cellular models of Huntington's disease. In *European*

(56)          References Cited

OTHER PUBLICATIONS

*Journal of Clinical Investigation* (vol. 48, pp. 55-55). 111 River St, Hoboken 07030-5774, NJ USA: Wiley.

Neueder, A. et al. (2017). The pathogenic exon 1 HTT protein is produced by incomplete splicing in Huntington's disease patients. Scientific reports, 7(1), 1-10.

Nguyen, L. et al. (2015). Role of sigma-1 receptors in neurodegenerative diseases. Journal of pharmacological sciences, 127(1), 17-29.

Nguyen, L. et al. (2017). Sigma-1 receptors and neurodegenerative diseases: towards a hypothesis of sigma-1 receptors as amplifiers of neurodegeneration and neuroprotection. Sigma Receptors: Their Role in Disease and as Therapeutic Targets, 133-152.

Nguyen, T. et al. (2003). Regulatory mechanisms controlling gene expression mediated by the antioxidant response element. Annual review of pharmacology and toxicology, 43(1), 1233-260.

Nicoleau, C. et al. (2013). Embryonic stem cells neural differentiation qualifies the role of Wnt/β-Catenin signals in human telencephalic specification and regionalization. Stem (cells, 31(9), 1763-1774.

Niescier, R. F. et al. (2018). MCU interacts with Miro1 to modulate mitochondrial functions in neurons. Journal of Neuroscience, 38(20), 4666-4677.

Noh, J. Y. et al. (2009). SCAMPS links endoplasmic reticulum stress to the accumulation of expanded polyglutamine protein aggregates via endocytosis inhibition. Journal of Biological Chemistry, 284(17), 11318-11325.

Omi, K. et al. (2005). siRNA-mediated inhibition of endogenous Huntington disease gene expression induces an aberrant configuration of the ER network in vitro. Biochemical and biophysical research communications, 338(2), 1229-1235.

Onofre, I. et al. (2016). Fibroblasts of Machado Joseph disease patients reveal autophagy impairment. Scientific reports, 6(1), 1-10.

Paillusson, S. et al. (2016). There's something wrong with my MAM; the ER-mitochondriaaxis and neurodegenerative diseases. Trends in neurosciences, 39(3), 146-157.

Paillusson, S. et al. (2017). α-Synuclein binds to the ER-mitochondria tethering protein VAPB to disrupt Ca 2+ homeostasis and mitochondrial ATP production. Acta neuropathologica, 134(1), 129-149.

Pal, A. et al. (2012). The sigma-1 receptor protects against cellular oxidative stress and activates antioxidant response elements. European journal of pharmacology, 682(1-3), 12-20.

Pande, A. C. et al. (1999). A placebo-controlled trial of igmesine in the treatment of major depression. European Neuropsychopharmacology, (9), 138.

Panov, A. V. et al. (2002). Early mitochondrial calcium defects in Huntington's disease are a direct effect of polyglutamines. Nature neuroscience, 5(8), 731-736.

Park, I. H. et al. (2008). Disease-specific induced pluripotent stem cells. cell, 134(5), 877-886.

Rabinovich-Guilatt, L. et al. (2016). The effect of mild and moderate renal impairment on the pharmacokinetics of pridopidine, a new drug for Huntington's disease. British journal of clinical pharmacology, 81(2), 246-255.

Rabinovich-Guilatt, L. et al. (2017). Metoprolol-pridopidine drug-drug interaction and food effect assessments of pridopidine, a new drug for treatment of Huntington's disease. British journal of clinical pharmacology, 83(10), 2214-2224.

Rejonen, S. et al. (2008), Inhibition of endoplasmic reticulum stress counteracts neuronal cell death and protein aggregation caused by N-terminal mutant huntingtin proteins. Experimental cell research, 314(5), 950-960.

Reilmann, R. et al. & European Huntington's Disease Network. (2019). Safety and efficacy of pridopidine in patients with Huntington's disease (PRIDE-HD): a phase 2, randomised, placebo-controlled, multicentre, dose-ranging study. The Lancet Neurology, 18(2), 165-176.

Reilmann, R. et al. (Oct. 2019). Novel PET data and analysis of early HD from PRIDE-HD. In Neurotherapeutics (vol. 16, No. 4, pp. 1360-1360). One New York Plaza, Suite 4600, New York, NY, United States: Springer.

Ribeiro, M. et al. (2014). Insulin and IGF-1 improve mitochondrial function in a PI-3K/Akt-dependent manner and reduce mitochondrial generation of reactive oxygen species in Huntington's disease knock-in striatal cells. Free Radical Biology and Medicine, 74, 129-144.

Rietdorf J, A S. Multi Kymograph [Internet]. 2008. Available from: http://fiji.sc/Multi_Kymograph.

Rogers, G. W. et al. (2011). High throughput microplate respiratory measurements using minimal quantities of isolated mitochondria. PloS one, 6(7), e21746.

Ron, D. (2002). Translational control in the endoplasmic reticulum stress response. The Journal of clinical investigation, 110(10), 1383-1388.

Rossi, A. et al. (2019). Calcium, mitochondria and cell metabolism: A functional triangle in bioenergetics. Biochimica et Biophysica Acta (BBA)-Molecular Cell Research, 1866(7), 1068-1078.

Rousseaux, C. G. et al. (2016). Sigme receptors [σRs]: biology in normal and diseased states. Journal of Receptors and Signal Transduction, 36(4), 327-388.

Ryskamp, D. A. et al. (2019). Mutational analysis of sigma-1 receptor's role in synaptic stability. Frontiers in neuroscience, 13, 1012.

Ryskamp, D. et al. (2017). The sigma-1 receptor mediates the beneficial effects of pridopidine in a mouse model of Huntington disease. Neurobiology of disease, 97, 46-59.

Ryskamp, D. et al. (2019). Pridopidine stabilizes mushroom spines in mouse models of Alzheimer's disease by acting on the sigma-1 receptor. Neurobiology of disease, 124, 489-504.

Sahlholm, K. et al. (2013). The dopamine stabilizers ACR16 and (−)-OSU6162 display nanomolar affinities at the σ-1 receptor. Molecular psychiatry, 18(1), 12-14.

Sahlholm, K. et al. (2015). Pridopidine selectively occupies sigma-1 rather than dopamine D2 receptors at behaviorally active doses. Psychopharmacology, 232(18), 3443-3453.

Schaffar, G. et al. (2004). Cellular toxicity of polyglutamine expansion proteins: Imechanism of transcription factor deactivation. Molecular cell, 15(1), 95-105.

Schmidt, H. R. et al. (2016). Crystal structure of the human σ 1 receptor. Nature, 532(7600), 527-530.

Shacham, T. et al. (2019). Protein misfolding and ER stress in Huntington's disease. Frontiers in molecular biosciences, 6, 20.

Slow, E. J. et al. (2003). Selective striatal neuronal loss in a YAC128 mouse model of Huntington disease. Human molecular genetics, 12(13), 1555-1567.

Smith-Duak, A. I. et al. (2019). Impairment and restoration of homeostatic plasticity in cultured cortical neurons from a mouse model of huntington disease. Frontiers in cellular neuroscience, 13, 209.

Squitieri, F. et al. (2015). Pridopidine, a dopamine stabilizer, improves motor performance and shows neuroprotective effects in Huntington disease R6/2 mouse model. Journal of cellular and molecular medicine, 19(11), 2540-2548.

Su, T. P. et al. (2010). The sigma-1 receptor chaperone as an inter-organelle signaling modulator. Trends in pharmacological sciences, 31(12), 557-566.

Su, T. P. et al. (2016). The sigma-1 receptor as a pluripotent modulator in living systems. Trends in pharmacological sciences, 37(4), 262-278.

Takahashi, T. et al. (2008). Soluble polyglutamine oligomers formed prior to inclusion body formation are cytotoxic. Human molecular genetics, 17(3), 345-356.

Tang, T. S. et al. (2003). Huntingtin and huntingtin-associated protein 1 influence neuronal calcium signaling mediated by inositol-(1, 4, 5) triphosphate receptor type 1. Neuron, 39(2), 227-239.

Tang, T. S. et al. (2005). Disturbed Ca2+ signaling and apoptosis of medium spiny neurons in Huntington's disease. Proceedings of the National Academy of Sciences, 102(7), 2602-2607.

Trettel, F. et al. (2000). Dominant phenotypes produced by the HD mutation in ST Hdh Q111 striatal cells. Human molecular genetics, 9(19), 2799-2809.

Tsai, S. Y. A. et al. (2014). Sigma-1 receptor chaperones in neurodegenerative and psychiatric disorders. Expert opinion on therapeutic targets, 18(12), 1461-1476.

(56)  References Cited

OTHER PUBLICATIONS

Urani, A. et al. (2004). Enhanced antidepressant efficacy of σ1 receptor agonists in rats after chronic intracerebroventricular infusion of β-amyloid-(1-40) protein. European journal lof pharmacology, 486(2), 151-161.

Vagnerova, K. et al. (2006). Sigma 1 receptor agonists act as neuroprotective drugs through inhibition of inducible nitric oxide synthase. Anesthesia & Analgesia, 103(2), 430-434.

Van Raamsdonk, J. M. et al. (2005). Cognitive dysfunction precedes neuropathology and motor abnormalities in the YAC128 mouse model of Huntington's disease. Journal of Neuroscience, 25(16), 4169-4180.

Ververis, A. et al. (2020). Distal hereditary motor neuronopathy of the Jerash type is caused by a novel SIGMAR1 c. 500A>T missense mutation. Journal of medical (genetics, 57(3), 178-186.

Vidal, R. L. et al. (2012). Targeting the UPR transcription factor XBP1 protects against Huntington's disease through the regulation of FoxO1 and autophagy. Human molecular genetics, 21(10), 2245-2262.

Wang, X. et al. (2018). Systematic In-Depth Proteomic Analysis of Mitochondria-Associated Endoplasmic Reticulum Membranes in Mouse and Human Testes. Proteomics, 18(14), 1700478.

Watanabe, S. et al. (2016). Mitochondria-associated membrane collapse is a common pathomechanism in SIGMAR 1-and SOD 1-linked ALS. EMBO molecular medicine, 8(12), 1421-1437.

Weng, T. Y. et al. (2017). Loss of sigma-1 receptor chaperone promotes astrocytosis and enhances the Nrf2 antioxidant defense. Oxidative medicine and cellular longevity, 2017.

Wong, A. Y. et al. (2016). Aberrant subcellular dynamics of sigma-1 receptor mutants underlying neuromuscular diseases. Molecular pharmacology, 90(3), 238-253.

Yang, H. et al. (2010). Huntingtin interacts with the cue domain of gp78 and inhibits gp78 binding to ubiquitin and p97/VCP. PloS one, 5(1), e8905.

Zhou, Z. et al. (2020). Endoplasmic reticulum-associated degradation regulates mitochondrial dynamics in brown adipocytes. Science, 368(6486), 54-60.

Zoghbi, H. Y. et al. (2000). Glutamine repeats and neurodegeneration. Annual review of neuroscience, 23(1), 217-247.

Bottoni P, et al. Remarks on mitochondrial myopathies. *International Journal of Molecular Sciences*. Dec. 21, 2022;24(1):124.

Cagalinec M, et al. Role of mitochondrial dynamics in neuronal development: mechanism for Wolfram syndrome. *PLoS biology*. Jul. 19, 2016;14(7):e1002511.

Chanprasert S, et al. Molecular and clinical characterization of the myopathic form of mitochondrial DNA depletion syndrome caused by mutations in the thymidine kinase (TK2) gene. *Molecular genetics and metabolism*. Sep. 1, 2013;110(1-2):153-61.

Dimauro S. Mitochondrial myopathies. *Current opinion in rheumatology*. Nov. 1, 2006;18(6):636-41.

Farruggia P, et al. Pearson syndrome. *Expert review of hematology*. Mar. 4, 2018;11(3):239-46.

Finsterer J. Neuropathy, ataxia, and retinitis Pigmentosa syndrome. *Journal of Clinical Neuromuscular Disease*. Mar. 1, 2023;24(3):140-6.

Hirano M, et al. Topical review: mitochondrial myopathy, encephalopathy, lactic acidosis, and strokelike episodes (MELAS): current concepts. Journal of child neurology. Jan. 1994;9(1):4-13.

Nishino I, et al. MNGIE: from nuclear DNA to mitochondrial DNA. *Neuromuscular Disorders*. Jan. 1, 2001;11(1):7-10.

Rahman S, et al. Leigh syndrome: clinical features and biochemical and DNA abnormalities. *Annals of Neurology: Official Journal of the American Neurological Association and the Child Neurology Society*. Mar. 1996;39(3):343-51.

Saneto RP, et al. Alpers-huttenlocher syndrome. *Pediatric Neurology*. Mar. 1, 2013;48(3):167-78.

Schmucker S, et al. Understanding the molecular mechanisms of Friedreich's ataxia to develop therapeutic approaches. *Human Molecular Genetics*. Apr. 15, 2010;19(R1):R103-10.

Shoffner JM, et al. Myoclonic epilepsy and ragged-red fiber disease (MERRF) is associated with a mitochondrial DNA tRNALys mutation. *Cell*. Jun. 15, 1990;61(6):931-7.

Van Den Ouweland JM, et al. Maternally inherited diabetes and deafness is a distinct subtype of diabetes and associates with a single point mutation in the mitochondrial tRNA Leu (UUR) gene. *Diabetes*. Jun. 1, 1994;43(6):746-51.

Zatyka M, et al. Depletion of WFS1 compromises mitochondrial function in hiPSC-derived neuronal models of Wolfram syndrome. *Stem Cell Reports*. May 9, 2023;18(5):1090-106.

Ashizawa, T., & Xia, G. (2016). Ataxia. Continuum, 22(4), 1208-1226.

Bundey, S. (1993). Wolfram syndrome: mitochondrial disorder. The Lancet, 342(8878), 1059-1060.

Klockgether, T. (2005). Ataxias. Diagnostic procedure and treatment. Der Nervenarzt, 76(10), 1275-83.

Wabbels, B., et al. (2008). Chronisch-progressive externe Ophthalmoplegie und Kearns-Sayre-Syndrom. Der Ophthalmologe, 105(6), 550-556.

Ahmed, S. T., et al. (2018). Diagnosis and treatment of mitochondrial myopathies. *Neurotherapeutics*, 15(4), 943-953.

Axelrod, F. B., & Simson, G. V. (2007). Hereditary sensory and autonomic neuropathies: types II, III, and IV. *Orphanet journal of rare diseases*, 2(1), 39.

El-Hattab, A. W., et al. (2013). Mitochondrial DNA depletion syndromes: review and updates of genetic basis, manifestations, and therapeutic options. *Neurotherapeutics*, 10(2), 186-198.

Slaugenhaupt, S. A., & Gusella, J. F. (2002). Familial dysautonomia. *Current opinion in genetics & development*, 12(3), 307-311.

* cited by examiner

WT Basal

Y128 Basal

Y128 Pri 1 µM

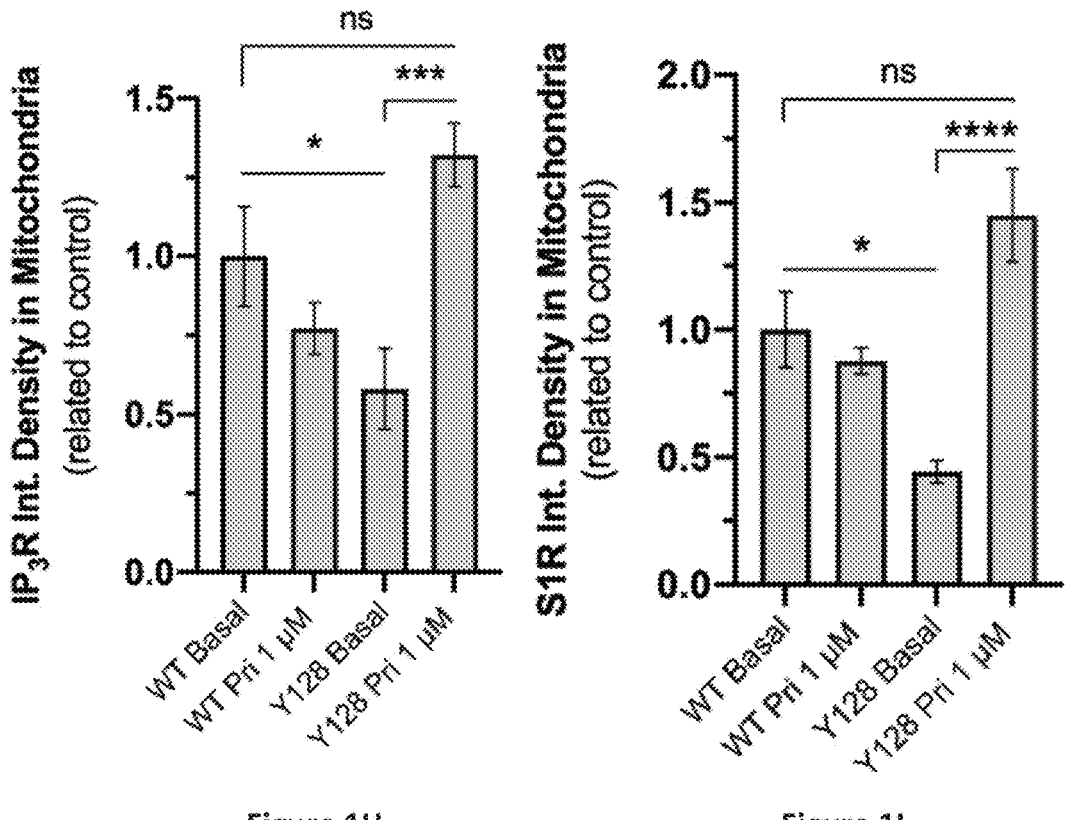
Figure 1H                                          Figure 1I
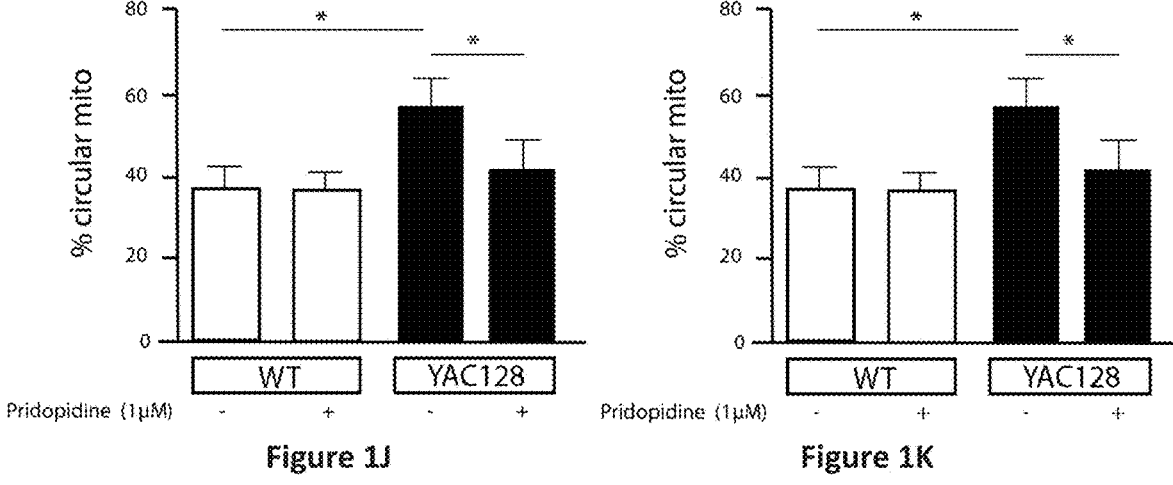
Figure 1J                                          Figure 1K

*ATP*
*production*

Human Lymphoblasts

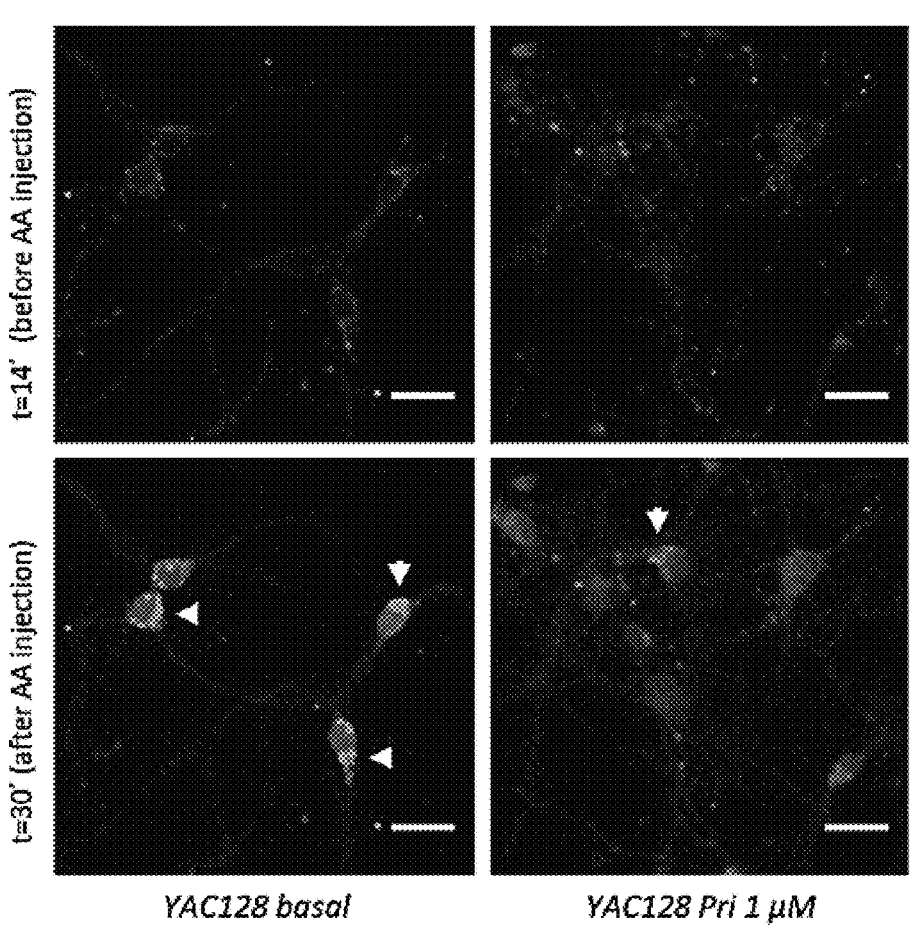
Figure 5A
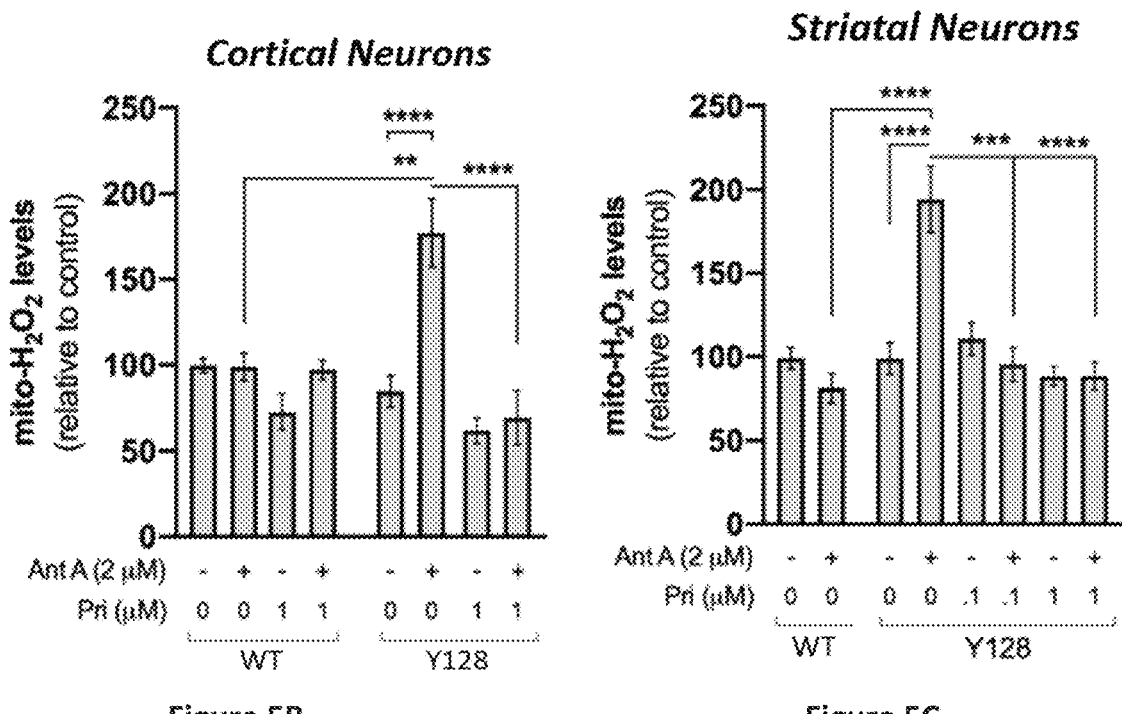
Figure 5B                         Figure 5C

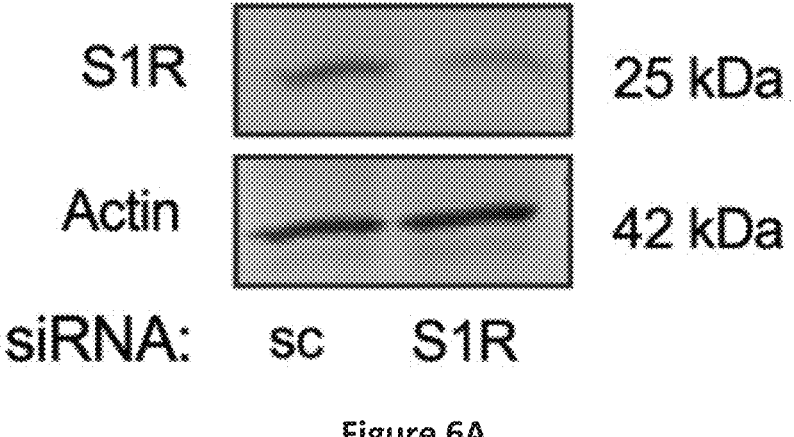
Figure 6A
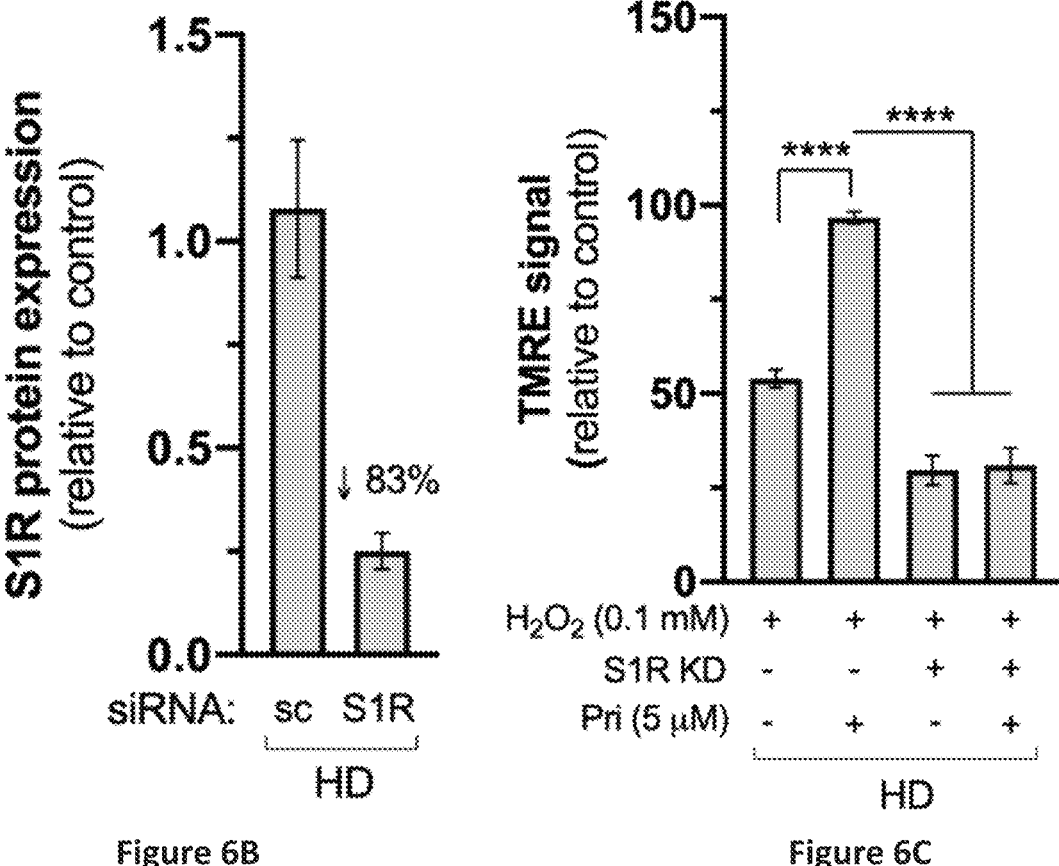
Figure 6B
Figure 6C

——— Pridopidine treatment
∙∙∙➤ Mitochondrial experiments

W: weight
RR: rotarod (constant & accelerated speed)

MI: mitochondria isolation
AR: H₂O₂ levels
EF: electron flow

Pre-treatment
accelerating rotarod:
1.5 mo

Post-tretment
accelerating rotarod:
3 mo

Figure 7F                    Figure 7G

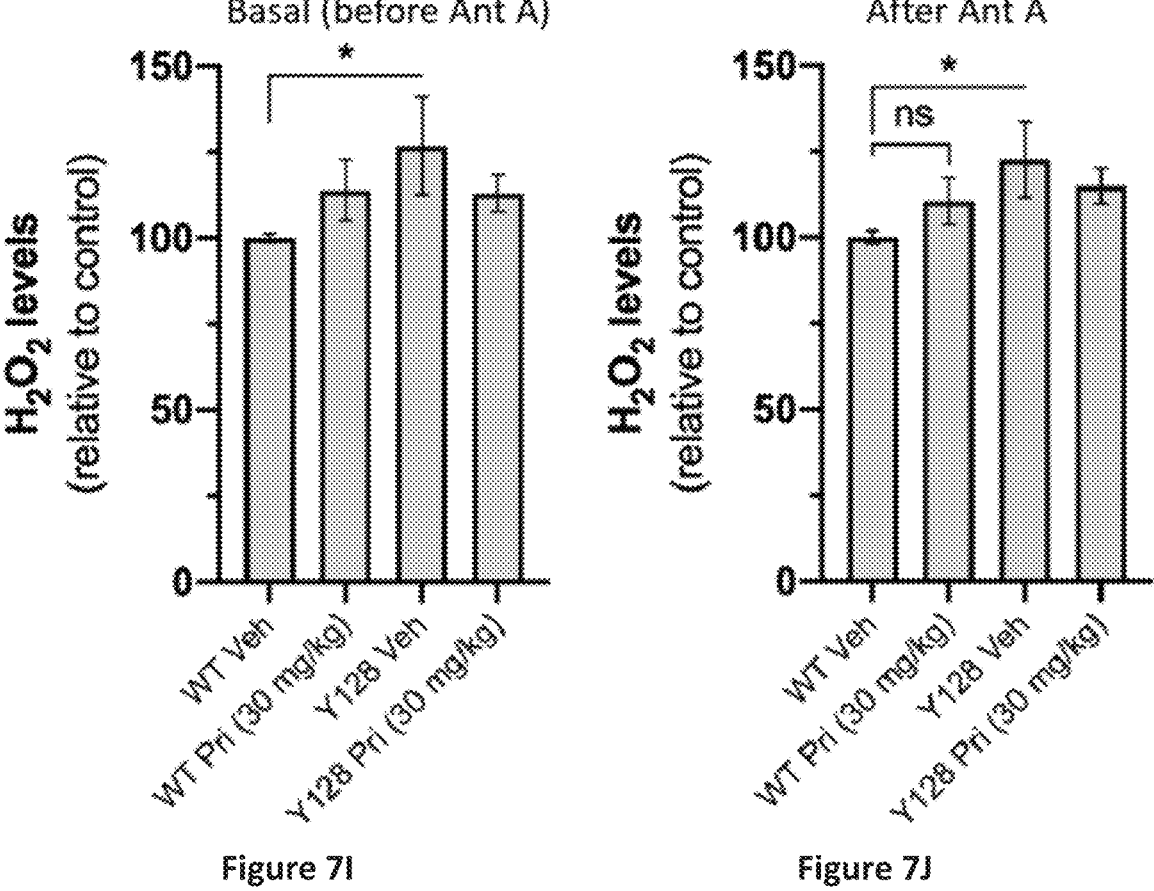
Figure 7I                                    Figure 7J

PRIDOPIDINE FOR THE TREATMENT OF MITOCHONDRIAL-ASSOCIATED DISEASES AND DISORDERS AND ENDOPLASMIC RETICULUM (ER) STRESS

CROSS REFERENCE TO RELATED APPLICATIONS

This application is a continuation-in-part of PCT International Application No. PCT/IL2020/050308, filed on Mar. 15, 2020, which claims the benefit of U.S. Provisional Patent Application Ser. No. 62/818,796, filed on Mar. 15, 2019, which are incorporated herein by reference in their entirety.

SEQUENCE LISTING STATEMENT

The instant application contains a Sequence Listing which has been submitted electronically in ASCII format and is hereby incorporated by reference in its entirety. Said ASCII copy, created on February 2021, is named P-585293-US-SQL-23FEB21_ST25.txt and is 1,478 bytes in size.

FIELD OF THE INVENTION

The subject invention provides a method for treating a subject afflicted with a disease, disorder, or condition associated with mitochondrial dysfunction or ER stress, comprising administering to the subject a composition comprising pridopidine or a pharmaceutically acceptable salt thereof.

BACKGROUND

The Sigma-1 receptor (S1R) is a small transmembrane protein (25 KDa) that is preferentially localized at the Endoplasmic Reticulum (ER) subdomain called the mitochondria-associated membrane (MAM). The MAM is a contact point between the ER and mitochondria and allows the exchange of lipids, calcium ($Ca^{2+}$), and reactive oxygen species (ROS) between ER and mitochondria (Hayashi and Su 2007; Vallese et al. 2020; Veeresh et al. 2019).

The ER is an organelle within the cells which plays a key role in the synthesis of proteins, synthesis of lipids and sterols, and storage of free calcium. The mitochondria are responsible for energy production (ATP) within the cell and are involved in cell respiration. The mitochondria and ER are structurally and functionally linked through MAMs.

Calcium ($Ca^{2+}$) exchange between mitochondria and ER disrupts mitochondrial ATP production in numerous neurodegenerative diseases, including Huntington's disease (HD), Alzheimer's disease (AD), and Parkinson's disease (PD). For example, mitochondrial dysfunction and stress are early, central oxidative mechanisms underlying neuronal death in neurodegenerative disorders including Huntington's disease (HD), Alzheimer's disease (AD), Parkinson's disease (PD), ALS and other diseases. Another common hallmark observed innumerous neurodegenerative disease models including HD is dysregulated ER stress, which leads to neuronal cytotoxicity (Delprat et al. 2020; Erpapazoglou, Mouton-Liger, and Corti 2017).

Pridopidine (4-[3-(methylsulfonyl)phenyl]-1-propyl-piperidine); ACR16, Huntexil®, TV-7820) is a highly selective and potent S1R agonist. Pridopidine exerts neuroprotective effects by activation of the S1R in animal and cellular models of neurodegenerative diseases, including models of HD, Parkinson's disease (PD), ALS, retinal neurodegeneration, and Alzheimer's disease (AD) (Smith-Dijak et al. 2019; Eddings et al. 2019; Ryskamp et al. 2018; Francardo et al. 2019; Ionescu et al. 2019).

SUMMARY OF THE INVENTION

In one embodiment, the present invention provides a method of treating, suppressing, or inhibiting a disease, disorder, or condition associated with mitochondrial dysfunction in a subject, or any symptom thereof, comprising administering to said subject a composition comprising pridopidine or pharmaceutically acceptable salt thereof, wherein said disease, disorder, or condition associated with mitochondrial dysfunction comprises: (a) a mood disorder; (b) a mitochondrial myopathy; (c) a lysosomal storage disease; (d) Frontotemporal Dementia (FTD), (e) Charcot-Marie-Tooth Disease (CMT), or a combination thereof.

In another embodiment, the present invention provides a method of improving mitochondrial function, preventing mitochondrial dysfunction, recovering mitochondrial function, or increasing cell viability in a subject comprising administering to the subject a composition comprising pridopidine or pharmaceutically acceptable salt thereof.

In another embodiment, the present invention provides a method of reducing endoplasmic reticulum (ER) stress in a subject comprising administering to the subject a composition comprising pridopidine or pharmaceutically acceptable salt thereof.

BRIEF DESCRIPTION OF THE DRAWINGS

The patent of application file contains at least one drawing executed in color. Copies of this patent or patent application publication with color drawing(s) will be provided by the office upon request and payment of the necessary fee.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 1A-1H. Pridopidine increases mitochondria-Endoplasmic reticulum (ER) coupling and co-localization of IP3R and S1R with mitochondria in YAC128 HD neurons.

FIG. 1A. Representative electron microscope images of ER and mitochondria in striatal neurons. Electron micrographs of WT and YAC128 (Y128) striatal neurons treated for 24 h with 1 µM pridopidine. Mitochondria and ER are highlighted in orange and purple, respectively. FIG. 1B: Quantification of the percent (%) of mitochondria surface in contact with ER. In Y128 neurons the percent of mitochondrial surface in contact with ER is decreased significantly. Pridopidine significantly increases the percent of mitochondria surface in contact with ER in both WT and Y128 neurons. FIG. 1C: Quantification of the number of mitochondria-ER contact sites (MERCS) per mitochondria. MERCS per mitochondria is reduced in Y128 neurons, and significantly increased in response to pridopidine treatment. FIG. 1D: Quantification of the mitochondria aspect ratio, the ratio between the major and minor axes of mitochondria. Aspect ratio is decreased in Y128 neurons and restored to WT levels in response to pridopidine treatment. FIG. 1E: Quantification of ER width. ER width is increased in Y128 neurons, and significantly restored to WT levels as a result of pridopidine treatment. Each dot in the graphs represents a measurement of a single cell from 3 independent primary cultures. Scale bar=300 nm.

FIG. 1F. Electron micrographs were obtained by TEM from striatal neurons treated or non-treated with pridopidine (1 mM, 24 h). Mitochondrial aspect ratio is significantly reduced in Y128 and restored by pridopidine treatment.

FIGS. 1G-1I. YAC128 (Y128) and WT striatal neurons were treated for 24 h with 1 µM pridopidine and transfected with MitoDsRed plasmid, which fluorescently tags mitochondria. IP$_3$R3 and S1R were labelled using specific antibodies and their co-localization with mitochondria was analyzed. FIG. 1G: Representative confocal images of S1R and mitochondria in striatal neurons. FIG. 1H: Quantification of IP$_3$R3 density in mitochondria. FIG. 1I: Quantification of S1R density in mitochondria. Both IP$_3$R3 and S1R densities are reduced in YAC128 neurons. Pridopidine restores levels of both IP$_3$R3 and S1R back to WT levels. Each data point represents an individual neurite analyzed from three independent cultures.

Statistical significance: *p<0.05, p<0.01, *p<0.001 ****p<0.0001 by Kruskal Wallis test followed by Dunn multiple comparison test. ns=non-significant.

FIGS. 1J and 1K: YAC128 HD mitochondria show impaired morphology with increased percentage of circular mitochondria (FIG. 1I) and decreased percentage of elongated mitochondria (FIG. 1J). Pridopidine treatment (1 µM) corrects Y128 morphology to WT levels (n=4). *p<0.05

Figure 2A:
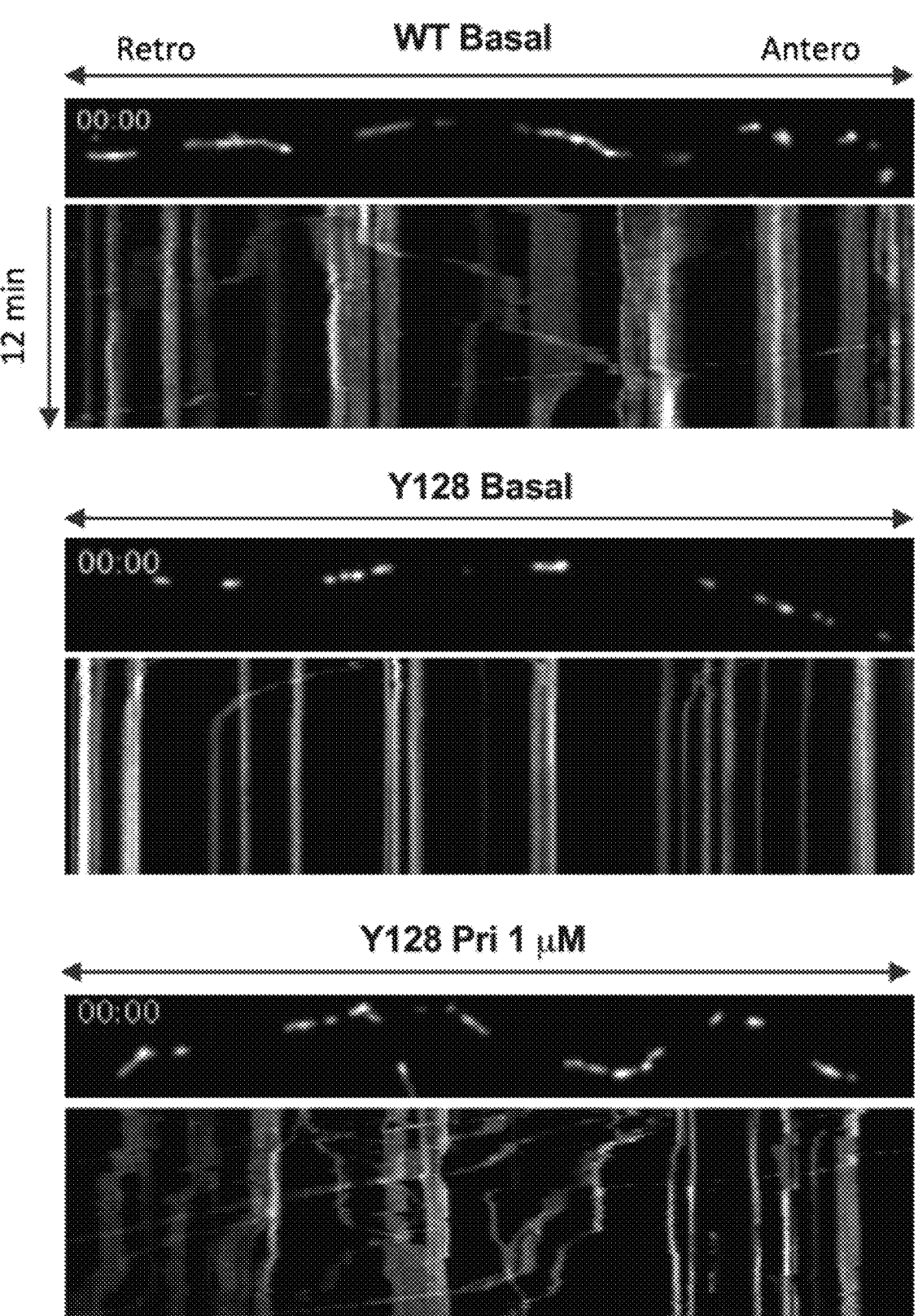
Figure 2B:
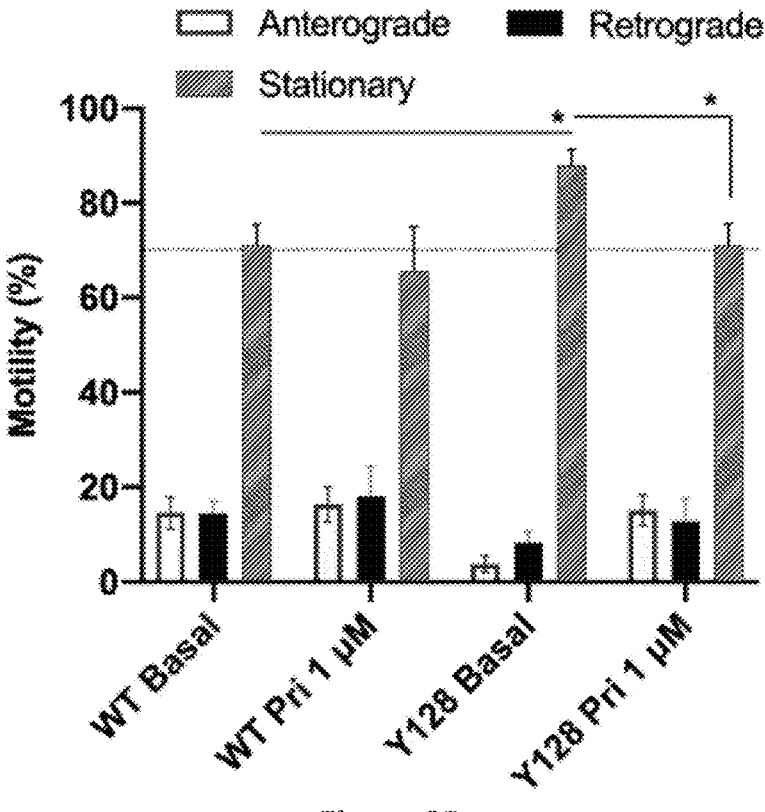
Figure 2C:
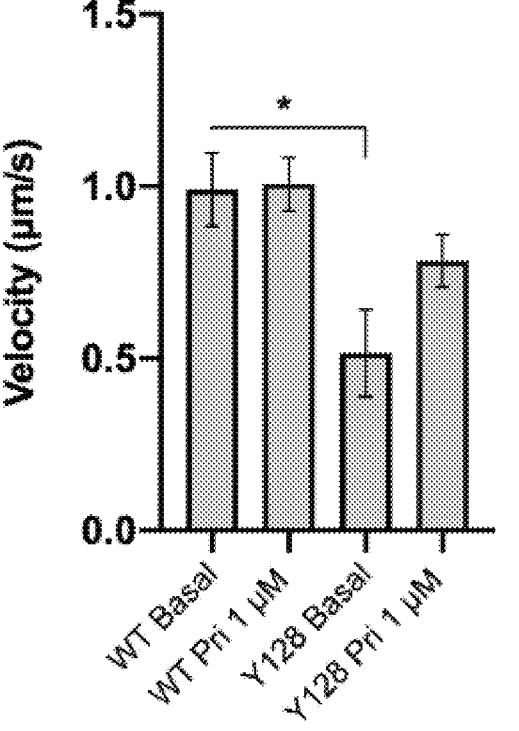

FIGS. 2A-2C. Pridopidine improves mitochondrial anterograde transport in YAC128 neurons.

FIG. 2A. Representative images of mitochondrial transport in YAC128 neurons. Representative images of MitoDsRed-transfected mitochondria live tracked in WT and Y128 neurons using spinning disk confocal. Top panel: representative image of a single neurite. Bottom panel: kymograph plotting distance (x axis) overtime (y axis).

FIG. 2B. Motility analysis of mitochondria by direction of transport. In YAC128 HD neurons there is a significantly higher proportion of stationary mitochondria compared to WT neurons. Pridopidine treatment restores the proportion of stationary mitochondria similar to that of WT neurons. Two-way ANOVA indicates an interaction between the condition and the type of movement [F(6, 87)=3.943, p=0.0016].

FIG. 2C. Quantification of velocity of mitochondrial trafficking from kymograph analysis. Velocity is reduced in Y128 HD neurons compared to WT and is increased in pridopidine-treated neurons. Each data point represents the quantification of an individual kymograph obtained from individual neurites from four independent experiments.

Statistical significance: *p<0.05 by 2-way ANOVA followed by Tukey's multiple comparison test. In FIG. 2C, *p<0.05 by Kruskal Wallis test followed by Dunn multiple comparison test.

FIGS. 3A-3H. Pridopidine enhances mitochondrial respiration in HD cell models.

Figures 3A, 3B, 3C:
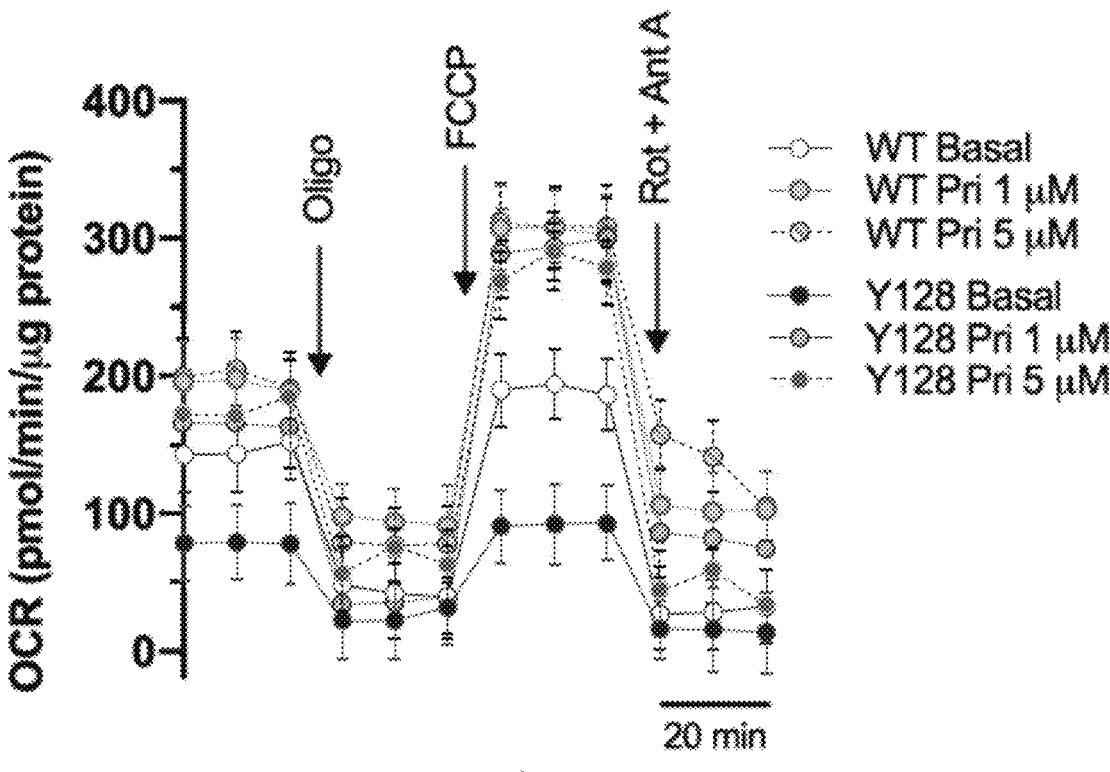
Figure 3D:
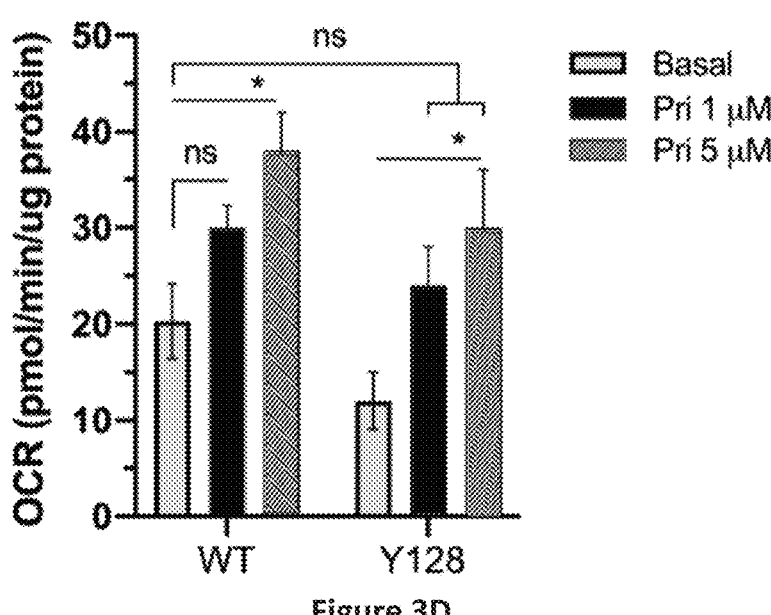

FIGS. 3A-3D. Oxygen consumption evaluated in WT and Y128 cortical/striatal neurons treated with 1 and 5 µM pridopidine for 24 h using the Seahorse flux analyzer (three independent experiments). FIG. 3A: Representative graph of mitochondrial respiration. FIG. 3B: Quantification of basal respiration. Basal respiration is reduced in Y128 cells compared to WT. Pridopidine increases basal respiration in both WT and Y128 cells. FIG. 3C: Quantification of maximal respiration. Maximal respiration is reduced in 128 cells compared to WT. Pridopidine increases maximal respiration in both WT and Y128 cells. FIG. 3D: Quantification of ATP production. Pridopidine increases ATP production in both WT and Y128 cells.

Figure 3E:
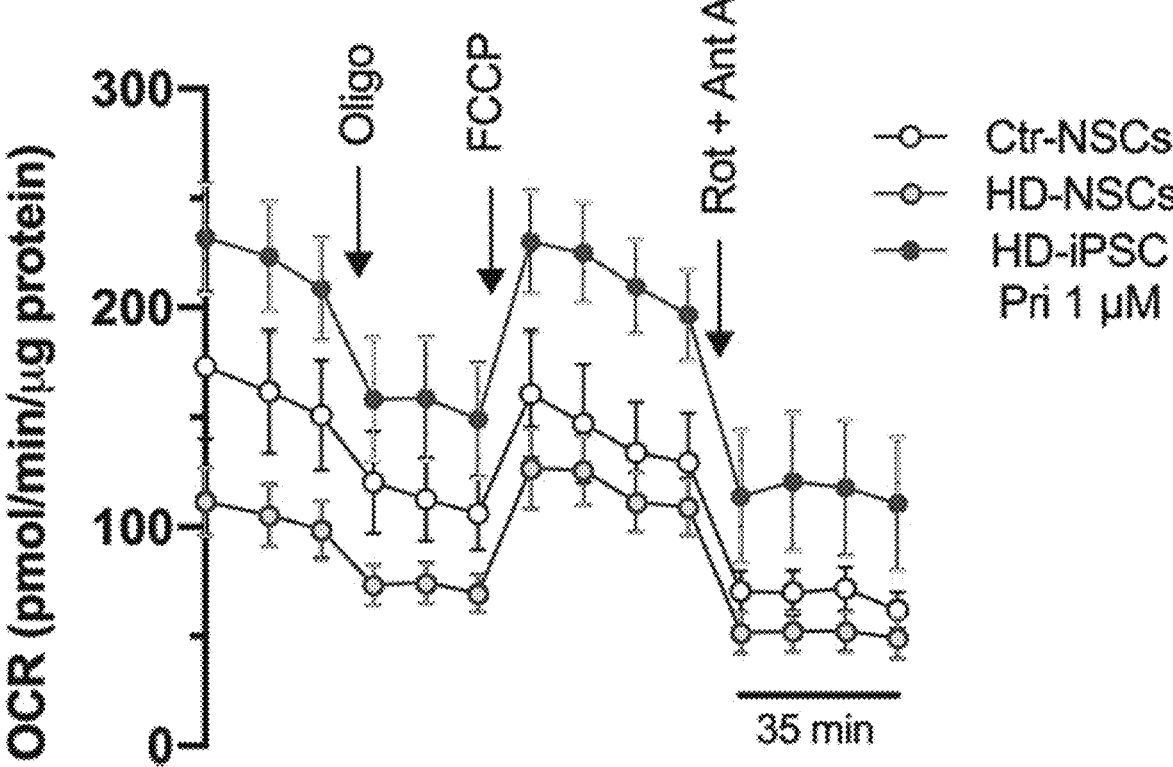
Figures 3F, 3G:
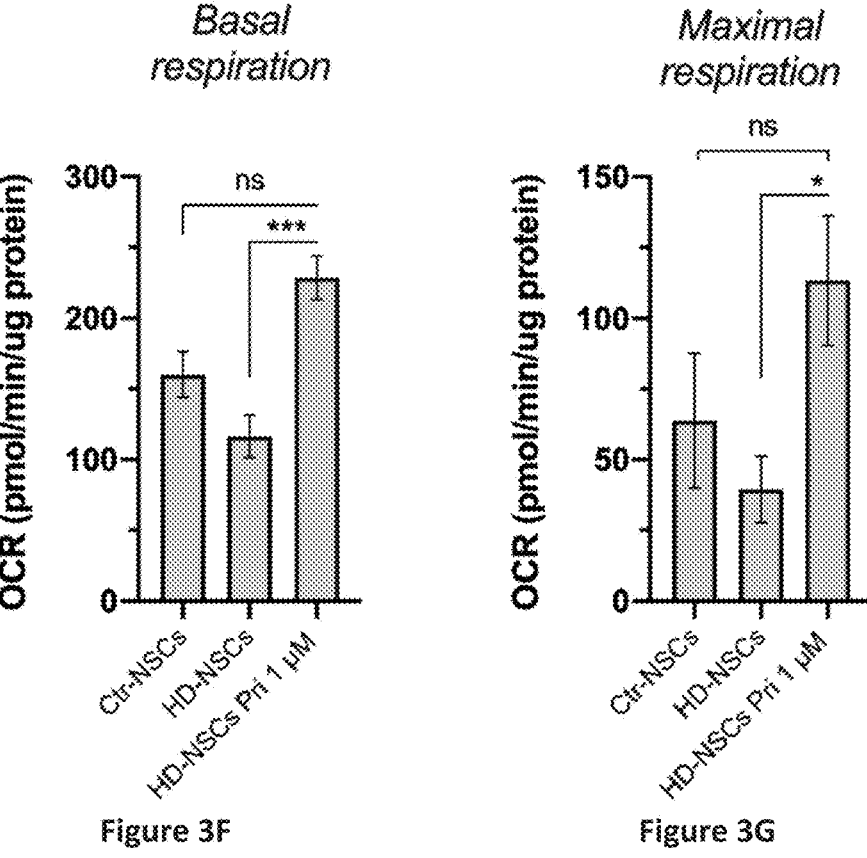
Figure 3H:
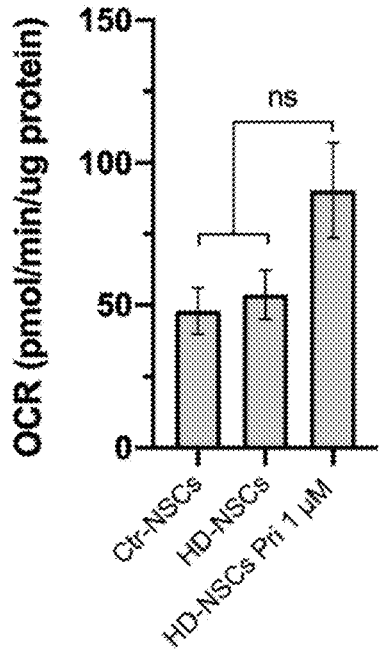

FIGS. 3E-3H. Oxygen consumption evaluated in neural stem cells (NSCs) treated with 0.1 and 1 µM pridopidine for 24 h using the Seahorse flux analyzer (three to four independent experiments). FIG. 3E: Representative graph of mitochondrial respiration in HD NSCs. FIG. 3F: Quantification of basal respiration. FIG. 3G: Quantification of maximal respiration. FIG. 3H: Quantification of ATP production. Basal and maximal respiration are decreased in HD-NSCs. Pridopidine significantly increases basal and maximal respiration in HD NSCs. Similarly, pridopidine shows an increase in ATP production in HD NSCs.

Statistical significance: *p<0.05, p<0.01, *p<0.001 by Kruskal Wallis test followed by Dunn multiple comparison test. ns=non-significant.

FIGS. 4A-4F. Early pridopidine treatment protects YAC128 neurons and HD lymphoblasts against H$_2$O$_2$-induced mitochondrial dysfunction.

Figure 4A:
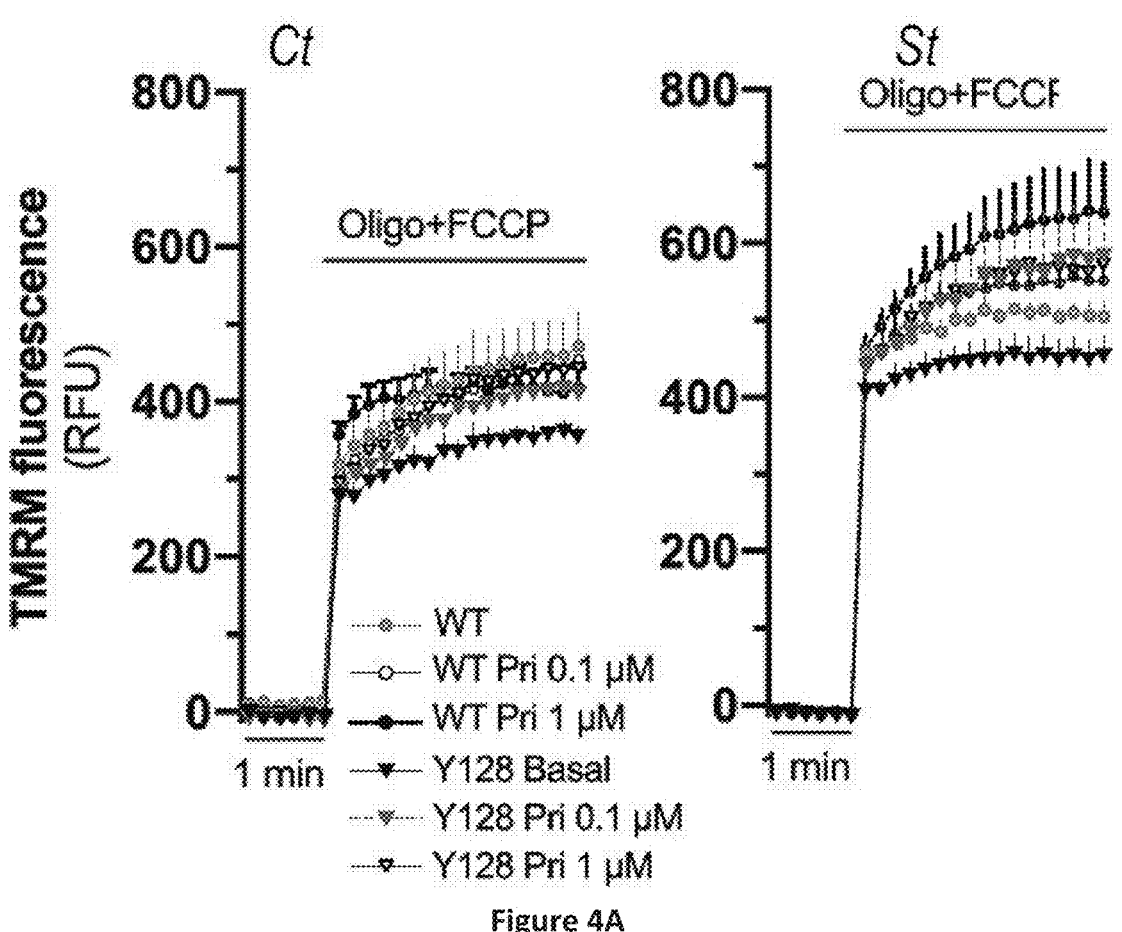
Figures 4B, 4C:
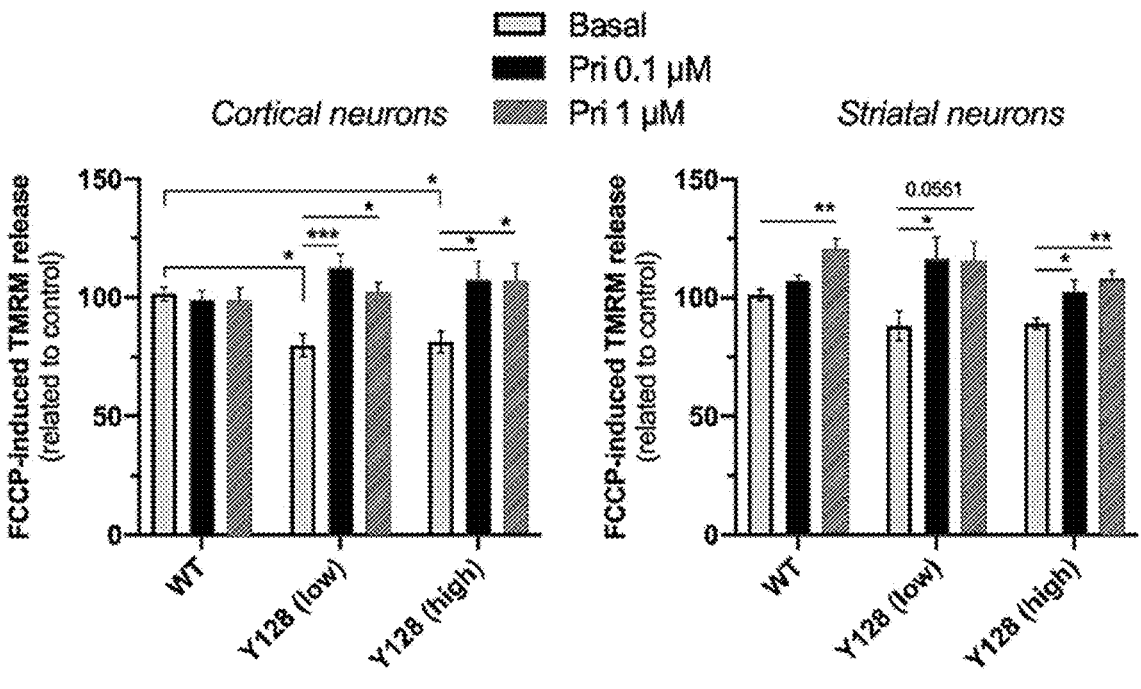

FIGS. 4A-4C. Cortical (Ct, left panel) and striatal (St, right panel) WT and YAC128 neurons expressing either low or high levels of mutant Huntingtin (mHTT) were treated with pridopidine for 24 h. TMRM (tetramethylrhodamine methyl ester) was used to measure changes in mitochondrial membrane potential (MMP, ΔΨ$_m$) after depolarization with oligomycin plus the protonophore Carbonyl cyanide-4-phenylhydrazone (FCCP)(seven to ten independent cultures).

FIG. 4A. Representative graph of mitochondrial membrane potential in neurons. FIG. 4B. Quantification of TMRM release in cortical neurons. FIG. 4C Quantification of TMRM release in striatal neurons. Both high and low expressing mHTT Y128 neurons show decreased membrane potential compared to WT neurons (decreased TMRM release). Pridopidine at both concentrations significantly restores membrane potential in the low and high mHTT expressing cortical (FIG. 4B) and striatal (FIG. 4C) neurons.

Figure 4D:
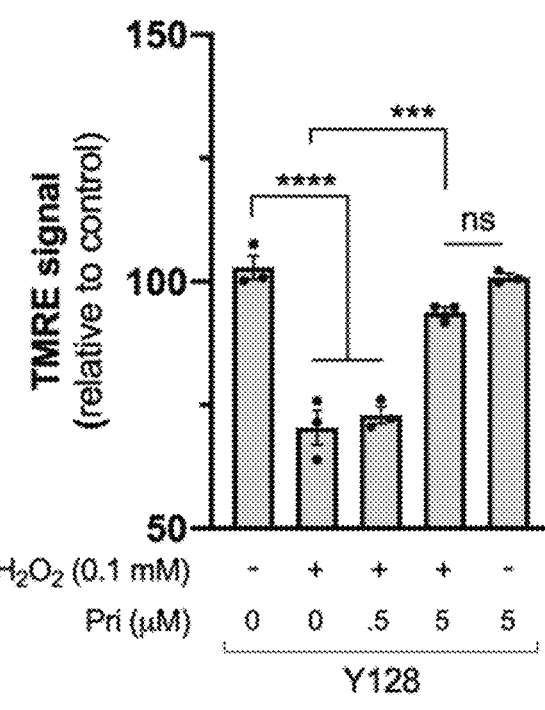

FIG. 4D. Y128 neurons pre-treated with pridopidine for 24 h (at indicated concentrations) were incubated with 0.1 mM H$_2$O$_2$ and MMP was evaluated with TMRE by flow cytometry (three independent cultures). H$_2$O$_2$ challenge significantly reduces MMP (observed by a decrease in TMRE) in Y128 neurons. Pridopidine 5 µM shows a rescue effect on H$_2$O$_2$-induced MMP decrease.

Figure 4E:
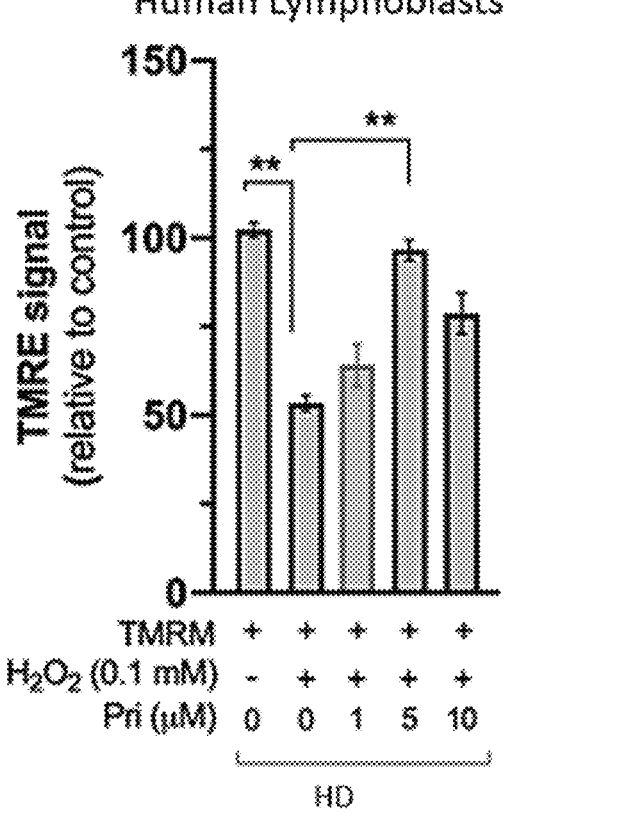

FIG. 4E. HD human lymphoblasts were pre-treated with pridopidine for 24 h and then challenged with H$_2$O$_2$ for 6 h and MMP was evaluated by quantifying the TMRE signal by flow cytometry. H$_2$O$_2$ decreases MMP by ~50%. Pridopidine 5 µM demonstrates a significant rescue effect on TMRE release.

Figure 4F:
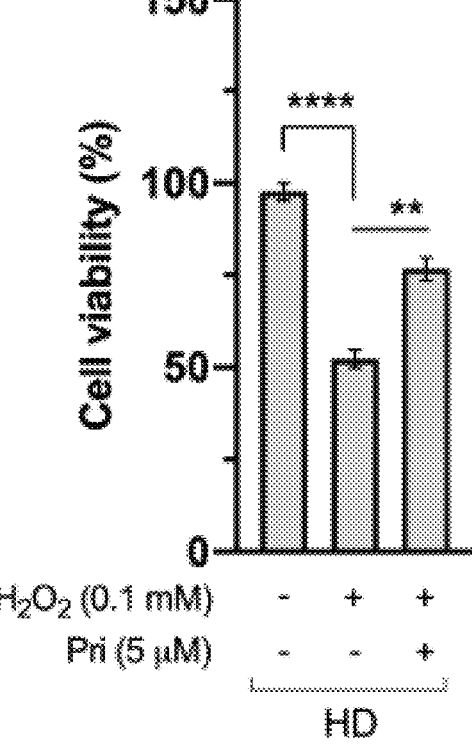

FIG. 4F. Cell viability was evaluated by the colorimetric MTS assay in HD human lymphoblasts treated or not with pridopidine for 24 h followed by 6 h incubation with H$_2$O$_2$ (three independent experiments). H$_2$O$_2$ reduces cell viability to ~50%. Pridopidine treatment significantly increases cell viability.

Statistical significance: *p<0.05, p<0.01, *p<0.001, ****p<0.0001 by Kruskal Wallis test followed by Dunn multiple comparison test. No statistical significance was observed between WT basal vs. YAC128 pridopidine treated conditions (in FIGS. 4B and 4C). ns=non-significant.

FIGS. 5A-5H. Pridopidine reduces oxidative challenge-induced ROS production and impaired expression of Nrf2/ARE genes in HD cells.

FIG. 5A. Representative image of cortical and striatal YAC128 neurons treated or not with 1 µM pridopidine, MitoPY1 fluorescence probe was used to measure Mitochondrial $H_2O_2$ levels. Mitochondrial $H_2O_2$ levels were recorded before (at t=14 minutes) and after (t=30 minutes) Antimycin A (a mitochondrial complex III inhibitor; AA, 2 μM), as indicated (considering ~20 cells/condition for St neurons and ~10 cells/condition for Ct neurons from four independent cultures). Scale bar=30 μM.

FIG. 5B. Quantification of mitochondrial $H_2O_2$ levels in cortical neurons. Mitochondrial $H_2O_2$ levels are significantly increased in Y128 neurons in response to Ant A administration, indicating that these cells create more ROS. Pridopidine 1 μM significantly reduces mitochondrial $H_2O_2$ levels back to WT levels.

FIG. 5C. Quantification of mitochondrial $H_2O_2$ levels in striatal neurons. Pridopidine 0.1 and 1 μM significantly reduce Y128 mitochondrial $H_2O_2$ levels back to WT levels.

Figure 5D:
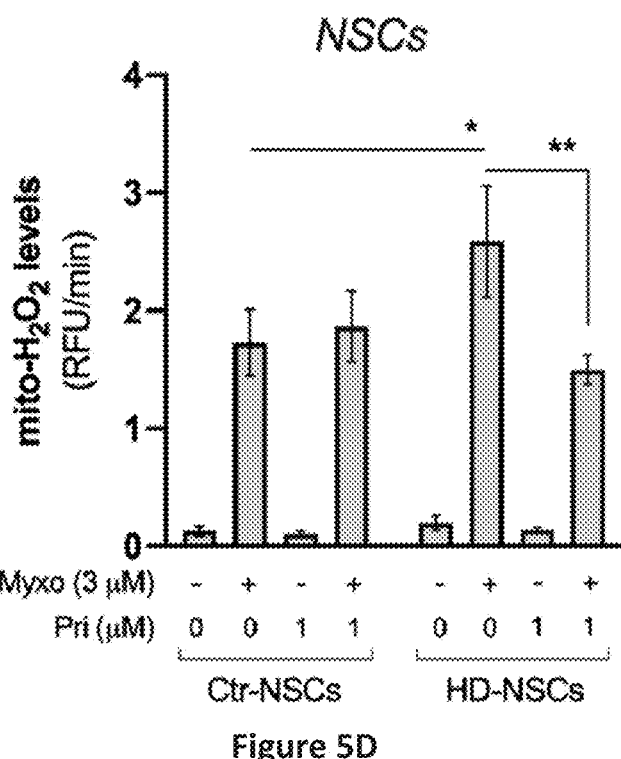

FIG. 5D. Quantification of mitochondrial $H_2O_2$ in human NSCs treated with 1 μM pridopidine for 24 h in the presence or absence of the mitochondrial complex III inhibitor myxothiazol (Myxo, 3 μM) as indicated in the graph (four independent experiments). HD NSCs produce more mitochondrial $H_2O_2$ in response to Myxo. Pridopidine 1 μM rescues this effect.

Figure 5E:
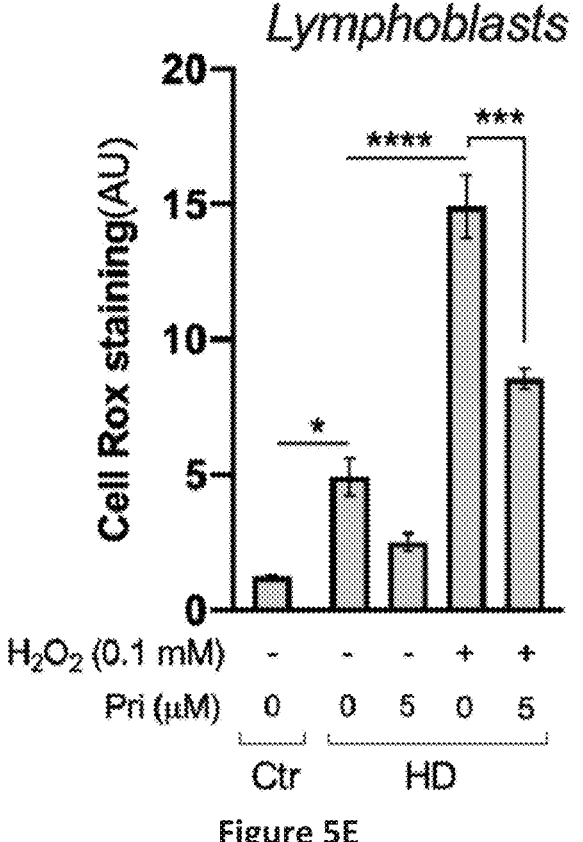

FIG. 5E. Quantification of ROS levels by the oxidative stress detector CellRox in HD lymphoblasts treated with 0.1 mM $H_2O_2$ for 6 h followed by 5 μM pridopidine treatment for 24 h, where indicated (four independent experiments). ROS levels are significantly increased in HD lymphoblasts compared to control healthy cells. Pridopidine significantly reduces ROS levels.

Figure 5F:
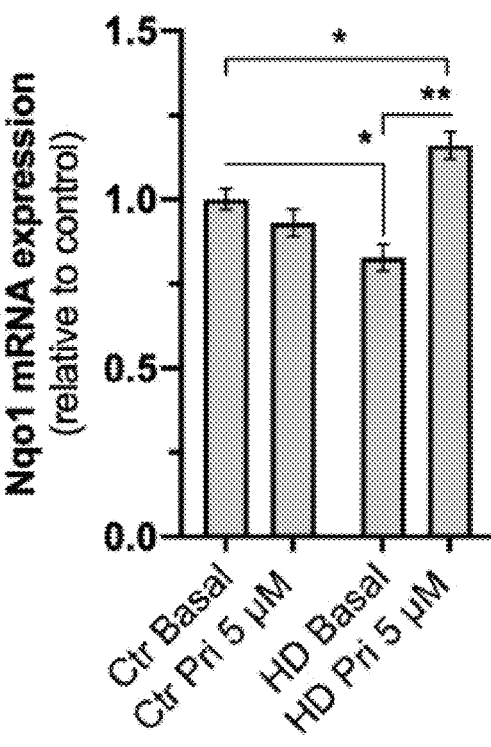
Figure 5G:
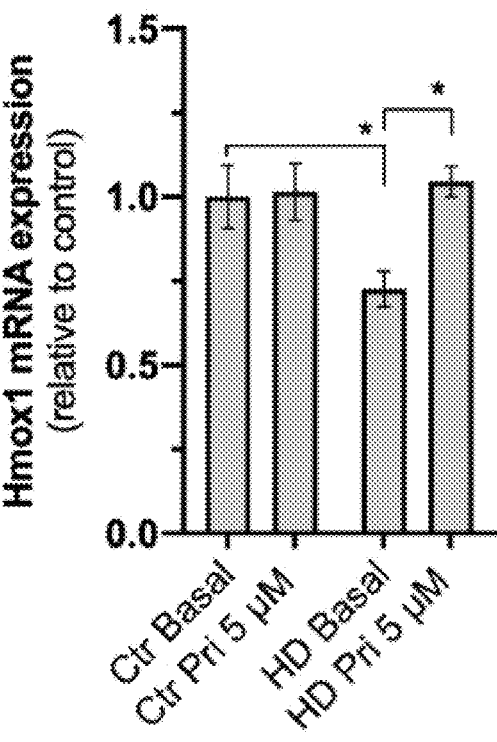
Figure 5H:
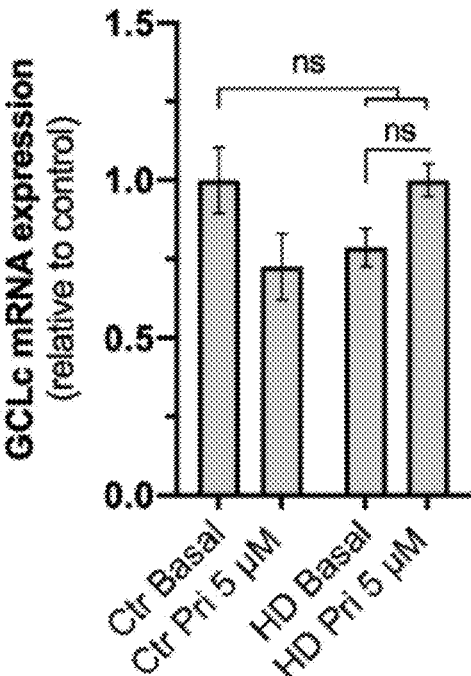

FIGS. 5F-5H. Nrf2 protein levels are increased in WT cells in response to oxidative insult, but not in HD cells. The expression of antioxidant genes lying downstream to Nrf2, Ngo1 (FIG. 5F), Hmox1 (FIG. 5G), and GCLc (FIG. 5H) were evaluated by qPCR (three independent experiments) and show a decrease in HD lymphoblasts. Pridopidine 5 μM treatment for 24 hours significantly restores the levels of Nqo1 and Hmox1. Pridopidine treatment also increases GCLc levels in HD cells.

Statistical significance: *$p<0.05$, $p<0.01$, $p<0.0001$ by 2-way ANOVA followed by Tukey's multiple comparison test. In E, I-K, *$p<0.05$, $p<0.01$, *$p<0.001$, ****$p<0.0001$ by Kruskal Wallis test followed by Dunn multiple comparison test. ns=non-significant.

FIGS. 6A-6C. Pridopidine effects on mitochondrial function are mediated by the S1R. Representative image (FIG. 6A) and quantification (FIG. 6B) of western blot confirming S1R genetic silencing (~83%) in HD lymphoblasts.

FIG. 6C. Quantification of MMP by TMRE signal in control and S1R-silenced HD lymphoblasts treated or not with $H_2O_2$ and pridopidine (5 μM, 24 h, n=4). Pridopidine treatment increases mitochondrial membrane potential in WT cells, but not in cells in which the S1R has been silenced. This indicates that the effects of pridopidine are mediated by the S1R.

Statistical significance: ****$p<0.0001$ by Kruskal Wallis test followed by Dunn multiple comparison test.

FIGS. 7A-7J. Early pridopidine treatment normalizes mitochondrial complex activity and $H_2O_2$ production in isolated YAC128 striatal mitochondria.

Figure 7A:
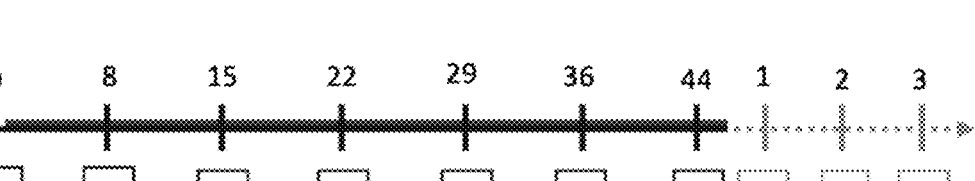

FIG. 7A. Schematic representation of the in vivo/ex vivo experimental design: mice were treated with vehicle or pridopidine for 45 days anticipated and followed by rotarod test (R); animal's weight (W) was measured once a week during the time of treatment and pridopidine concentration adjusted. 24 h after treatment conclusion, striatum was dissected, and mitochondria isolated for functional analyses. Rotarod motor test was performed before (FIG. 7B) and after (FIG. 7C) the treatment and consisted of three trails on an accelerating rotarod from 5 to 40 rpm over 5 minutes, scores were averaged. Pridopidine treatment increases latency to fall in YAC128 mice to levels similar to WT mice.

Figure 7B:
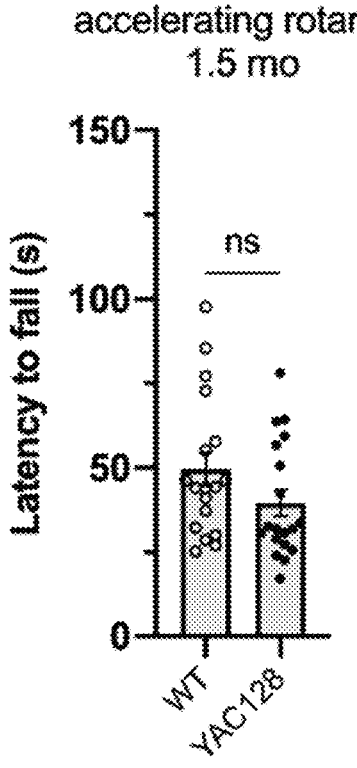
Figure 7B:
Figure 7C:
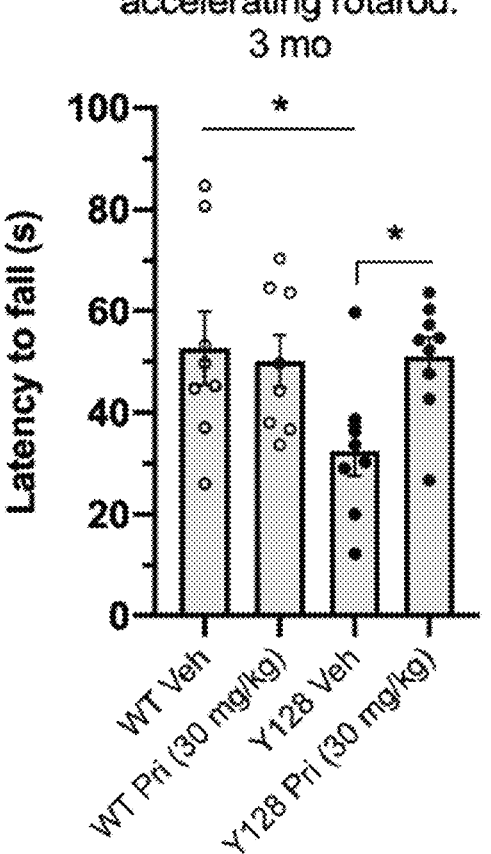
Figure 7D:
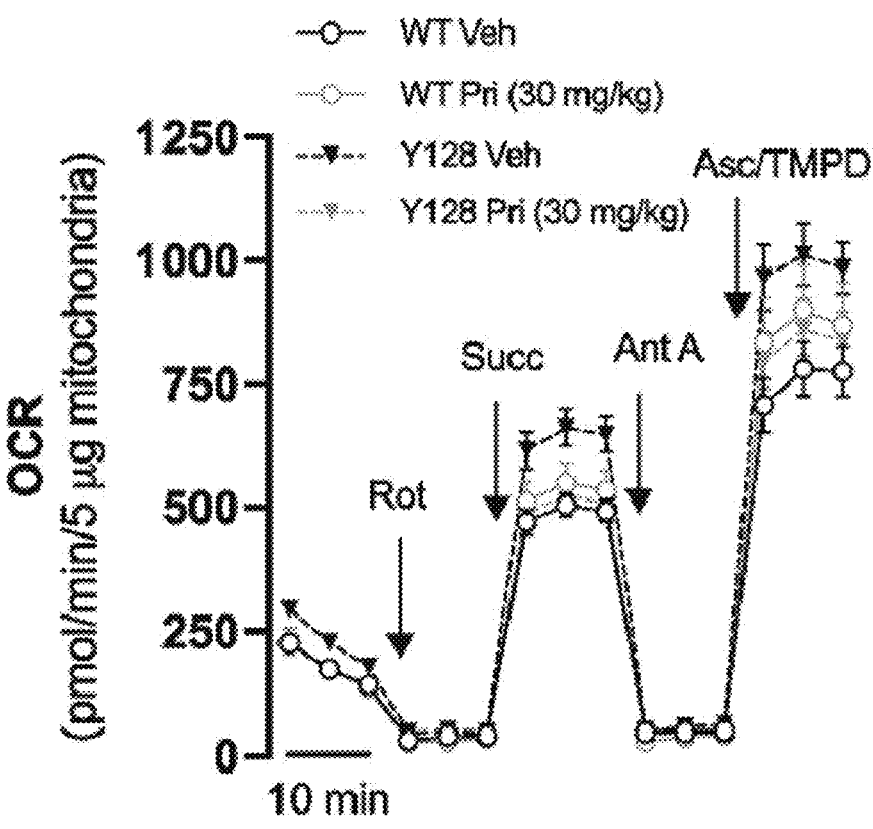

FIG. 7D. Representative graph of electron flow measurement in striatal mitochondria isolated from vehicle- or pridopidine-treated WT and YAC128 mice using a Seahorse apparatus. Mitochondrial complex inhibitors and substrates, 2 μM rotenone, 10 mM succinate, 4 μM antimycin A and 1 mM ascorbate/100 mM TMPD, were sequentially injected to calculate mitochondrial complex II (FIG. 7E), complex III (FIG. 7F) and complex IV (FIG. 7G) activities, respectively. OCR is increased in Y128 mitochondria response to inhibition of complexes II, III and IV. Pridopidine treatment rescues this effect in response to inhibition of complexes II and III and shows a similar decreasing trend in response to inhibition of complex IV.

Figure 7E:
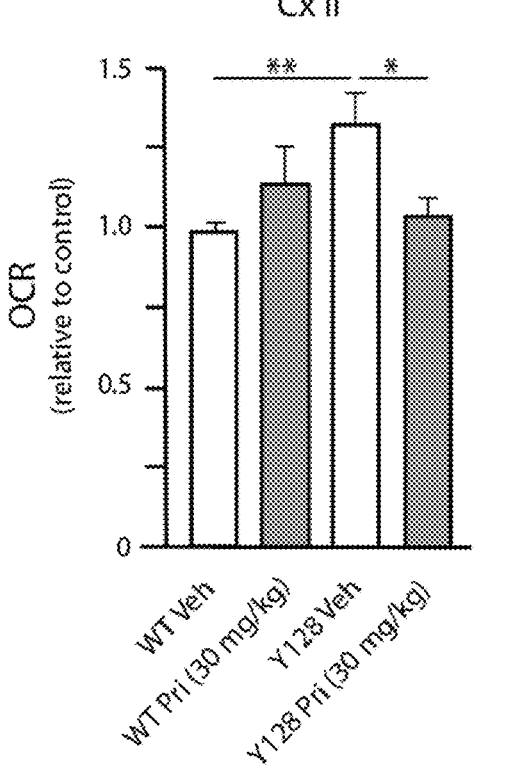
Figure 7H:
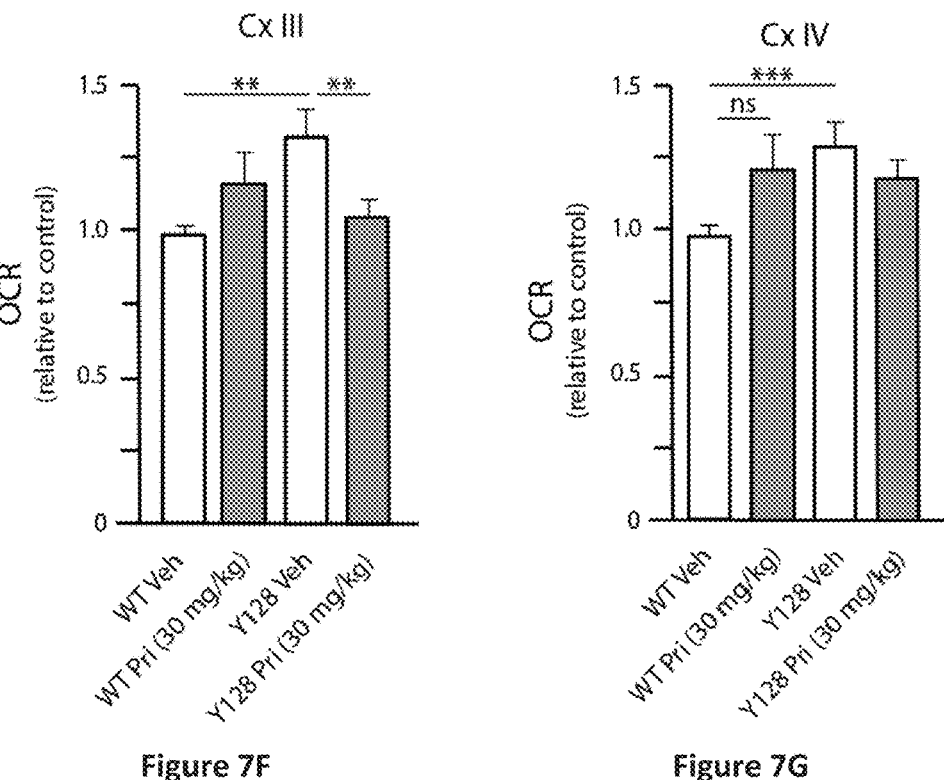
Figure 7H:
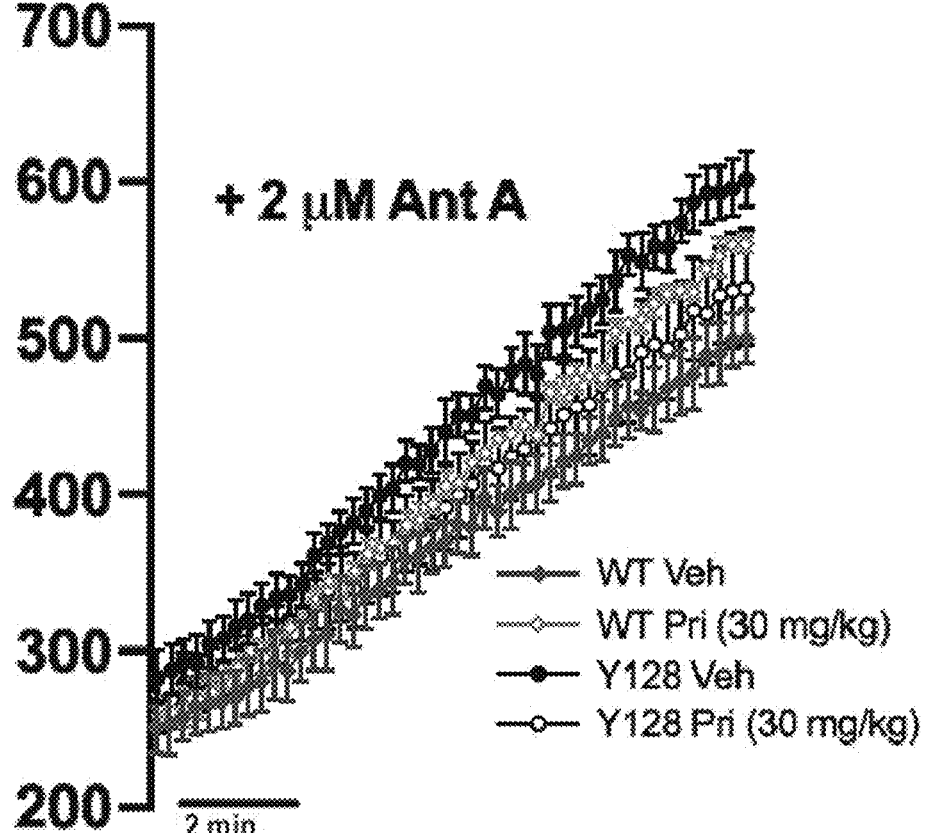

FIG. 7H. Representative graph of mitochondrial $H_2O_2$ levels. Mitochondrial levels of $H_2O_2$ were measured using Amplex Red probe. The fluorescence of the Amplex Red probe was evaluated for 10 minutes before (FIG. 7I) and after (FIG. 7J) inhibition of mitochondrial complex III with antimycin A (2 μM). In FIG. 7H, graph shows time-dependent changes in fluorescence after adding Ant A. $H_2O_2$ levels are significantly higher in Y128 neurons both in basal and Ant A induced conditions. Pridopidine treatment reduces $H_2O_2$ levels in Y128 neurons (not statistically significant).

Statistical significance:*$p<0.05$, **$p<0.01$ by non-parametric Kruskal-Wallis test followed by Dunn multiple comparison test. ns=non-significant.

Figure 8A:
Figure 8B:
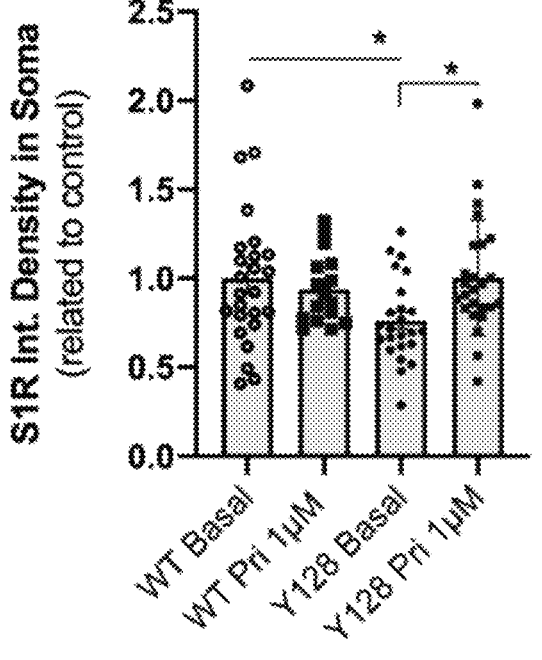
Figure 8C:
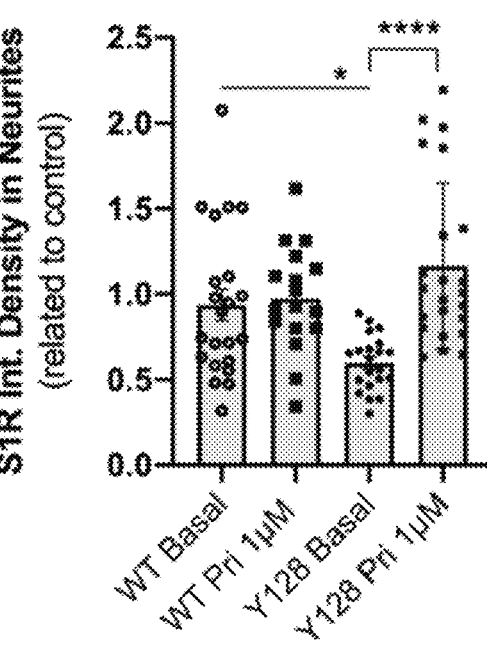

FIGS. 8A-8C. Pridopidine rescues S1R total levels in striatal YAC128 neurons. WT and YAC128 striatal neurons were treated for 24 h with 1 μM pridopidine. S1R, in green, was labelled using a specific antibody and Hoechst, in blue, was used to label the nucleus. FIG. 8A: Representative images of S1R expression in striatal neurons Representative image of a confocal single cell image. S1R total levels were quantified for soma (cell body) (FIG. 8B) and neurites (FIG. 8C) using ImageJ software. S1R levels are reduced in both soma and neurites. Pridopidine treatment significantly increases S1R levels in YAC 128 neurons in both the soma and the neurite. Data are from 3 independent primary cultures; each point represents a neuron. Scale bar=5 μm.

Statistical significance: *$p<0.05$, **$p<0.0001$ by non-parametric Kruskal-Wallis test.

Figure 9:
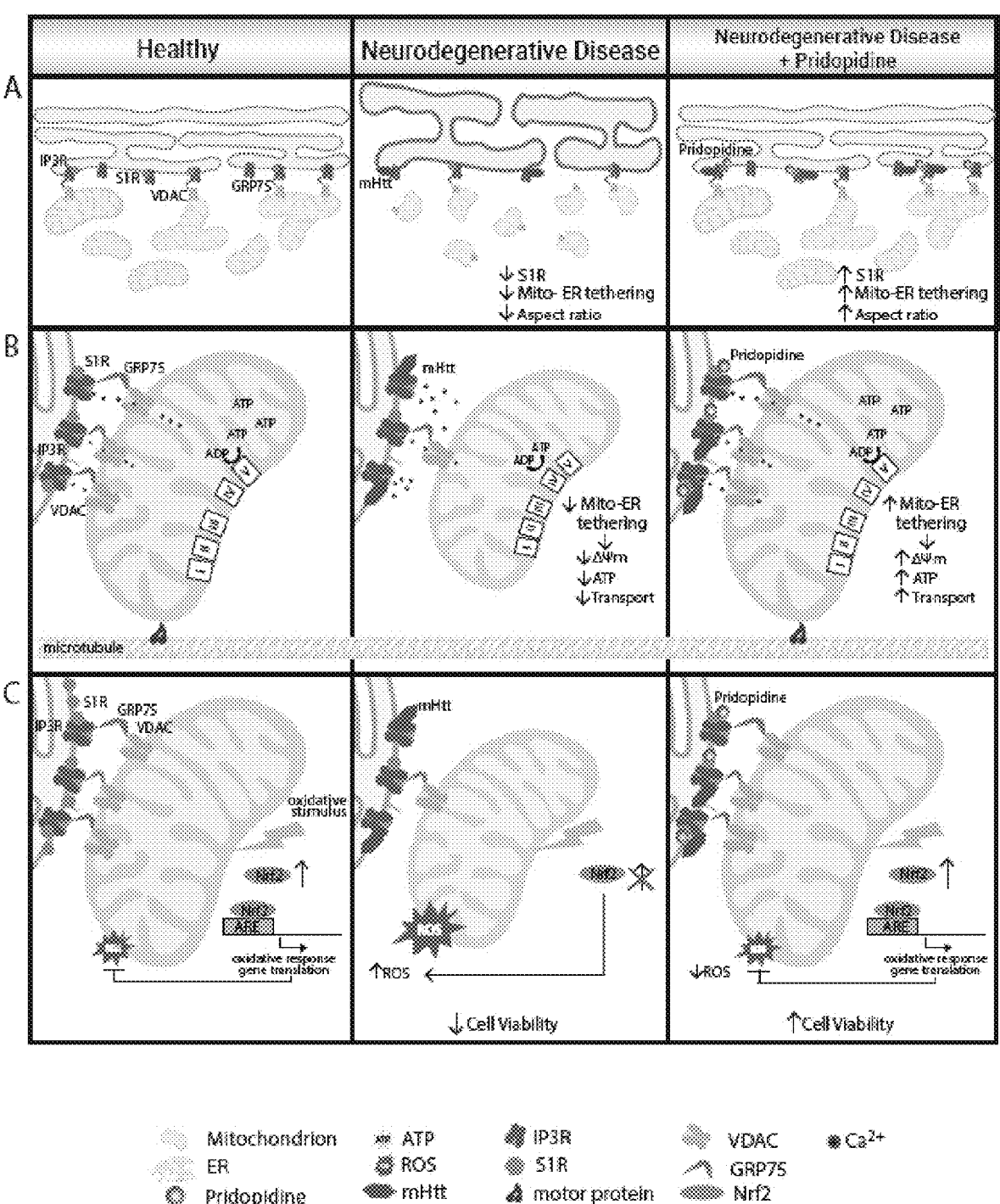

FIG. 9: Pridopidine restores multiple mitochondrial processes disrupted in neurodegenerative diseases. Row A (top). Mitochondria-ER tethering is essential for mitochondrial health. In healthy cells, mitochondria-ER tethering is facilitated via S1R stabilization of the tethering complex consisting of $IP_3R$, GRP75 and VDAC (Bernard-Marissal et al. 2015), which maintains the balance between mitochondrial fission and fusion (left). In neurodegenerative diseases such as HD, mHTT binds to the $IP_3R$ at the ER membrane, which may disrupt these contacts and lead to a reduction in mitochondria-ER tethering, and influence mitochondrial fission (fragmented, round mitochondria) (center). ER also presents a swollen structure. Pridopidine activation of the S1R increases mitochondria-ER tethering and restores mitochondrial and ER morphology (right). Row B (middle). Mitochondria-ER tethering regulates $Ca^{2+}$ flux to the mitochondria via the $IP_3R$ (left). As a result of the disruption in mitochondria and ER communication in neurodegenerative diseases, mitochondria bioenergetics is compromised, as observed by decreases in MMP (ΔΨ) and ATP production (center); concomitantly, a reduction in bidirectional mitochondrial transport is observed. Pridopidine treatment increases mitochondrial membrane potential, ATP production and mitochondrial trafficking (right). Row C (bottom). In healthy cells oxidative insult (i.e. $H_2O_2$) enhances Nrf2 levels, leading to upregulation of ARE genes as a defense mechanism (left). This response, necessary for cell survival, is abrogated in HD cells (center). Pridopidine treatment restores the Nrf2-ARE response to oxidative stress and rescues cell viability (right).

Figures 10A, 10B, 10C, 10D, 10E:
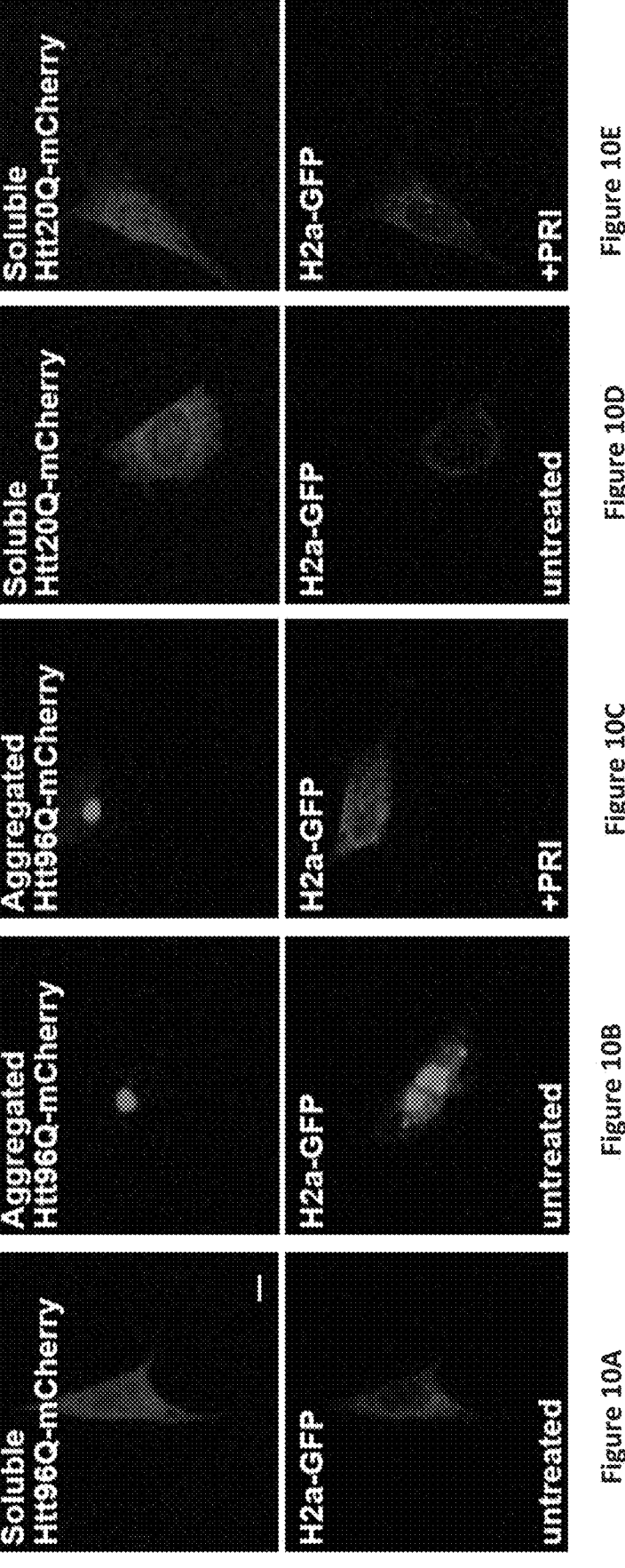

FIGS. 10A-10E. Pridopidine reduces early mHtt-induced ER stress in a dose-dependent manner. Histone 2a (H2a)-GFP, which forms aggregates in response to ER stress, was transiently co-expressed with wild-type (WT) Htt20Q-mCherry or mutant Htt96Q-mCherry (exon 1) in STHdh$^{Q7/7}$ cells. Cells were treated without or with increasing concentrations of pridopidine starting 4 h post-transfection and imaged in a confocal microscope 24 h post-transfection. Representative images are shown of cells with non-aggregated Htt96Q-mCherry (FIG. 10A), with aggregated Htt96Q-mCherry in the absence (FIG. 10B) or in the presence of 150 µM pridopidine (PRI) (FIG. 10C) or with Htt20Q-mCherry in the absence (FIG. 10D) or in the presence of pridopidine (FIG. 10E). Bar=10 µm. In cells transfected with WT Htt20Q-mCherry, both Htt and H2a GFP are dispersed throughout the cell (FIG. 10A). In cells with large mHtt96Q-mCherry aggregates, H2a-GFP is also aggregated indicating increased ER stress in the cell (FIG. 10B). Pridopidine treatment leads to H2a-GFP dispersion throughout the cell, indicating that pridopidine ameliorates ER stress. In cells transfected with mHtt96Q-mCherry that does not form large aggregates, H2a-GFP does not aggregate either (FIG. 10D), and pridopidine does not affect its dispersion throughout the cell (FIG. 10E).

Figure 10F:
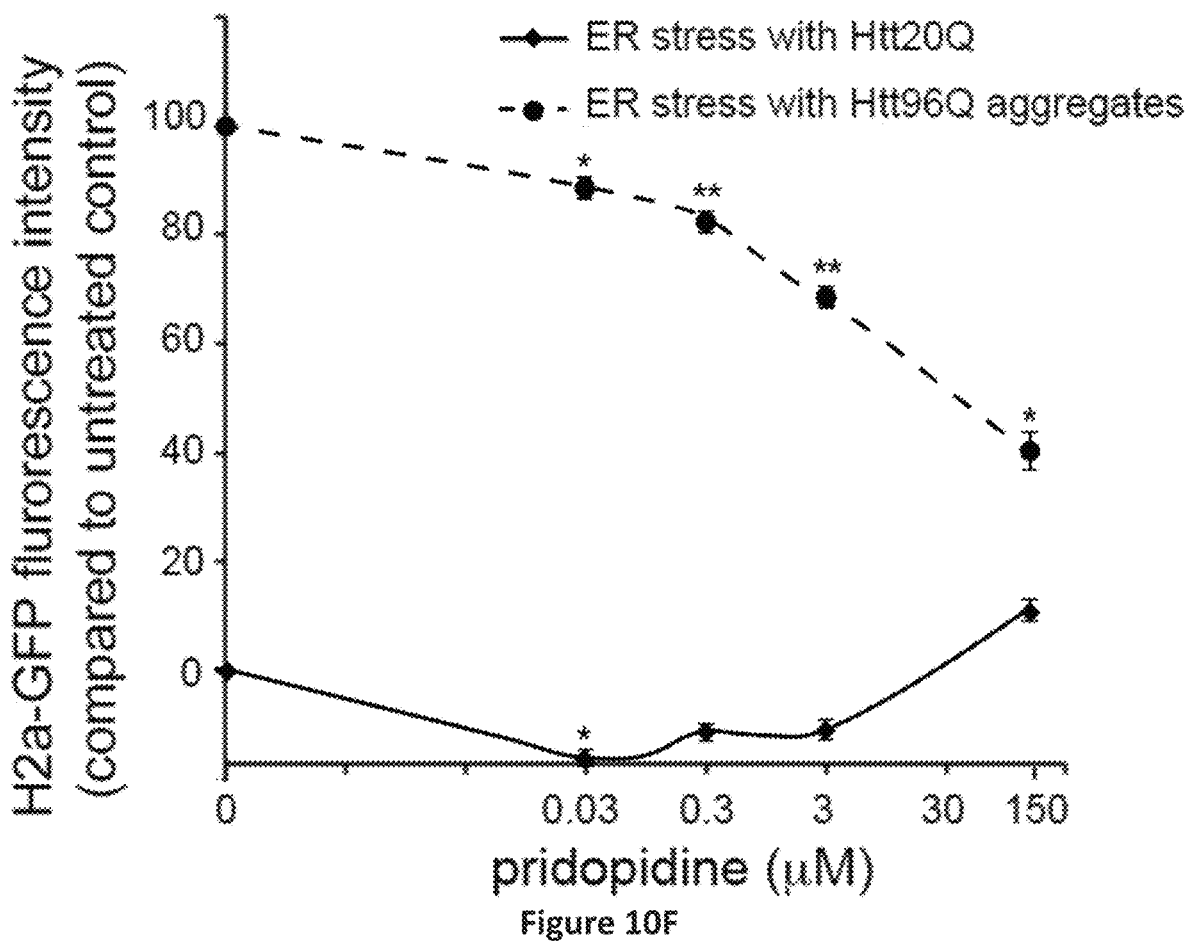

FIG. 10F. Images of individual cells (~150 cells per experiment) with Htt96Q-mCherry aggregates or with Htt20Q-mCherry were quantified compared to untreated cells with and without aggregates. For comparative purposes, 100% represents H2a-GFP relative intensity in untreated cells showing Htt96Q-mCherry aggregates, 0% is H2a-GFP relative intensity in untreated cells without Htt96Q-cherry aggregates. Pridopidine demonstrates a dose-dependent decrease in ER stress. The graphs are averages of 3 experiments±SE. The asterisks indicate P values compared to untreated, <0.05 (*) and <0.01 (**). Data points without asterisk in this and other figures indicate that the difference is not significant.

Figure 1A:
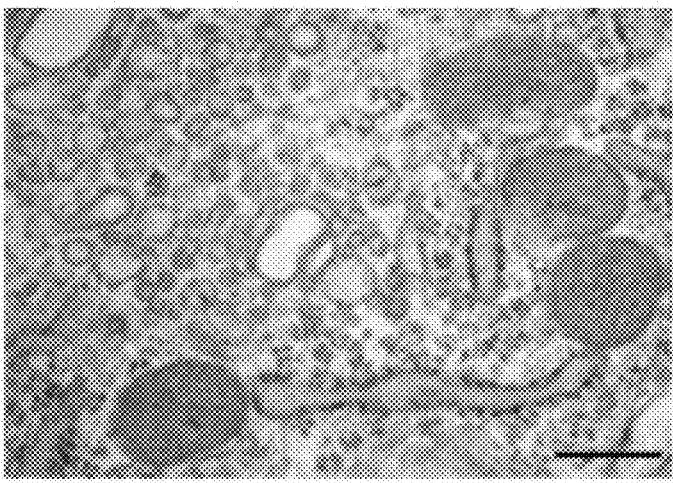
Figure 1A:
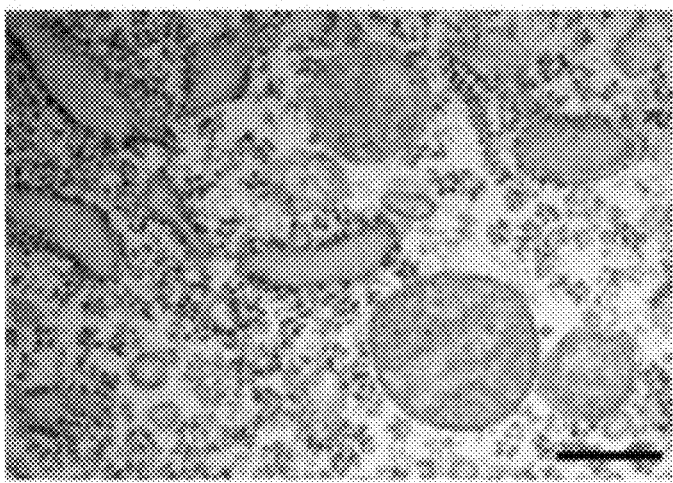
Figure 1A:
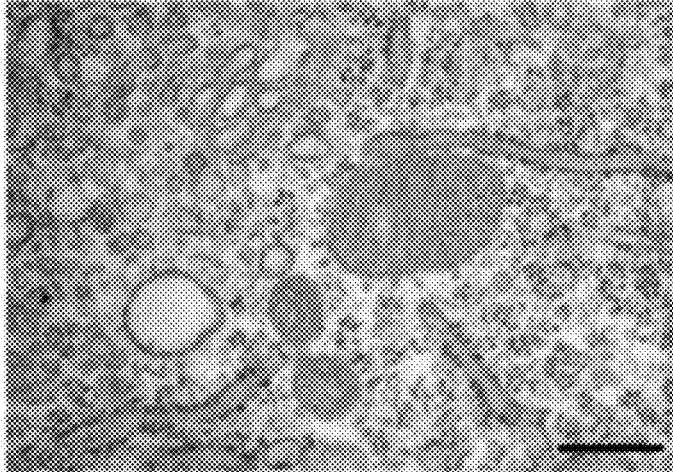
Figures 11A, 11B:
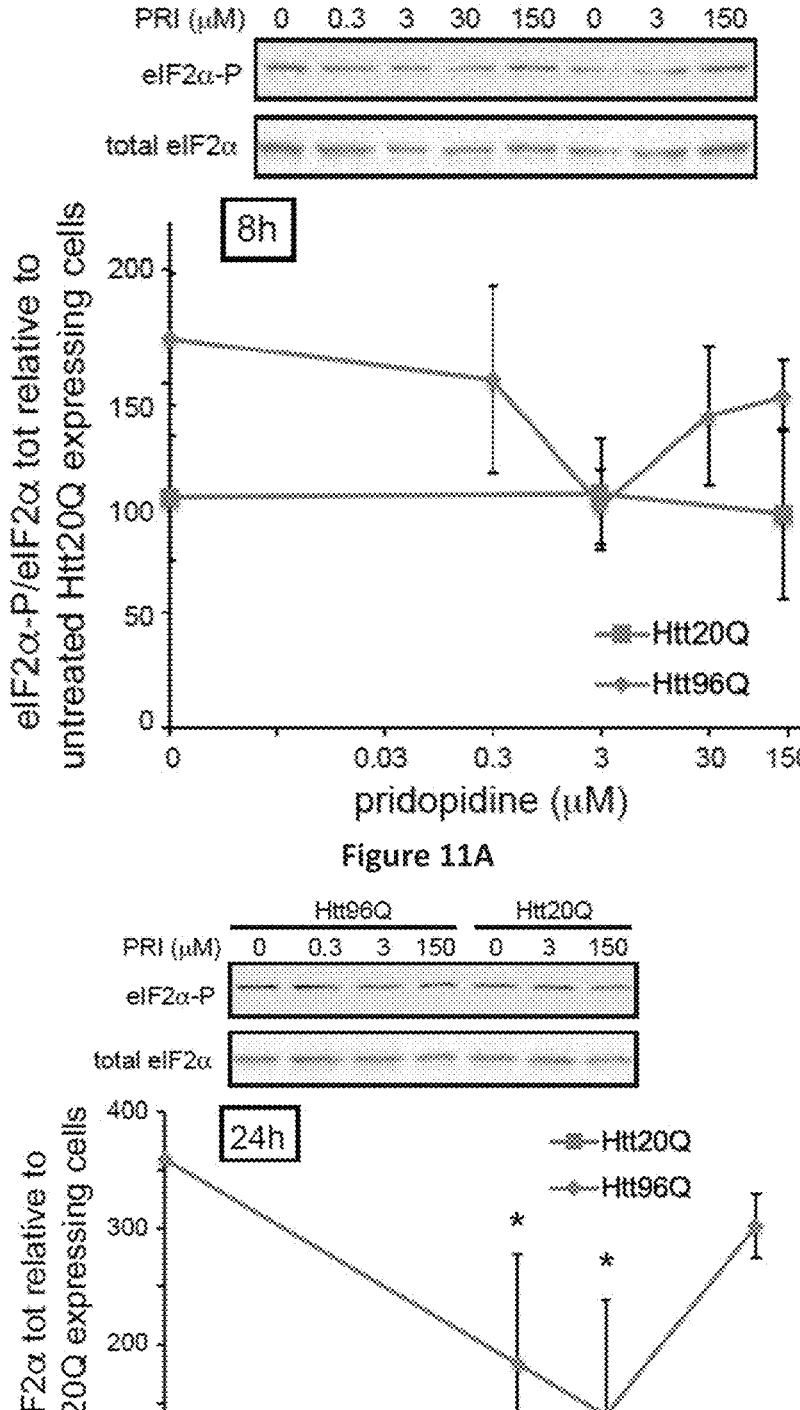
Figure 11C:
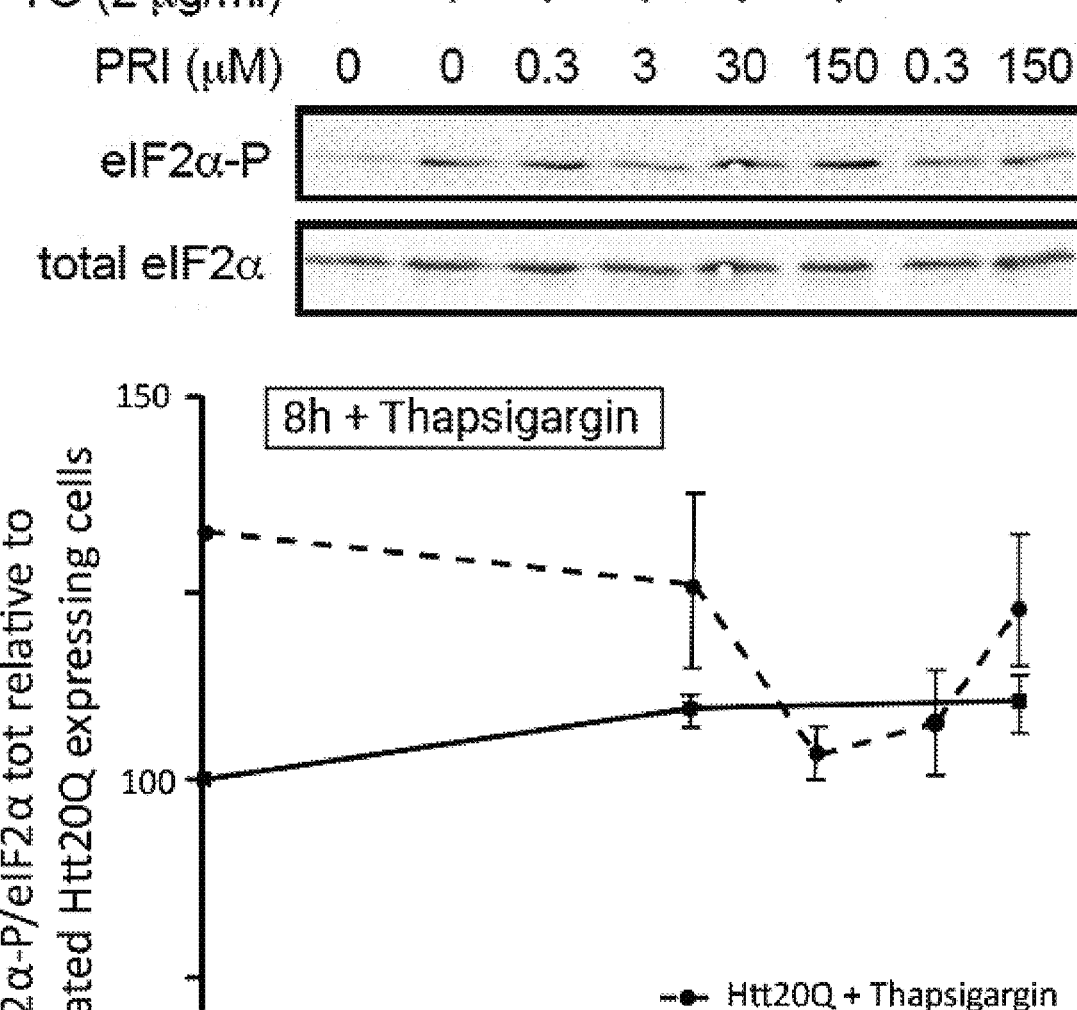

FIGS. 11A-11B. Pridopidine reduces eIF2α phosphorylation in cells expressing Htt96Q. myc-Htt96Q (diamonds) or myc-Htt20Q (squares) were transiently expressed in HEK 293 cells and treated with increasing concentrations of pridopidine. Htt expression and cell incubation with pridopidine were for the indicated times. The ratio of eIF2α-P to total eIF2α was measured by immunoblotting and quantified. FIG. 1A. Pridopidine demonstrates a maximal effect on reducing eIF2α phosphorylation after 8 hours at 3 µM. FIG. 11B. Pridopidine demonstrates a maximal effect on reducing eIF2α phosphorylation after 24 hours at 3 µM. In this and all other figures the graphs show this ratio relative to that in untreated cells expressing Htt20Q (=100), except when indicated, and are averages of 4 experiments (A) and 3 experiments (B) f SD. P values <0.05 (*). FIG. 11C. Similar to FIG. 11A, but with cells expressing myc-Htt20Q treated or not with 2 µg/ml thapsigargin (TG) to induce cell stress. This indicates that pridopidine reduces eIF2α phosphorylation in cases of ER stress not induced by mutant Htt.

Figure 12A:
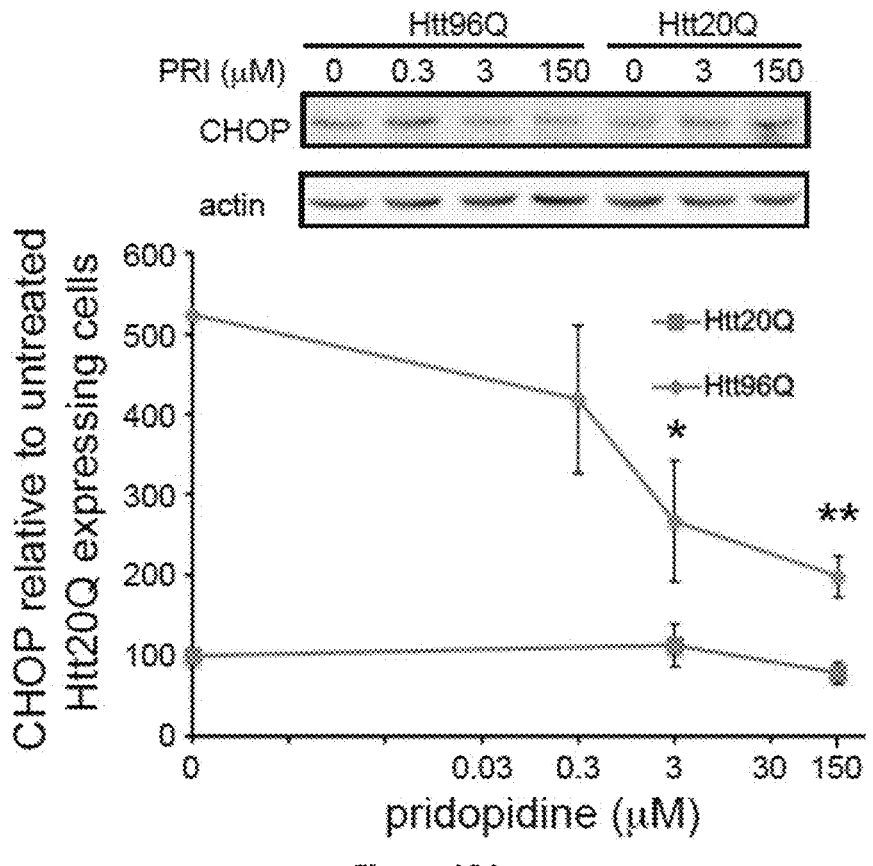
Figure 12B:
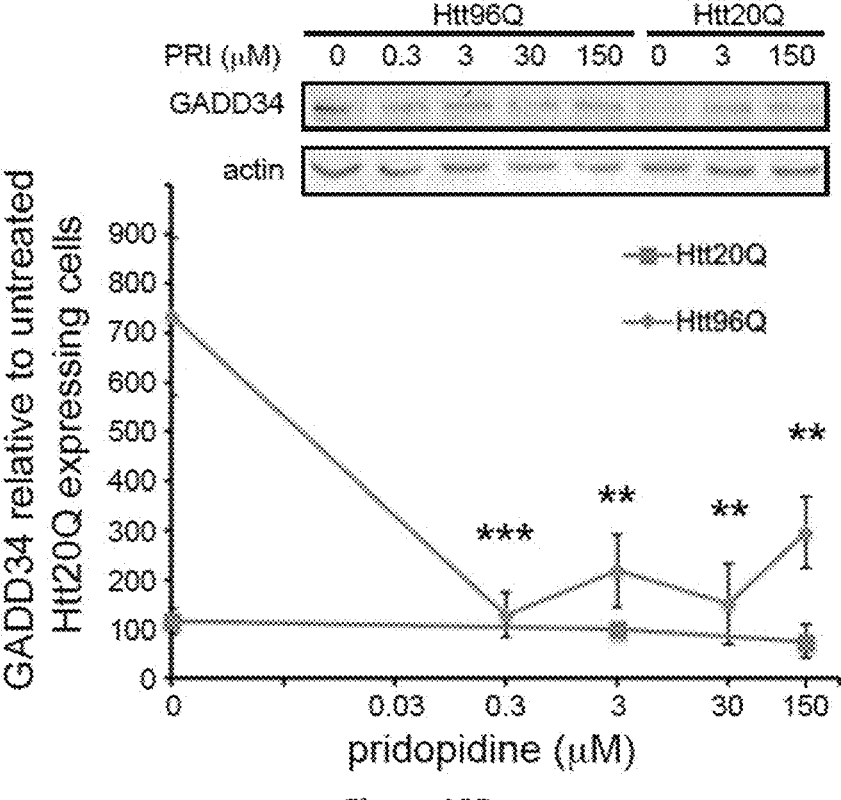
Figure 12C:
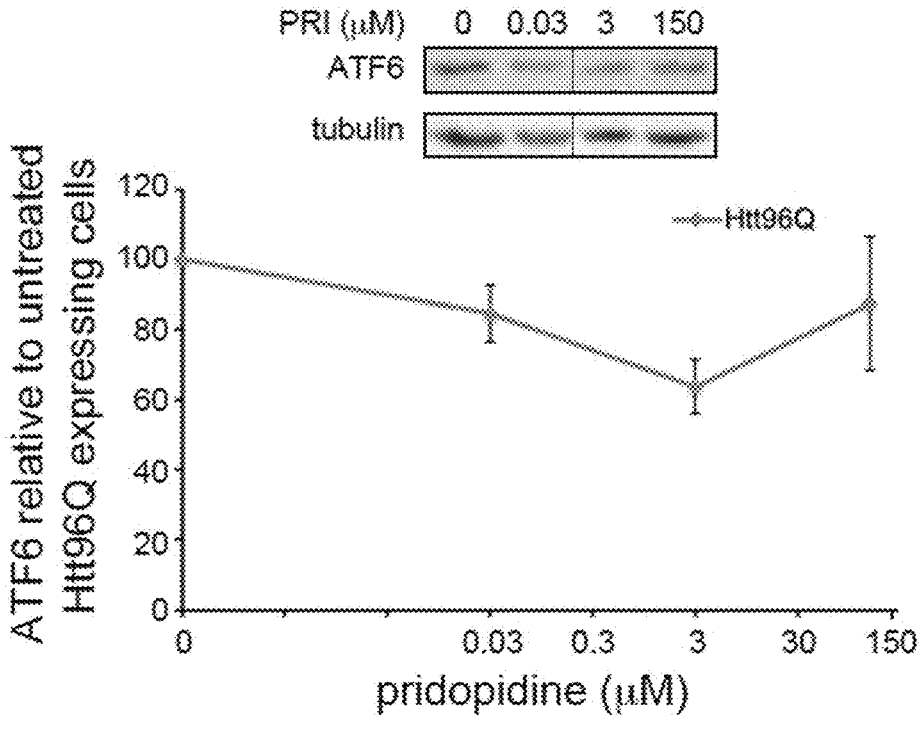

FIGS. 12A-12C. Pridopidine reduces Unfolded Protein Response (UPR) marker levels cells expressing mutant Htt96Q. Cells expressing mutant myc-Htt96Q (diamonds) or WT myc-Htt20Q (squares) were treated with pridopidine for 24 hours. A longer time period (48 h) was evaluated for the late UPR markers, CHOP and GADD34 to see stronger and more significant effects. Immunoblots were reacted with anti-CHOP (FIG. 12A), anti-GADD34 (FIG. 12B) or anti-ATF6 (showing ATF6 cleaved fragment; FIG. 12C), quantified and normalized with anti-actin or anti-tubulin as loading controls. Pridopidine treatment leads to a decrease in all of these UPR markers which are indicators of ER stress downstream to eIF2α phosphorylation.

Figure 12D:
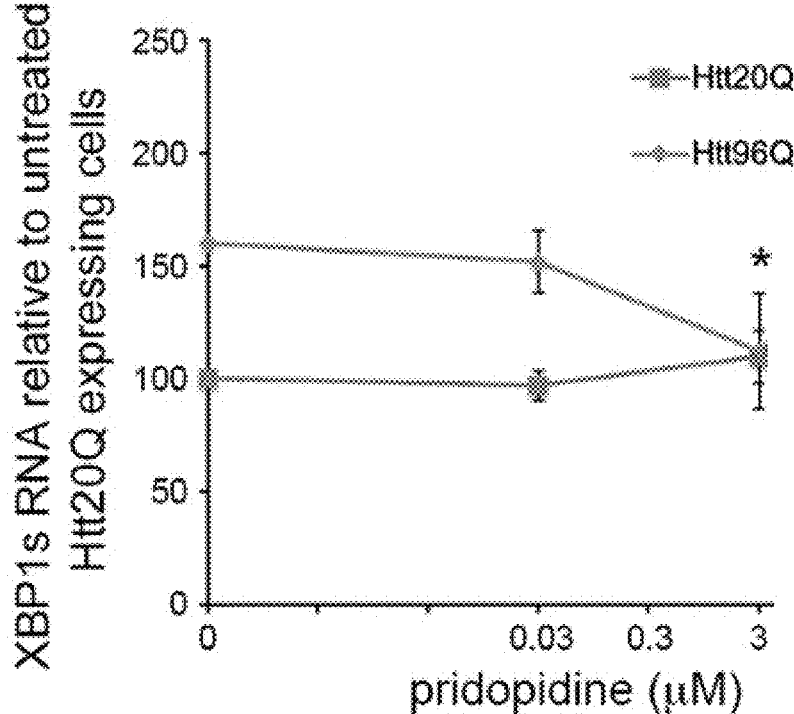

FIG. 12D. For XBP1s, instead of immunoblots, cell lysates were subjected to quantitative real time PCR (qPCR) for XBP1s mRNA, compared to a housekeeping gene, GAPDH. Pridopidine reduces the increased XBP1s mRNA levels in cells expressing mutant Htt96Q. The graphs show values relative to untreated cells expressing WT myc-Htt20Q, except for ATF6, and are averages of 4 independent experiments (A) and 3 independent experiments (B-D)+−SD. The asterisks indicate P values compared to untreated <0.05 (*), <0.01 () and <0.001 (*).

Figure 13A:
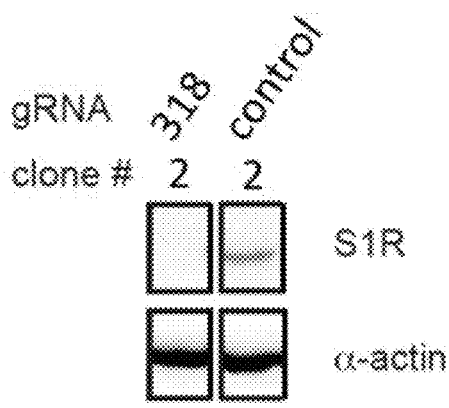
Figure 13B:
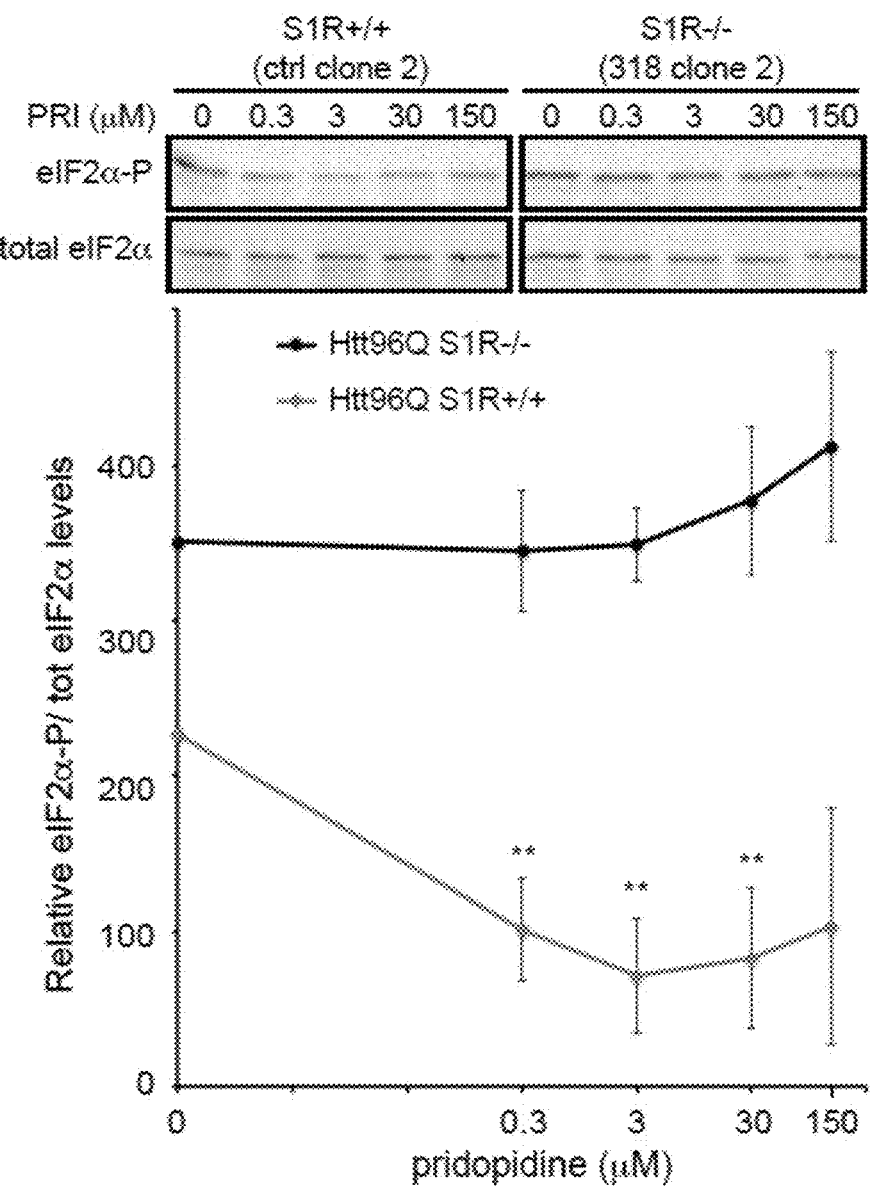

FIGS. 13A-13B. Pridopidine reduction of eIF2α phosphorylation is mediated by the S1R.

FIG. 13A. S1R expression was silenced in HEK293 by CRISPR, using a guide RNA (gRNA) targeting human S1R and a control gRNA Immunoblot with an anti-S1R antibody demonstrates successful silencing of S1R in clone 318-2.

FIG. 13B. Mutant myc-Htt96Q was transiently expressed in a HEK 293 S1R−/− CRISPR clone (318-2) compared to a control clone (ctrl-2). Cells were treated with increasing concentrations of pridopidine for 8 h. S1R silencing induces eIF2α phosphorylation. Pridopidine treatment significantly reduces eIF2α phosphorylation levels, with the maximal effect at 3 µM. The ratio of eIF2α-P to total eIF2α was measured by immunoblotting and quantified. Values are relative to those in the untreated control clone not expressing myc-Htt96Q. The graph is an average of 3 independent experiments+−SD. P values (treated vs. untreated S1R+/+ cells)<0.01 (**).

FIGS. 14A-14D. Pridopidine increases S1R levels and insolubility in the presence of Htt96Q aggregates.

Figure 14A:
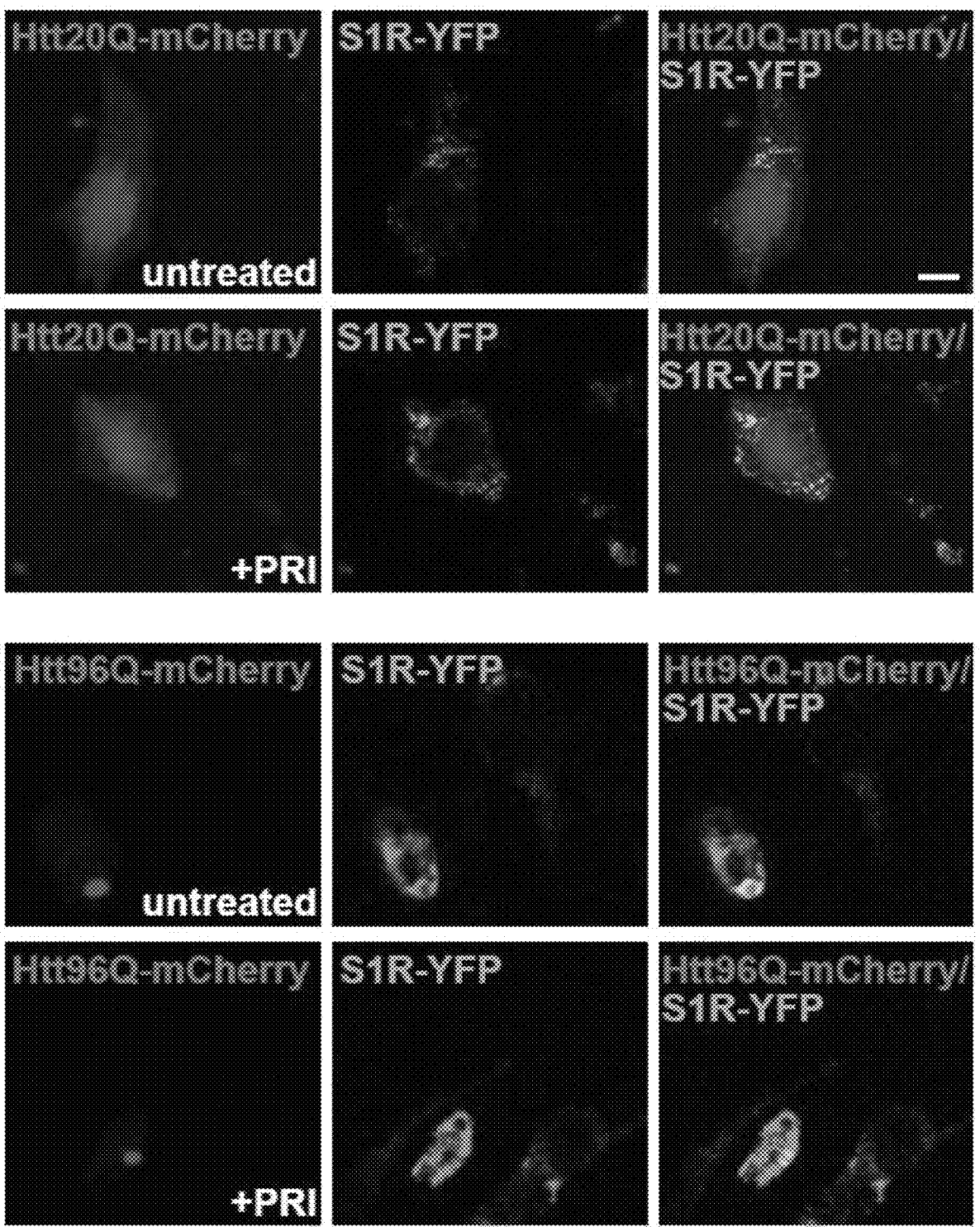

FIG. 14A. S1R-YFP was transiently co-expressed with Htt20Q-mCherry or Htt96Q-mCherry in STHdh$^{Q7/7}$ and cells were treated with 150 µM pridopidine starting 4 h post-transfection or left untreated. Representative images of cells 24 h post-transfection are shown. Bar=10 µm FIG. 14B. Sigma-1R-YFP levels in cells treated with the indicated concentrations of pridopidine, quantified in images of individual cells (~300 cells per experiment) with Htt96Q-mCherry aggregates or Htt20Q-mCherry. 100% represents S1R-YFP relative intensity in untreated cells without Htt96Q-mCherry aggregates. Pridopidine increases S1R-YFP levels in a dose-dependent manner in cells expression mutant Htt96Q. The graph is an average of 3 independent experiments±SE. P value (150 µM vs. 0)<0.05.

Figure 14B:
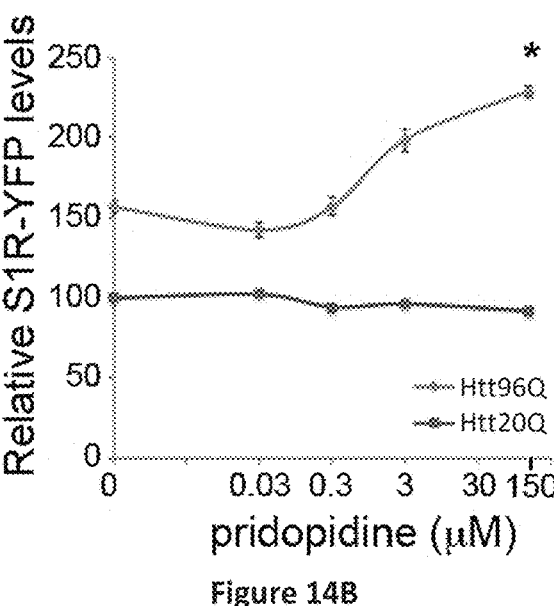
Figure 14C:
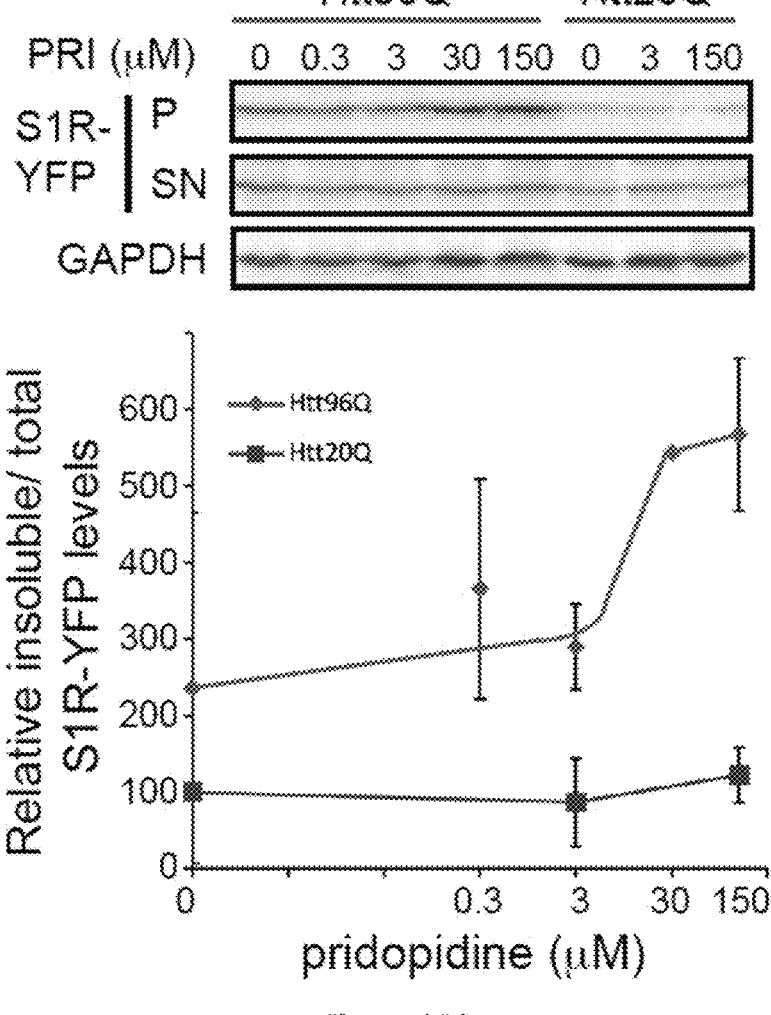
Figure 14D:
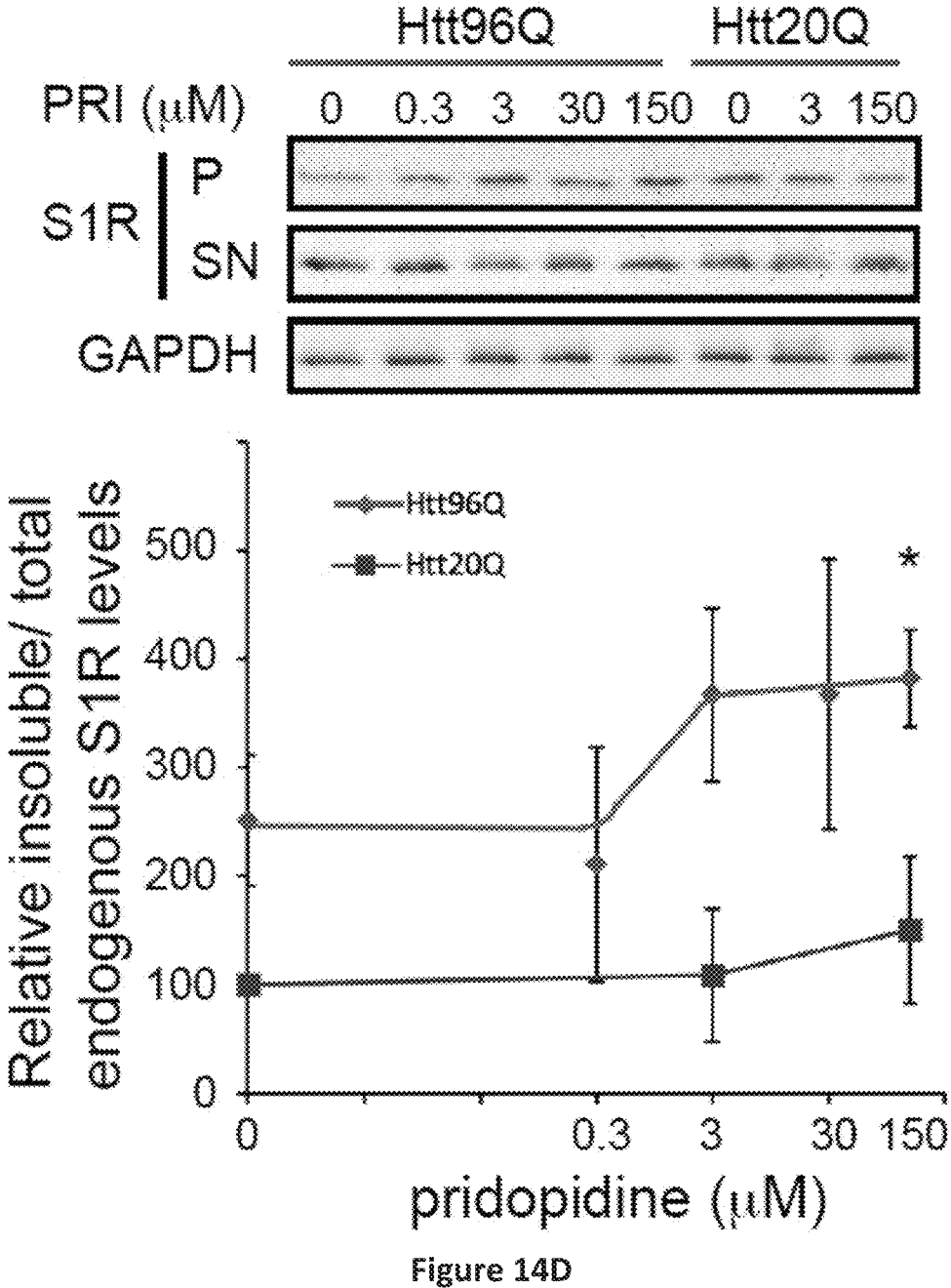

FIG. 14C. Cells were treated with the indicated concentrations of pridopidine for 20 h, starting at 4 h post-transfection. Pridopidine increases the levels of insoluble S1R-YFP in a dose-dependent manner. The graph shows the ratio of the insoluble fraction (P) of S1R-YFP divided by the total (SN+P) and is an average of 3 independent experiments+−SD. FIG. 14D. Similar to the experiment in FIG. 14C but analyzing endogenous S1R. Pridopidine increases levels of insoluble endogenous S1R. Average of 3 independent experiments+−SD. P value (150 µM vs. 0)<0.05.

Figure 15A:
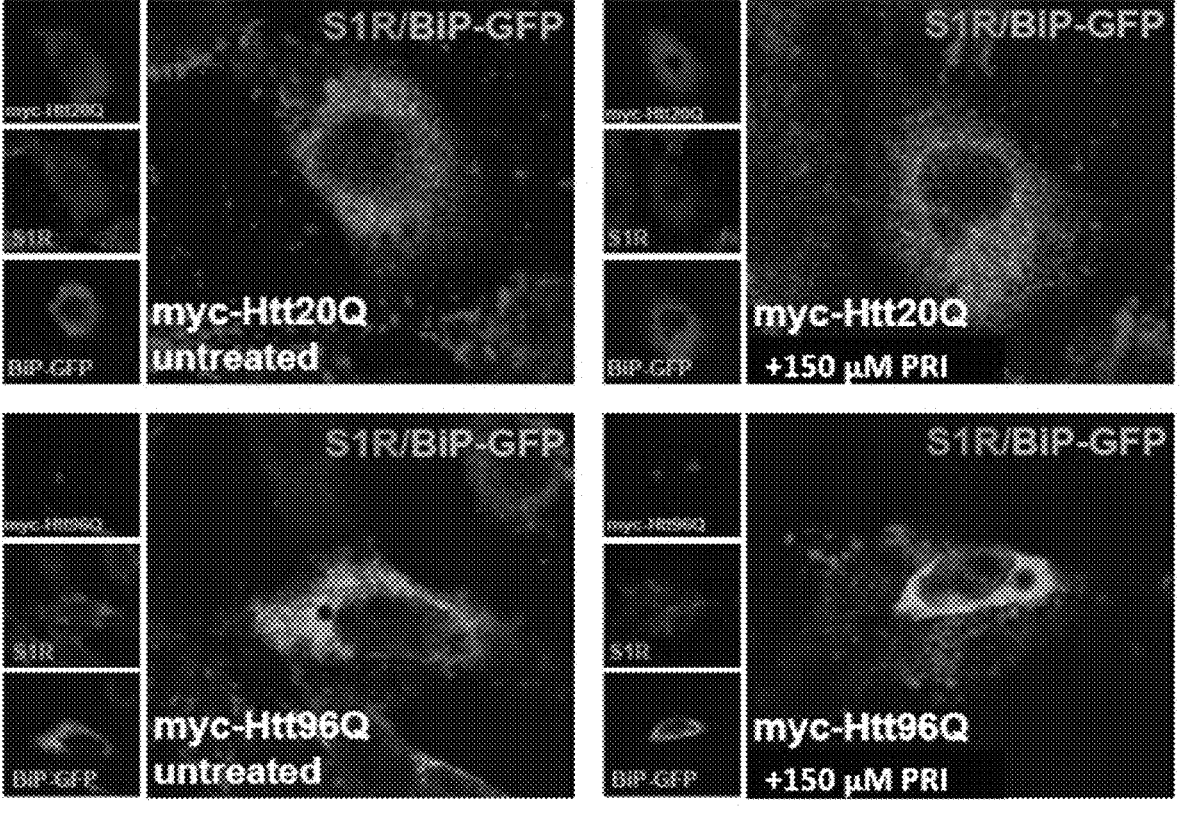
Figure 15A:
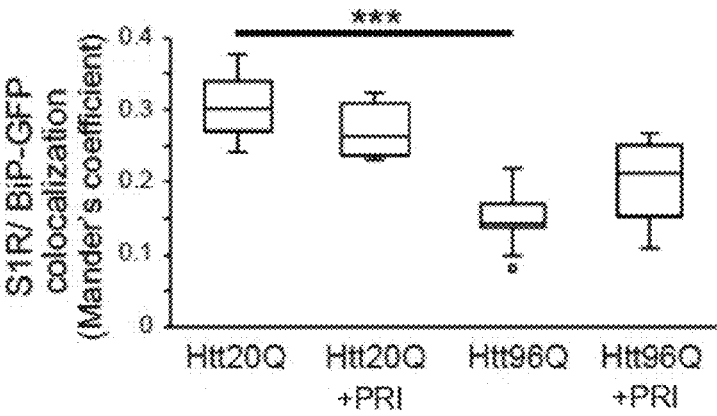
Figure 15B:
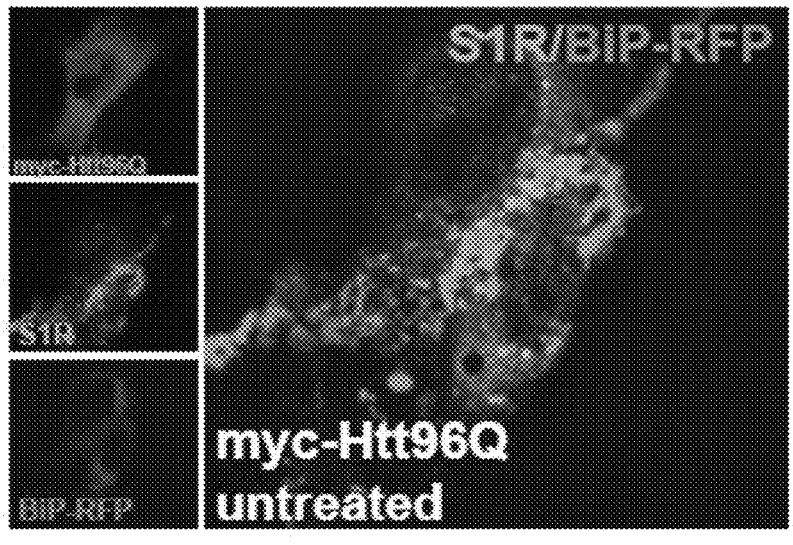
Figure 15B:
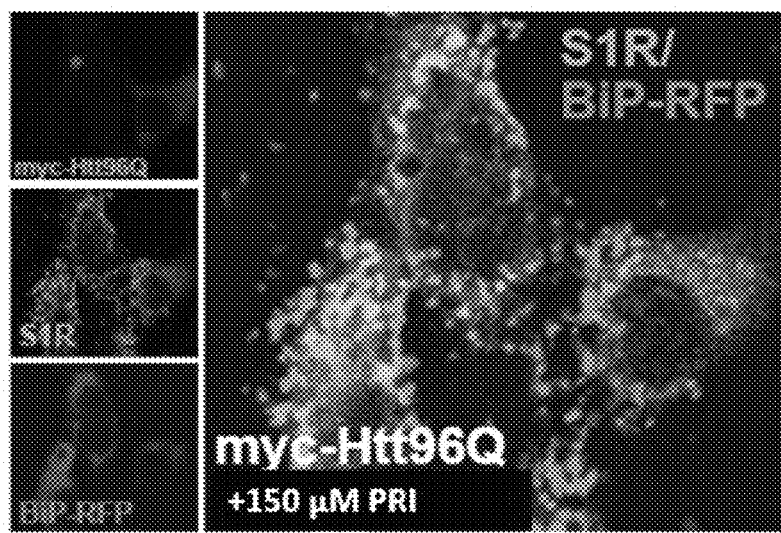
Figure 15B:
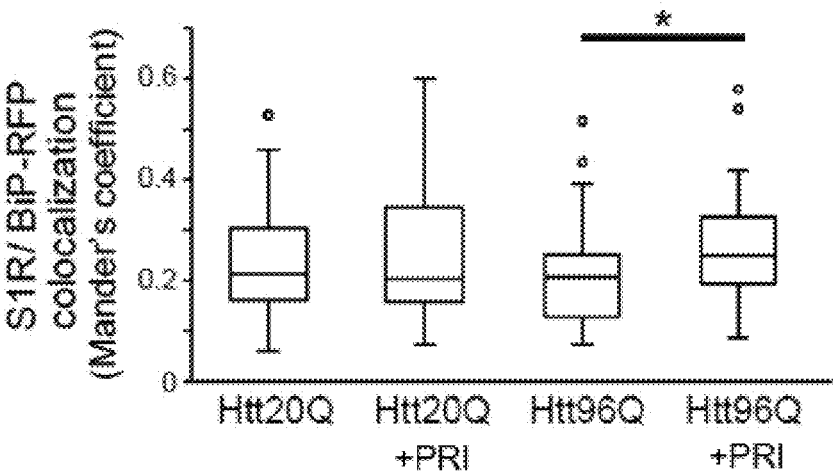

FIGS. 15A-15B. Pridopidine restores S1R colocalization with BiP in the presence of Htt96Q-cherry aggregates.

Colocalization of S1R and mitochondria was assessed in NIH 3T3 cells expressing WT myc-Htt20Q or mutant myc-Htt96Q. Cells were then fixed, permeabilized and reacted with mouse anti-myc and rabbit anti-S1R. Images were pseudo-colored to better visualize the colocalization of S1R and MitoTracker.

FIG. 15A. The colocalization of S1R to the ER was evaluated with staining for the ER marker BiP-GFP. Samples were treated with 150 μM pridopidine or left untreated, as indicated. Mutant Htt96Q causes a significant decrease in the colocalization of S1R and BiP. Pridopidine shows a trend towards increasing colocalization. Goat anti-mouse IgG-Dylight 549 and goat anti-rabbit IgG-Dylight 650 were used in this case. The graph below is a box plot of Mander's coefficients, for the colocalization of S1R and BiP-GFP in cells expressing myc-Htt20Q or myc-Htt96Q with or without pridopidine treatment (n=25 cells). Circles indicate mild outliers (<3×IQR).

FIG. 15B. Similar to FIG. 15A, but in this case BiP-RFP was used instead of BiP-GFP and using goat anti-mouse IgG-Cy2 and goat anti-rabbit IgG-Dylight 650. Mutant Htt96Q causes a significant decrease in the colocalization of S1R and BiP. Pridopidine shows a significant increase in colocalization. 3 independent experiments (~50 cells in each). P values: not significant (NS), <0.05 (*), <0.001 (***). Bars in images=10 μm.

Figure 16A:
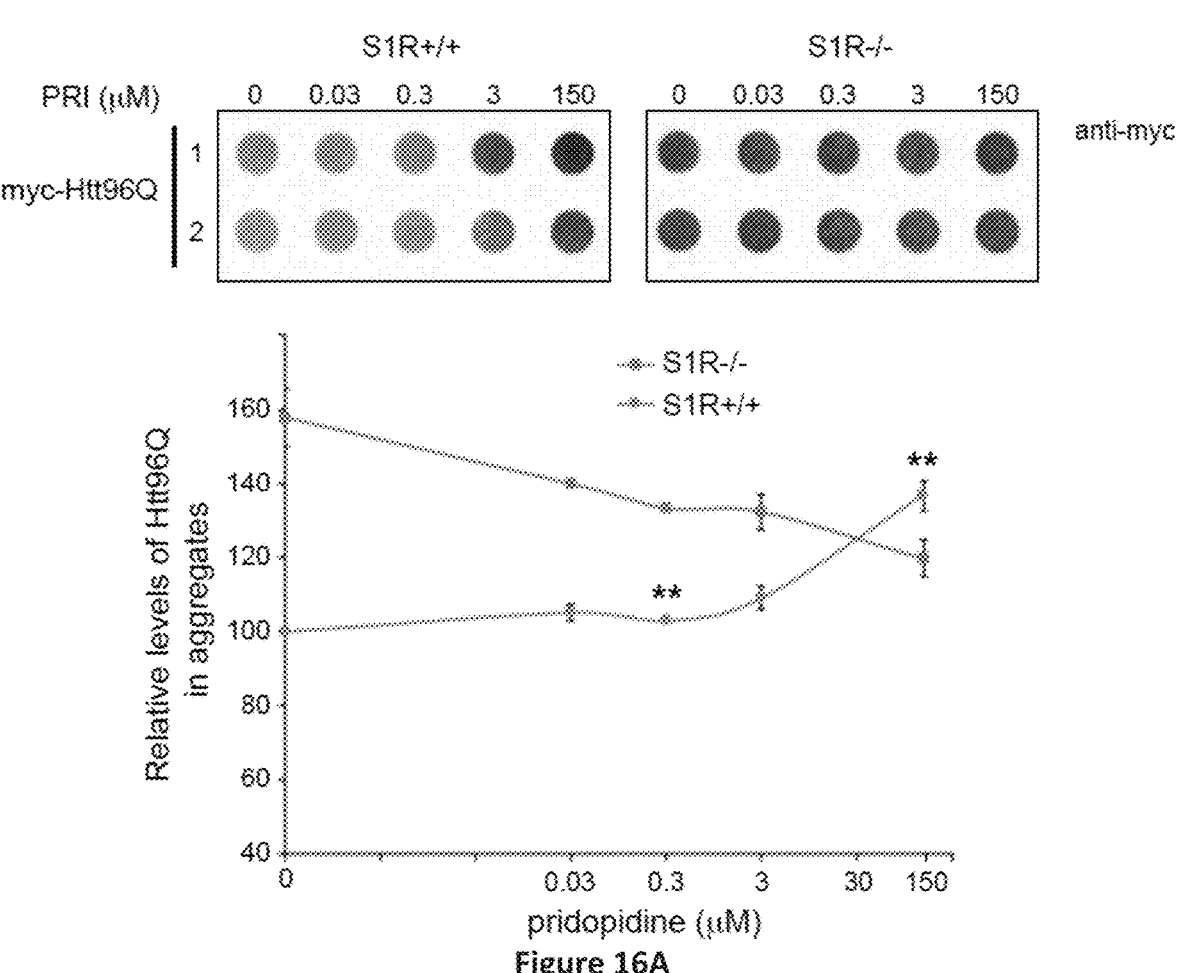
Figure 16B:
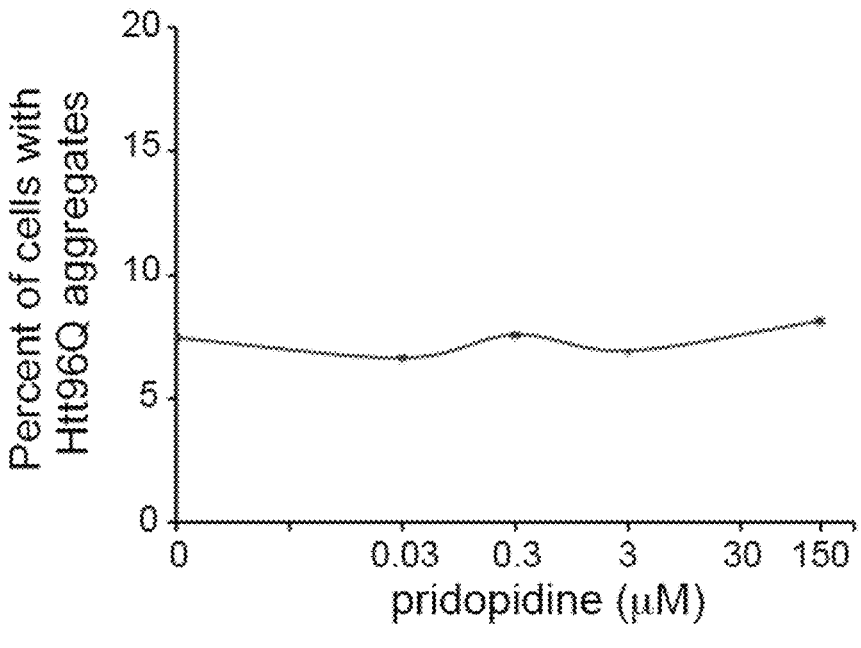

FIGS. 16A-16B. Pridopidine increases the sequestration of mHtt into insoluble aggregates in a S1R-dependent manner.

FIG. 16A. Mutant myc-Htt96Q was expressed in S1R −/− or control WT HEK 293 cells for 24 h treated with the indicated concentrations of pridopidine. SDS-resistant mHtt aggregates were detected (in duplicates 1,2) in cell lysates using a filter trap assay and reaction of the membranes with anti-myc. Pridopidine increases the relative levels of mutant Htt96Q into aggregates in S1R+/+(WT) cells (circles), but not in S1R −/− cells (squares). The graph is an average of 3 experiments±SE. P values±0.01 (**).

FIG. 16B. The number of cells with visible Htt96Q-mCherry aggregates were counted in the experiment of FIGS. 10A-10F, and the percent calculated relative to the total. Thus, pridopidine does not affect the percent of cells with Htt96Q aggregates. The graph is an average of 3 experiments±SE.

Figure 17:
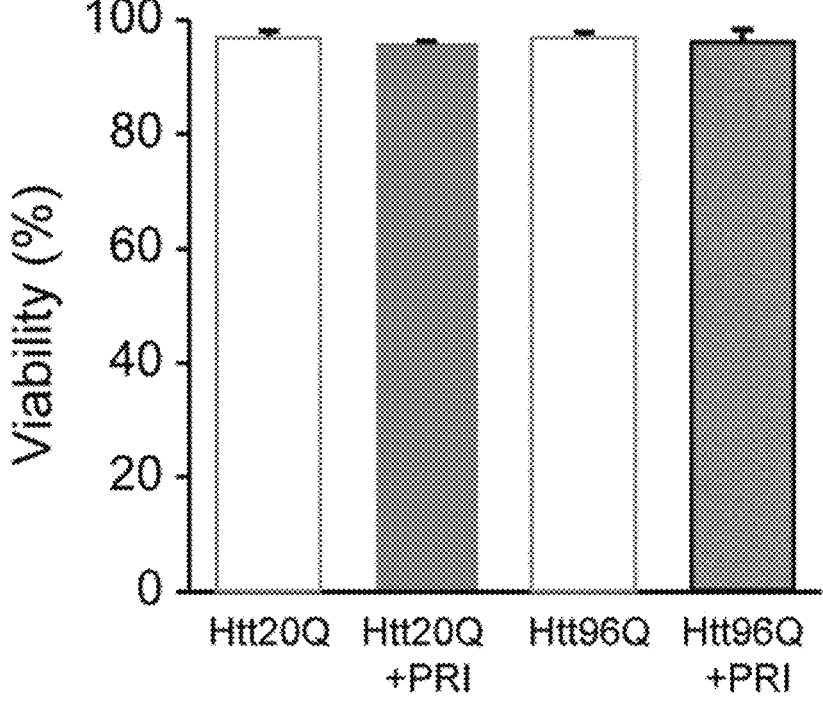

FIG. 17. Cell viability is not altered in response to Htt96Q expression or pridopidine treatment. myc-Htt20Q or myc-Htt96Q were transiently expressed in HEK 293 cells treated with 150 μM pridopidine for 48 h, which are the maximum concentration and time used in other experiments. Cell viability was measured in triplicates after Trypan blue staining.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, the present invention provides a method for treating a disease, disorder or condition, or any symptom thereof which is associated with mitochondrial dysfunction, in a subject in need thereof comprising administering to the subject an effective dose of a composition comprising pridopidine or pharmaceutically acceptable salt thereof, thereby treating the subject.

In another embodiment, the present invention provides a composition comprising pridopidine or pharmaceutically acceptable salt thereof for use in a method for treating a disease, disorder or any symptom thereof which is associated with mitochondrial dysfunction.

In another embodiment, the present invention provides a method of treating a disease, disorder, or condition associated with mitochondrial dysfunction in a subject, or any symptom thereof, comprising administering to said subject a composition comprising a sigma-1 receptor activator. In one embodiment, treating comprises delaying progression of the disease, disorder or condition.

In another embodiment, the present invention provides a method of suppressing a disease, disorder, or condition associated with mitochondrial dysfunction in a subject, or any symptom thereof, comprising administering to said subject a composition comprising a sigma-1 receptor activator. In one embodiment, suppressing comprises reducing or ameliorating symptoms of the disease, disorder or condition.

In another embodiment, the present invention provides a method of inhibiting a disease, disorder, or condition associated with mitochondrial dysfunction in a subject, or any symptom thereof, comprising administering to said subject a composition comprising a sigma-1 receptor activator. In one embodiment, inhibiting comprises prolonging subject survival.

In another embodiment, the present invention provides a method of preventing a disease, disorder, or condition associated with mitochondrial dysfunction in a subject, or any symptom thereof, comprising administering to said subject a composition comprising a sigma-1 receptor activator. In one embodiment, preventing comprises delaying onset to the disease, disorder or condition.

In one embodiment, the composition for use as described herein is administered prior to a cytotoxic stimulus, which, in one embodiment, comprises chemotherapy with trastuzumab, sunitinib, or doxorubicin. In another embodiment, the composition for use as described herein is administered prior to the onset of symptoms of said disease, disorder, or condition. In one embodiment, said disease, disorder, or condition associated with mitochondrial dysfunction is detected by one or more genetic tests.

In one embodiment, the sigma-1 receptor activator comprises a sigma-1 receptor agonist. In one embodiment, the sigma-1 receptor agonist is a selective sigma-1 receptor agonist. In one embodiment the sigma-1 receptor agonist is Pridopidine.

In another embodiment, the sigma-1 receptor agonist comprises PRE-084, ANAVEX2-73, Donepezil, Fluvoxamine, Citalopram, Amitriptyline, L-687,384, SA-4503, Dextromethorphan, Dimethyltryptamine, (+)-pentazocine, Opipramol, or a combination thereof.

In one embodiment, a "disease, disorder, or condition, or any symptom thereof which is associated with mitochondrial dysfunction" encompasses any type of condition that risks the health of a subject wherein the impaired function of the mitochondria or any its parts plays a direct or indirect role.

In one embodiment, the disease, disorder, or condition associated with mitochondrial dysfunction comprises Frontotemporal Dementia (FTD). In another embodiment, the disease, disorder, or condition associated with mitochondrial dysfunction comprises Charcot-Marie-Tooth Disease (CMT). In another embodiment, the disease, disorder, or condition associated with mitochondrial dysfunction comprises retinal degeneration. In another embodiment, the disease, disorder, or condition associated with mitochondrial dysfunction comprises glaucoma. In another embodiment, the disease, disorder, or condition associated with mitochondrial dysfunction comprises Rett Syndrome. In another embodiment, the disease, disorder, or condition associated with mitochondrial dysfunction comprises Fragile X syndrome.

In some embodiments, the disease, disorder, condition, or symptom that is associated with mitochondrial dysfunction is a disease, disorder or any symptom associated with mitochondrial myopathy.

In other embodiments, said mitochondrial myopathy is selected from MELAS syndrome, MERRF syndrome, Leigh Disease, Alpers Syndrome, Chronic Progressive External Ophthalmoplegia (C/PEO), Diabetes mellitus and deafness (MIDD or DAD, Kearns-Sayre syndrome (KSS), Mitochondrial DNA depletion syndrome (MDS), Mitochondrial neurogastrointestinal encephalomyopathy (MNGIE), Neuropathy, ataxia and retinitis pigmentosa (NARP), Pearson syndrome, Lebers Hereditary Optic Neuropathy (LHON), Dominant Optic Atrophy (DOA), Pigmentary retinopathy, Wolfram Syndrome, Friedrich's Ataxia (FRDA), Mitochondrial neurogastrointestinal encephalomyopathy (MNGIE) and any combinations thereof.

In one embodiment, "Mitochondrial Myopathies" encompass are any disease or disorder or any symptom caused by dysfunctional mitochondria. Mitochondrial diseases are sometimes (about 15% of the time) caused by mutations in the mitochondrial DNA that affect mitochondrial function. Other mitochondrial diseases are caused by mutations in genes of the nuclear DNA, whose gene products are imported into the mitochondria (mitochondrial proteins) as well as acquired mitochondrial conditions. Mitochondrial diseases take on unique characteristics both because of the way the diseases are often inherited and because mitochondria are so critical to cell function. The subclass of these diseases that have neuromuscular disease symptoms are often called a mitochondrial myopathy.

Mitochondrial myopathy diseases and disorders include, but are not limited to:

MELAS syndrome (mitochondrial myopathy, encephalopathy, lactic acidosis, and stroke). Progressive neurodegenerative disorder caused by mutations in mitochondrial DNA. Because the disease is poorly known and can be difficult to diagnose, it is not yet known how many individuals have developed MELAS throughout the world. The syndrome affects all ethnic groups and both males and females. Affected individuals usually begin showing symptoms between the ages of 4 and 40. The prognosis is poor; the disease often is fatal. There is no cure for MELAS syndrome; medical care is largely supportive. Symptoms: Because defective mitochondria exist in all the cells of patients with MELAS syndrome, many kinds of symptoms can develop, which are often debilitating. Strokes cause brain damage, leading to seizures, numbness, or partial paralysis. The encephalopathy (brain disease) causes tremors, muscle spasms, blindness, deafness, and may lead to dementia. Myopathy (muscle disease) causes difficulty walking, moving, eating, and speaking.

MERRF syndrome (or myoclonic epilepsy with ragged red fibers) Extremely rare disorder that begins in childhood and affects the nervous system and skeletal muscle as well as other body systems. The distinguishing feature in MERRF is myoclonus, consisting of sudden, brief, jerking spasms that can affect the arms and legs or the entire body. In addition, individuals with MERRF syndrome may have muscle weakness (myopathy), an impaired ability to coordinate movements (ataxia), seizures, and a slow deterioration of intellectual function (dementia). Short stature, degeneration of the optic nerve (optic atrophy), hearing loss, cardiomyopathy and abnormal sensation from nerve damage (peripheral neuropathy) are also common symptoms. Abnormal muscle cells are present and appear as ragged red fibers (RRF) when stained with the modified Gomori trichrome and viewed microscopically. MERRF is caused by mutations in mitochondrial DNA (mtDNA).

Leigh Disease prevalence at birth has been estimated at approximately 1 in 36 000. Typical onset of symptoms occurs before the age of 12 months but, in rare cases, the disease may manifest during adolescence or even early adulthood. Loss of motor milestones, hypotonia with poor head control, recurrent vomiting, and a movement disorder are common initial symptoms. Pyramidal and extrapyramidal signs, nystagmus, breathing disorders, ophthalmoplegia and peripheral neuropathy are often noted later. Epilepsy is relatively uncommon. There is no specific treatment for Leigh disease.

Chronic Progressive External Ophthalmoplegia (C/PEO) Characterized by slowly progressive paralysis of the extraocular muscles. Patients usually experience bilateral, symmetrical, progressive ptosis, followed by ophthalmoparesis months to years later. Ciliary and ins muscles are not involved. CPEO is the most frequent manifestation of mitochondrial myopathies. CPEO in association with mutations in mitochondrial DNA (mtDNA) may occur in the absence of any other clinical sign, but it is usually associated with skeletal muscle weakness. However, individuals with a similar clinical presentation may have various mitochondrial defects.

Diabetes mellitus and deafness (MIDD or DAD) MIDD represents 1% of people who have diabetes. Over 85% of people that carry the mutation in mitochondrial DNA at position 3243 present symptoms of diabetes. The average age at which people who have MIDD are typically diagnosed is 37 years old but has been seen to range anywhere between 11 years to 68 years old. Of these people with diabetes carrying the mitochondrial DNA mutation at position 3243, 75% experience sensorineural hearing loss. In these cases, hearing loss normally appears before the onset of diabetes and is marked by a decrease in perception of high tone frequencies. The associated hearing loss with diabetes is typically more common and more quickly declining in men than in women.

Kearns-Sayre syndrome (KSS) Onset: Before age 20. The prevalence of Kearns-Sayre syndrome is approximately 1 to 3 per 100,000 individuals. Rare neuromuscular disorder. An important clinical symptomatic feature is the presence of a mono- or bilateral ptosis (partial closure of the eyelids). This disease is mostly characterized by three primary findings: progressive paralysis of certain eye muscles (chronic progressive external ophthalmoplegia [CPEO]); abnormal accumulation of colored (pigmented) material on the nerve-rich membrane lining the eyes (atypical retinitis pigmentosa), leading to chronic inflammation, progressive degeneration, and wearing-away of certain eye structures (pigmentary degeneration of the retina); and heart disease (cardiomyopathy) such as heart block. Other findings may include muscle weakness, short stature, hearing loss, and/or the loss of ability to coordinate voluntary movements (ataxia) due to problems affecting part of the brain (cerebellum). In some cases, KSS may be associated with other disorders and/or conditions.

Alpers Syndrome (Alpers-Huttenlocher Syndrome): Onset: Weeks to years after birth. Symptoms: psychomotor regression (dementia), seizures and liver disease. Severe, and continuous seizures lead to death within the first decade of life.

Mitochondrial DNA depletion syndrome (MDS) Onset: Infancy Symptoms: This disorder typically causes muscle weakness and/or liver failure, and more rarely, brain abnormalities. "Floppiness," feeding difficulties and developmental delays are common symptoms; PEO and seizures are less common.

Mitochondrial neuro-gastrointestinal encephalomyopathy (MNGIE) Onset: Usually before age 20. Symptoms: This disorder causes PEO, ptosis (droopy eyelids), limb weakness and gastrointestinal (digestive) problems, including chronic diarrhea and abdominal pain. Another common symptom is peripheral neuropathy (a malfunction of the nerves that can lead to sensory impairment and muscle weakness).

Neuropathy, ataxia and retinitis pigmentosa (NARP) Onset: Infancy to adulthood. Symptoms: NARP causes neuropathy (a malfunction of the nerves that can lead to sensory impairment and muscle weakness), ataxia and retinitis pigmentosa (degeneration of the retina in the eye, with resulting loss of vision). It also can cause developmental delay, seizures and dementia.

Pearson syndrome Onset: Infancy. Symptoms: This syndrome causes severe anemia and malfunction of the pancreas. Children who survive the disease usually go on to develop Kearns-Sayre syndrome.

Lebers Hereditary Optic Neuropathy (LHON) Characterized by acute and painless central vision loss of both eyes in a sequential fashion over a period of days to months, LHON was the first maternally-inherited ophthalmologic disorder to be linked to a point mutation in mitochondrial DNA. LHON has a recognized disease prevalence estimated at 1 in 25,000 in England and other areas of Europe. Three mtDNA point mutations within mitochondrial respiratory chain complex I subunit genes (G11778A in ND4, G3460A in ND1, and T14484C in ND6) collectively cause 95% of LHON cases. Other pathogenic mtDNA mutations continue to be identified, particularly among non-Caucasian ethnic groups, such as the recently identified mtDNA T12338C mutation in ND5 that appears to be common in Han Chinese.

Dominant Optic Atrophy (DOA) DOA is a genetic disease that primarily affects the retinal ganglion cells (RGC) and nerve fiber layer of the retina. The prevalence of DOA is estimated at 1 in 35,000 individuals in northern Europe. Visual acuity typically decreases over the first two decades of life to a mean of 20/80 to 20/120. Thinning of the neuroretinal rim appears to be a universal finding in DOA, with occasional findings including "saucerization" of the disc, a cup to disc ratio exceeding 0.5, and peripapillary atrophy. The early optic nerve appearance is often characterized by sectoral pallor of the optic nerve.

Pigmentary retinopathy and other ophthalmologic problems Pigmentary retinopathy is a non-specific finding that may be found in several mitochondrial diseases. The best described primary mtDNA disease in which pigmentary retinopathy may be seen is Neurogenic weakness, Ataxia, and Retinitis Pigmentosa (NARP), which results from a T8993C mtDNA mutation in the mitochondrial complex V subunit gene, ATPase 6.

Wolfram Syndrome an inherited condition that is typically associated with childhood-onset insulin-dependent diabetes mellitus and progressive optic atrophy. In addition, many people with Wolfram syndrome also develop diabetes insipidus and sensorineural hearing loss. An older name for the syndrome is DIDMOAD, which refers to diabetes insipidus, diabetes mellitus, optic atrophy, and deafness. Some people have mutations in the same gene that causes Wolfram syndrome but they do not get all the features of the syndrome, so they are said to have WFS1-related disorders. The primary symptoms of Wolfram syndrome (diabetes mellitus, optic atrophy, diabetes insipidus and hearing loss) can emerge at different ages and change at different rates.

Friedrich's Ataxia (FRDA) Genetic, progressive, neuro-degenerative movement disorder, with a typical age of onset between 10 and 15 years. Initial symptoms may include unsteady posture, frequent falling, and progressive difficulty in walking due to impaired ability to coordinate voluntary movements (ataxia). Affected individuals often develop slurred speech (dysarthria), characteristic foot deformities, and an irregular curvature of the spine (scoliosis). FRDA is often associated with cardiomyopathy, a disease of cardiac muscle that may lead to heart failure or irregularities in heart rhythm (cardiac arrhythmias). About a third of the people with FRDA develop diabetes mellitus. The symptoms and clinical findings associated with FRDA result primarily from degenerative changes in the sensory nerve fibers at the point where they enter the spinal cord in structures known as dorsal root ganglia. This results in secondary degeneration of nerve fibers in the spinal cord which leads to a deficiency of sensory signals to the cerebellum, the part of the brain that helps to coordinate voluntary movements.

Mitochondrial neurogastrointestinal encephalomyopathy (MNGIE) Progressive metabolic disorder caused by thymidine phosphorylase (TP) enzyme deficiency. The lack of TP results in systemic accumulation of deoxyribonucleosides thymidine (dThd) and deoxyuridine (dUrd). In these patients, clinical features include mental regression, ophthalmoplegia, and fatal gastrointestinal complications. The accumulation of nucleosides also causes imbalances in mitochondrial DNA (mtDNA) deoxyribonucleoside triphosphates (dNTPs), which may play a direct or indirect role in the mtDNA depletion/deletion abnormalities, although the exact underlying mechanism remains unknown.

In further embodiments, the disease, disorder, condition, or symptom that is associated with mitochondrial dysfunction is a disease, disorder or any symptom associated with a lysosomal storage disease.

In other embodiments, said lysosomal storage disease is selected from Glycogenosis Type II (Pompe Disease), Multiple Sulphatase Deficiency (MSD), Mucopolysaccharidoses (MPS), Mucolipidoses (ML) Types I-III, G(M1)-Gangliosidosis, Fabry Disease, Farber Disease, Gaucher Disease, Niemann-Pick Disease, Mucolipidoses (ML) Type IV, Cystinosis, Neuronal Ceroid-Lipofuscinoses, and any combinations thereof.

In one embodiment, "Lysosomal storage diseases (LSDs)" encompass any disease, disorder or symptom characterized by the progressive accumulation of undigested macromolecules in lysosomes. The massive accumulation of substances affects the function of lysosomes and impairs autophagic flux which may affect the cellular quality control of organelles such as mitochondria. LSDs exhibit signs of mitochondrial dysfunction, which include mitochondrial morphological changes, decreased mitochondrial membrane potential ($\Delta\Psi$m), diminished ATP production and increased generation of reactive oxygen species (ROS). Furthermore, reduced autophagic flux may lead to the persistence of dysfunctional mitochondria. Examples of lysosomal storage disease include, but are not limited to. Glycogenosis Type II (Pompe Disease), Multiple Sulphatase Deficiency (MSD), Mucopolysaccharidoses (MPS), Mucolipidoses (ML) Types I-III, G(M1)-Gangliosidosis, Fabry Disease, Farber Disease, Gaucher Disease, Niemann-Pick Disease, Mucolipidoses (ML) Type IV, Cystinosis, and Neuronal Ceroid-Lipofuscinoses.

In one embodiment, said disease, disorder, or condition associated with mitochondrial dysfunction comprises a mitochondrial myopathy; a lysosomal storage disease, a mood disorder, or a combination thereof.

In one embodiment, the disease, disorder, condition, or symptom that is associated with mitochondrial dysfunction is a disease, disorder or any symptom associated with a neurodegenerative disease.

In one embodiment, a "neurodegenerative disease" is a disabling disease, disorder, or condition of the nervous system, characterized by the death of selective neuronal subtypes. Impaired mitochondrial function is key in the development of these diseases, including impairments in impaired mitochondrial dynamics (shape, size, fission-fusion, distribution, movement etc.), abnormal mitochondrial membrane potential, oxygen consumption rate, and ROS levels.

In one embodiment, neurodegenerative diseases comprise Parkinson's disease, Huntington's Disease, amyotrophic lateral sclerosis, Charcot-Marie-Tooth Disease (CMT), and Alzheimer's disease.

In one embodiment, the disease, disorder, or condition comprises Parkinson's disease. In another embodiment, the disease, disorder, or condition comprises Huntington's Disease. In another embodiment, the disease, disorder, or condition comprises amyotrophic lateral sclerosis. In another embodiment, the disease, disorder, or condition comprises Frontotemporal Dementia (FTD). In another embodiment, the disease, disorder, or condition comprises Charcot-Marie-Tooth Disease (CMT). In another embodiment, the disease, disorder, or condition comprises Alzheimer's disease. In another embodiment, the disease, disorder, or condition comprises retinal degeneration. In another embodiment, the disease, disorder, or condition comprises glaucoma. In another embodiment, the disease, disorder, or condition comprises Rett Syndrome. In another embodiment, the disease, disorder, or condition comprises Fragile X syndrome. In another embodiment, the disease, disorder, or condition comprises a combination of the above-referenced diseases, disorders, and conditions.

In some embodiments, the neurodegenerative disease is selected from Parkinson's disease, Huntington's Disease, amyotrophic lateral sclerosis, Frontotemporal Dementia (FTD), Charcot-Marie-Tooth Disease (CMT), Alzheimer's disease, and any combinations thereof.

In some embodiments, the disease, disorder, condition, or symptom that is associated with mitochondrial dysfunction is vanishing white matter (VWM) disease. Vanishing White Matter Disease (VWM) is one of more than 50 conditions that affect the white matter, or myelin, of the brain known collectively as Leukodystrophies. VWM, also known as Childhood Ataxia with Central Nervous System Hypomyelination (CACH), is an extremely rare neurological condition that destroys myelin, the brain's white matter, or myelin. In doing so, it permanently affects transmission of brain signals to the rest of the body. Clinical conditions identified under VWM disease include but are not limited to: Childhood Ataxia with diffuse CNS Hypomyelination (CACH), Vanishing White Matter Leukodystrophy (VWM), Cree Leukoencephalopathy, Vanishing White Matter Leukodystrophy with Ovarian Failure, and any combinations thereof.

In further embodiments, the invention provides a method for treating a disease, disorder or any symptom thereof which is associated with mitochondrial dysfunction, in a subject in need thereof comprising administering to the subject a composition comprising pridopidine or pharmaceutically acceptable salt thereof, wherein the mitochondrial dysfunction is a bipolar disorder.

In one embodiment, "bipolar disorder" is a major mental disorder showing manic and depressive episodes, frequently accompanying psychotic symptoms. Mutations in mitochondrial DNA and mitochondrial dysfunction account for a subset of patients with the disorder.

In further embodiments, the invention provides a method for treating a disease, disorder or any symptom thereof which is associated with mitochondrial dysfunction, in a subject in need thereof comprising administering to the subject a composition comprising pridopidine or pharmaceutically acceptable salt thereof, wherein the symptom of a disease or disorder associated with mitochondrial dysfunction include any one or more of the following: poor growth, loss of muscle coordination, muscle weakness, neurological deficit, seizures, autism, autistic spectrum, autistic-like features, learning disabilities, heart disease, liver disease, kidney disease, gastrointestinal disorders, severe constipation, diabetes, increased risk of infection, thyroid dysfunction, adrenal dysfunction, autonomic dysfunction, confusion, disorientation, memory loss, poor growth, failure to thrive, poor coordination, sensory (vision, hearing) problems, reduced mental functions, disease of the organ, dementia, respiratory problems, hypoglycemia, apnea, lactic acidosis, seizures, swallowing difficulties, developmental delays, movement disorders (dystonia, muscle spasms, tremors, chorea), stroke, and brain atrophy.

In another embodiment, the present invention provides a method of improving mitochondrial function, preventing mitochondrial dysfunction, recovering mitochondrial function, or increasing cell viability in a subject comprising administering to the subject a composition comprising an activator of the sigma-1 receptor, as was demonstrated herein in Examples 2-6.

Mitochondria are involved in synthesis of biomolecules, maintenance of calcium homeostasis, production of reactive oxygen species (ROS), and apoptosis activation. Mitochondria undergo constant morphological changes by the process of continuous cycles of fusion and fission that determines their morphology and most mitochondrial functions.

In one embodiment, the method of improving mitochondrial function comprises increasing mitochondrial activity, elongation, motility, or a combination thereof.

In another embodiment, the method of improving mitochondrial function comprises increasing mitochondrial respiration.

In another embodiment, the method of improving mitochondrial function comprises increasing the number of mitochondria-endoplasmic reticulum (ER) contact sites.

In another embodiment, the method of improving mitochondrial function comprises reducing mitochondrial reactive oxygen species (ROS) levels.

In another embodiment, the present invention provides a method of cytoprotection in a subject with a disease, disorder or condition involving dysfunction of the mitochondria comprising administering to the subject a composition comprising an activator of the sigma-1 receptor.

In another embodiment, the present invention provides a method of reducing endoplasmic reticulum (ER) stress in a subject comprising administering to the subject a composition comprising an activator of the sigma-1 receptor, as was demonstrated herein in Examples 8-12.

Physiologic stresses, such as increased secretory load, or pathological stresses, such as the presence of mutated proteins that cannot properly fold in the ER, can lead to an imbalance between the demand for protein folding and the capacity of the ER for protein folding, thereby causing ER stress. To sense and respond to ER stress, eukaryotic cells have evolved a group of signal transduction pathways, collectively termed the unfolded protein response (UPR). ER stress may occur when the capacity of the ER to fold proteins becomes saturated. ER stress may be caused by factors that impair protein glycosylation or disulfide bond formation, or by overexpression of or mutations in proteins entering the secretory pathway.

In one embodiment, ER stress is associated with obesity, diabetes, cancer, neurodegenerative disorders, inflammatory diseases, infectious diseases, or a combination thereof. In another embodiment, ER stress is associated with heritable forms of diabetes. In another embodiment, ER stress is associated with neurodegeneration.

In some embodiments, the pridopidine for use in the methods of the present invention is in its neutral/base from. In other embodiments, pridopidine is in a pharmaceutically acceptable salt form. In some embodiments, the pridopidine is pridopidine hydrochloride.

In one embodiment, "pridopidine" as described herein comprises a pridopidine base, a pharmaceutically acceptable salt thereof, derivative thereof, analog thereof, or a combination of pridopidine and its analogs.

Example of pridopidine derivative is deuterium-enriched version of pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference.

In one embodiment, "deuterium-enriched" describes a compound in which the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%. Deuterium-enriched compounds may be obtained by exchanging hydrogen with deuterium or synthesizing the compound with deuterium-enriched starting materials.

The invention also includes any salt of pridopidine or other sigma-1 receptor activator, including any pharmaceutically acceptable salt, wherein pridopidine has a net charge (either positive or negative) and at least one counter ion (having a counter negative or positive charge) is added thereto to form said salt. In one embodiment, the phrase "pharmaceutically acceptable salt(s)", as used herein, means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al., 66 *J. Pharm. Sci.* 1-19 (1977), which is incorporated herein by reference. In another embodiment, the pridopidine salt of this invention is a hydrochloride salt.

In some embodiments, the methods of this invention make use of a combination of pridopidine or other sigma-1 receptor activators or a pharmaceutically acceptable salt thereof with one or more of its analogs or pharmaceutically acceptable salt thereof.

In one embodiment, the analogs of pridopidine are represented by the following structures:

(1)

(2)

(3)

(4)

-continued (5)

(6)

, or (7)

.

In other embodiments, the methods of this invention make use of a combination of pridopidine or pharmaceutically acceptable salt thereof and Compound (1) or pharmaceutically acceptable salt thereof. In other embodiments, the methods of this invention make use of a combination of pridopidine or pharmaceutically acceptable salt thereof and Compound (2) or pharmaceutically acceptable salt thereof. In other embodiments, the methods of this invention make use of a combination of pridopidine or pharmaceutically acceptable salt thereof and Compound (3) or pharmaceutically acceptable salt thereof. In other embodiments, the methods of this invention make use of a combination of pridopidine or pharmaceutically acceptable salt thereof and Compound (4) or pharmaceutically acceptable salt thereof. In other embodiments, the methods of this invention make use of a combination of pridopidine or pharmaceutically acceptable salt thereof and Compound (5) or pharmaceutically acceptable salt thereof. In other embodiments, the methods of this invention make use of a combination of pridopidine or pharmaceutically acceptable salt thereof and Compound (6) or pharmaceutically acceptable salt thereof. In other embodiments, the methods of this invention make use of a combination of pridopidine or pharmaceutically acceptable salt thereof and Compound (7) or pharmaceutically acceptable salt thereof.

In other embodiments, the methods of this invention make use of a combination of pridopidine or pharmaceutically acceptable salt thereof and Compound (1), Compound (4) or a pharmaceutically acceptable salt thereof, or a combination thereof.

In other embodiments, the methods of this invention make use of a combination of pridopidine or pharmaceutically acceptable salt thereof, Compound (1) and Compound (4) or pharmaceutically acceptable salt thereof.

In some embodiments, provided herein a method of treating, suppressing, or inhibiting a disease, disorder, or condition associated with mitochondrial dysfunction in a subject, or any symptom thereof, comprising administering to said subject a composition comprising pridopidine or pharmaceutically acceptable salt thereof, in combination with Compound (1), or Compound (4), a pharmaceutically acceptable salt thereof, or a combination thereof; wherein said disease, disorder, or condition associated with mitochondrial dysfunction comprises:

a) a mood disorder;

b) a mitochondrial myopathy;

c) a lysosomal storage disease;

d) Frontotemporal Dementia (FTD);

e) Charcot-Marie-Tooth Disease (CMT);

or a combination thereof.

In some embodiments, provided herein a method of improving mitochondrial function, preventing mitochondrial dysfunction, recovering mitochondrial function, or increasing cell viability in a subject comprising administering to the subject a composition comprising pridopidine or pharmaceutically acceptable salt thereof in combination with Compound (1), or Compound (4), a pharmaceutically acceptable salt thereof, or a combination thereof.

In some embodiments, provided herein a method of reducing ER stress in a subject comprising administering to the subject a composition comprising pridopidine or pharmaceutically acceptable salt thereof, in combination with Compound (1), or Compound (4), a pharmaceutically acceptable salt thereof, or a combination thereof.

For the methods and use disclosed herein, the route of administration of the sigma-1 receptor activator can be, for e.g., oral. Routes of administration can also be classified by whether the effect is local (e.g., in topical administration) or systemic (e.g., in enteral or parenteral administration). In one embodiment, "local administration" as used herein shall mean administration of a compound or composition directly to where its action is desired, and specifically excludes systemic administration. In one embodiment, "topical administration" of a compound or composition as used herein shall mean application of the compound or composition to body surfaces such as the skin or mucous membranes such as eyes. In one embodiment, "ocular administration" as used herein shall mean application of a compound or composition to the eye of a subject or to the skin around the eye (periocular skin) or the mucosa around the eye, specifically the conjunctiva of a subject, i.e., local administration. The amount of pridopidine and the pharmaceutical compositions of the present invention may be administered by oral administration, topical administration, systemic administration, local administration, or ocular administration.

In some embodiments, the sigma-1 receptor activator is administered orally.

In further embodiments, the sigma-1 receptor activator is administered in the form of an inhalable powder, an injectable, a liquid, a gel, a solid, eye-drops, eye ointment, capsule or a tablet.

In further embodiments, the sigma-1 receptor activator is administered in the form of a multi-particulate delivery vehicle comprising pellets, beads, granules, microparticles, nanoparticles, or a combination thereof.

The present invention thus also relates to pharmaceutical compositions comprising an agent of the subject invention in admixture with pharmaceutically acceptable auxiliaries, and optionally other therapeutic agents. In one embodiment, the auxiliaries are "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrates, lubricants, colorants, flavoring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulizers or insufflators.

The exact dose and regimen of administration of the composition will necessarily be dependent upon the therapeutic or nutritional effect to be achieved and may vary with the formula, the route of administration, and the age and condition of the individual subject to whom the composition is to be administered.

In one embodiment, the term "treatment" as used herein refers to the administering of a therapeutic amount of the composition of the present invention which is effective to ameliorate undesired diseases, disorders, including symptoms associated with a diseases or disorders, to prevent the manifestation of such diseases, disorders, including symptoms associated with a diseases or disorders before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

In some embodiments, the composition comprising pridopidine is administered periodically. In some embodiment, pridopidine is administered at regular pre-determined intervals. In one embodiment, the pre-determined interval comprises daily periods. In another embodiment, the pre-determined interval comprises hourly periods. In another embodiment, the pre-determined interval comprises weekly periods. In another embodiment, the pre-determined interval comprises monthly periods.

In one embodiment, the interval of time may optionally also define the dose to be administered and the number of administrations per time period. In further embodiments, the composition for use in the methods described herein is administered once daily. In another embodiment, the composition for use in the methods described herein is administered twice daily. In another embodiment, the composition for use in the methods described herein is administered three times a day.

In further embodiments, the composition as described herein is administered less often than once daily. In some embodiments, the composition is administered in one dose per day. In another embodiment, the composition is administered in two doses per day. In another embodiment, the composition is administered in three doses per day.

In one embodiment, the "effective amount" for purposes disclosed herein is determined by such considerations as may be known in the art. The amount must be effective to achieve the desired therapeutic effect as described above, depending, inter aba, on the type and severity of the disease to be treated and the treatment regime. In some embodiments, a composition comprising a sigma-1 receptor activator such as pridopidine or pharmaceutically acceptable salt thereof is administered at a dose of between 1-400 mg, daily, twice daily, three times per day or less often than once a day. As generally known, an effective amount depends on a variety of factors including the affinity of the ligand to the receptor, its distribution profile within the body, a variety of pharmacological parameters such as half-life in the body, on undesired side effects, if any, on factors such as age and gender, etc.

In some embodiments, the sigma-1 receptor activator such as pridopidine is administered in a daily dose of between 1 mg/day-400 mg/day. In some embodiments, the sigma-1 receptor activator such as pridopidine is administered in a daily dose of between 1 mg/day-300 mg/day. In other embodiments, the sigma-1 receptor activator such as pridopidine is administered in a daily dose of between 1 mg/day-90 mg/day. In other embodiments, the sigma-1 receptor activator such as pridopidine is administered in a daily dose of between 20 mg/day-90 mg/day. In further embodiments, the sigma-1 receptor activator such as pridopidine is administered in a daily dose of between 45 mg/day-90 mg/day. In other embodiments, the sigma-1 receptor activator such as pridopidine is administered in a daily dose of between 20 mg/day-50 mg/day. In further embodiments, the sigma-1 receptor activator such as pridopidine is administered in a daily dose of between 1 mg/day-10 mg/day. In further embodiments, the sigma-1 receptor activator such as pridopidine is administered in a daily dose of between 10 mg/day-20 mg/day. In further embodiments, the sigma-1 receptor activator such as pridopidine is administered in a daily dose of between 20 mg/day-30 mg/day. In further embodiments, the sigma-1 receptor activator such as pridopidine is administered in a daily dose of between 30 mg/day-40 mg/day. In further embodiments, the sigma-1 receptor activator such as pridopidine is administered in a daily dose of between 40 mg/day-50 mg/day. In further embodiments, the sigma-1 receptor activator such as pridopidine is administered in a daily dose of between 50 mg/day-60 mg/day. In further embodiments, pridopidine is administered in a daily dose of between 60 mg/day-70 mg/day. In further embodiments, the sigma-1 receptor activator such as pridopidine is administered in a daily dose of between 70 mg/day-80 mg/day. In further embodiments, the sigma-1 receptor activator such as pridopidine is administered in a daily dose of between 80 mg/day-90 mg/day. In further embodiments, the sigma-1 receptor activator such as pridopidine is administered in a daily dose of between 90 mg/day-100 mg/day. In further embodiments, the sigma-1 receptor activator such as pridopidine is administered in a daily dose of between 100 mg/day-150 mg/day. In further embodiments, the sigma-1 receptor activator such as pridopidine is administered in a daily dose of between 150 mg/day-200 mg/day. In further embodiments, the sigma-1 receptor activator such as pridopidine is administered in a daily dose of between 200 mg/day-250 mg/day. In further embodiments, the sigma-1 receptor activator such as pridopidine is administered in a daily dose of between 250 mg/day-300 mg/day. In further embodiments, the sigma-1 receptor activator such as pridopidine is administered in a daily dose of between 300 mg/day-350 mg/day. In further embodiments, the sigma-1 receptor activator such as pridopidine is administered in a daily dose of between 350 mg/day-400 mg/day.

According to any of the methods of the present invention and in one embodiment, a subject as described herein is human. In another embodiment, the subject is a mammal. In another embodiment, the subject is a primate, which in one embodiment, is a non-human primate. In another embodiment, the subject is murine, which in one embodiment is a mouse, and, in another embodiment is a rat. In another embodiment, the subject is canine, feline, bovine, equine, caprine, ovine, porcine, simian, ursine, vulpine, or lupine. In one embodiment, the subject is a chicken or fish.

In one embodiment, "treating" refers to, in one embodiment, therapeutic treatment and, in another embodiment, prophylactic or preventative measures. In one embodiment, the goal of treating is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging subject survival, or a combination thereof.

EXPERIMENTAL SECTION

Example 1

Materials and Methods

Animals and Ethical Permits

Colonies of hemizygous YAC128 [line HD53; mHTT high expresser], homozygous YAC128 [line HD55; mHTT low expresser] and WT mice, all with FVB/N background, were housed in the housing Facility of the CNC, Coimbra, Portugal, and at UBC, Vancouver, Canada. Temperature was controlled (22-23° C.) and a 12-h light/dark cycle maintained. Food and water were available ad libitum. All mouse experiments were carried out in accordance with the guidelines of the Institutional Animal Care and Use of Committee and the European Community directive (2010/63/EU) and protocols approved by the Faculty of Medicine, University of Coimbra (ref: ORBEA_189_2018/11042018) and UBC Committee (ref: A16-0130) on Animal Care and the Canadian Council on Animal Care. All efforts were made to minimize animal suffering and to reduce the number of animals used.

Primary Neuronal Cultures

Primary cortical, striatal and cortico-striatal co-cultures were generated from the offspring of crosses between wild-type (WT) mice (used as controls), or between homozygous YAC128 mice [line HD55] males or hemizygous YAC128 mice [line HD53] males and WT females from the same genetic background (FVB/N). Embryos from timed pregnant females were collected on gestational day E15.5-16.5.

For cortico-striatal co-cultures, brains were removed and transferred to Hibernate E medium (Thermo Fisher Sci., catalog no: A1247601) for up to 24 h. At this time, the samples from the remaining embryonic tissues were genotyped. The cortex and striatum were micro-dissected in ice-cold Hank's balanced salt solution (HBSS; Gibco), then diced and pooled per genotype. The tissues were then dissociated with 0.05% trypsin-EDTA (Thermo Fisher Sci., catalog no: 25300054), which was then neutralized with 10% fetal bovine serum (FBS) in Neurobasal medium (Thermo Fisher Sci., catalog no: 21103049) and DNAse I treatment (153 U/ml). The dissociated tissues were centrifuged at 145×g for 5 min and the pellet was then triturated with a pipette five to six times. Cells were seeded on poly-D-lysine coated plates in Neurobasal media supplemented with 2% B27 (Thermo Fisher Sci., catalog no: 17504044), 100 U/ml penicillin-streptomycin (Gibco, catalog no: 15140122), 2 mM L-glutamax (Thermo Fisher Sci., catalog no: 35050061). The cells were fed with ⅓ volume fresh medium every fifth day.

To obtain pure cortical and striatal neurons, tissue was micro-dissected in HBSS supplemented with 0.3% fatty acid free BSA (Sigma-Aldrich, catalog no: A8806). Tissue from embryos with the same genotype were pooled and digested with 0.003% trypsin in HBSS, then mechanically digested. Soybean (Sigma-Aldrich, catalog no: T9128) was used to block the trypsin. Neurons were plated at a density of either $130 \times 10^3$ cells/cm$^2$ (high) or $85 \times 10^3$ cells/cm$^2$ (low) on poly-D-lysine (0.1 mg/ml) coated plates, and maintained in Neurobasal medium supplemented with 2% B27, 1 mM glutamine, 20 µg/ml gentamicin (Thermo Fisher Sci., catalog no. 15750060). Cultures were incubated at 37° C. with 5% CO$_2$. After 3 days in vitro (DIV) half of the medium was replaced with fresh supplemented Neurobasal medium containing 5-fluoro-2'-deoxyuridine (5-FdU, 5 µM final concentration in the medium; Sigma-Aldrich, catalog no: F0503) to reduce dividing non-neuronal cells. At DIV 7 half of the medium was again replaced with fresh, and cells were used at DIV12. Striatal cultures used for single cell measurements displayed 82% of GABA (gamma-aminobutyric acid)-positive plus DARPP-32 (dopamine and cAMP regulated phosphoprotein of 32 kDa)-positive neurons (Naia and Rego 2018).

Neuronal Transfection

Striatal neurons were transfected with pDsRed2-Mito Vector (MitoDsRed; Clontech, catalog no: 632421) at 8 DIV using the calcium phosphate precipitation method as previously described (Fu et al. 2017). Briefly, plasmid was diluted in TE (in mM: 1 Tris-HCl pH 7.3, 1 mM EDTA), followed by the addition of $CaCl_2$ (in mM: 2.5 $CaCl_2$ in 10 HEPES, pH 7.2). The DNA solution was carefully added to 2×HEBS (in mM: 12 dextrose, 50 HEPES, 10 KCl, 280 NaCl and 1.5 $Na_2HPO_4 \cdot 2H_2O$, pH 7.2) while bubbling air through the solution. The mixture was then incubated for 25 min at room temperature. The precipitates were added dropwise to the coverslips in Neurobasal medium and incubated for 80 minutes at 37° C. The DNA-$Ca^{2+}$-phosphate precipitates were dissolved with freshly-made dissolution medium (Neurobasal medium with 20 mM HEPES, pH 6.8) and incubated for 7 min at room temperature. The transfected neurons were then washed with Neurobasal medium and transferred back to their original dishes containing conditioned culture medium until DIV12.

Lymphoblast Cultures and Transfection

Lymphoblasts from control subjects (GM02174, CAG repeat 15/15) and HD patients (NA04724, CAG repeat 67/15) obtained from the Coriell Institute were grown in RPMI medium (Thermo Fisher Sci. 11875093) containing 10% FBS, 2 mM L-glutamax, and 100 U/ml penicillin-streptomycin. The lymphoblasts were passaged 1:3 every five to six days. For conducting experiments, the lymphoblasts were collected and centrifuged at 145×g for 5 min. The cell pellet was resuspended in fresh growth medium. Lymphoblasts between passage number 5 and 20 were used in each experiment.

S1R depletion was induced by treating with S1R-directed siRNA duplexes (Origene, cat no: SR426072). siRNA transfection was performed in antibiotic-free growth medium using the Polyplus JETPRIME transfection protocol as per manufacturer's instructions (Polyplus). Forty-eight hours after transfection the cells were subjected to pridopidine treatment and/or oxidative stress challenge. S1R knockdown efficiency was determined by Immunoblot analysis.

Human Neural Stem Cells Culture

Neural stem cells (NSCs) were differentiated from heterozygous human induced pluripotent stem cells (iPSC), HD4-iPSC, with a normal (19 CAG repeats) and an expanded allele (72 CAG repeats) generated by Park and colleagues (Park et al. 2008), generously provided by Prof. George Daley (Harvard Medical School, Boston, Massachusetts, USA) and control AMS4-iPSC generated and characterized by Pereira de Almeida and collaborators (Onofre et al. 2016)(Center for Neuroscience and Cell Biology, University of Coimbra, Portugal). iPSCs were maintained in Geltrex® (Thermo Fisher Sci., catalog no: A1413202) coated 6-well plates until 90% confluence, then the neural induction protocol was applied. Neural differentiation was based on dual SMAD inhibition with SB431542 (Lefty/ Activin/transforming growth factor beta—TGFβ inhibitor; Tocris Bioscience, catalog no: 1614), dorsomorphin (bone morphogenetic protein—BMP inhibitor; Tebu-bio, catalog no: 04-0024) and XAV-939 (β-catenin-transcription inhibitor and axin stabilizing agent; Sigma-Aldrich, catalog no: X3004), as previously described (Chambers et al. 2009; Delli Carri et al. 2013; Nicoleau et al. 2013). Neural induction medium (N2 medium) consisted of a 1:1 mixture of DMEM/F12 (Thermo Fisher Sci., catalog no: 32500043) and Neurobasal, and supplemented with 1% N2 (100×) (Thermo Fisher Sci., catalog no: 17502048), 2 mM L-glutamine, 100 µM nonessential amino acids (Sigma-Aldrich, catalog no: M7145), 100 µM 2-mercaptoethanol (Sigma-Aldrich, catalog no: M6250), 1% penicillin/streptomycin (Thermo Fisher Sci., catalog no: 15140122) and 2% B27 (50×). Neural induction occurred between day 0 and days 12-15. From day 0 to day 5, cells were maintained in iPSC medium without FGF2 and incubated with 5 µM dorsomorphin and 10 µM SB431542. Medium was changed every other day. From day 5 to day 12, the medium was gradually replaced by 75% KnockOut Serum Replacement+25% N2 medium, 50% iPSC+50% N2 medium up to 100% N2 medium with 5 µM dorsomorphin, 10 µM SB431542 and 1 µM XAV939 (Chambers et al. 2009; Delli Carri et al. 2013; Nicoleau et al. 2013). Between days 12 and 15, fields full of rosettes became morphologically visible. To allow the cells to differentiate, cells were replated in Geltrex® coated 12-well plates. For detaching, 500 µl of 1×Accutase® (Thermo Fisher Sci., catalog no: A1110501) was added to the plate and incubated at 37° C. in 5% $CO_2$, for 15-20 min. Accutase was diluted in DMEM/F12 medium pre-warmed to 37° C. Cells were collected and spun for 3 min at 200×g at room temperature, and resuspended in 200 µl of media into 12-well plates. Cells were allowed to adhere for 30 min and then 300 µL N2 medium, supplemented with 10 µM Y-27632 (Thermo Fisher Sci.), 10 ng/ml FGF2 (Tebu-bio, catalog no: 100-18B-A) and 10 ng/ml EGF (Tebu-bio, catalog no: AF-100-15-A), was added. Cells were incubated overnight at 37° C., 5% $CO_2$. Cells were passaged every 2-3 days for no more than 10-12 passages. Expression of the neural lineage marker proteins nestin and SOX2 was confirmed by immunocytochemistry upon each differentiation process (data not shown).

Pridopidine Incubations

Pridopidine was provided by Prilenia Therapeutics. A working stock concentration of 10 mM was prepared in sterile deionized water and stored at 4° C. for up to 2 weeks. Pridopidine incubations were done for 24 h in all cellular models used unless otherwise stated (FIG. 3H). Final working concentrations are described in figures and figure legends.

Mitochondrial Network Imaging

Cortico-striatal co-cultures were incubated with Mitotracker Deep Red FM dye (500 nM; Cell Signaling Technology, catalog no. 8778) for 30 min in the dark. The stained cells were washed twice with PBS and fixed with ice-cold methanol for 15 min at room temperature. Mitochondria were visualized using the SP5 confocal microscope (Leica). 8 random areas were sampled. Circularity was determined using ImageJ with an internal plugin.

Immunocytochemistry and Co-Localization Analysis

MitoDsRed-transfected striatal neurons were fixed with 4% paraformaldehyde (pre-warmed at 37° C.) for 20 minutes, permeabilized in 0.2% Triton X-100 in PBS for 2 minutes and blocked for 1 hour at room temperature in 3% (w/v) BSA in PBS. $IP_3R3$ antibody (1:1000 prepared in 3% (w/v) BSA in PBS; EMD Millipore, catalog no. AB9076) and S1R antibody (1:500 prepared in 3% (w/v) BSA in PBS; Santa Cruz Biotechnology, catalog no. sc-137075) were incubated overnight at 4° C. Neurons were incubated with 4 µg/mL Hoechst 33342 (Thermo Fisher Sci., catalog no: H1399) for 20 minutes and mounted using Mowiol 40-88 (Sigma-Aldrich, catalog no: 324590). Confocal images were obtained as stacks, at 0.46 µm intervals along the z axis, using a Plan-Apochromat/1.4NA 63× lens on an Axio Observer.Z1 confocal microscope (Zeiss Microscopy, Germany) with Zeiss LSM 710 software. FIJI (ImageJ, National Institute of Health, USA) was used for image analysis. Z-stacks images were normalized for background (rolling ball radius of 9 for mitochondria and 25 for IP$_3$R3) and the FindFoci function was used to identify peak intensity regions in order to extract mitochondria-specific fluorescence (Herbert, Carr, and Hoffmann 2014). To optimally resolve individual mitochondria, a threshold was applied followed by the Analyze Particles function to trace mitochondrial outlines. For S1R and IP$_3$R3 fluorescence, a threshold was set similarly to the one described above, and Integrated Density was obtained. S1R and IP$_3$R3 Integrated Density was calculated inside of mitochondrial ROIs selection to obtain ER co-localization with mitochondria.

Transmission Electron Microscopy (TEM) and Analysis

Striatal neurons were washed and fixed in 2.5% (V/V) glutaraldehyde in 0.1 M phosphate buffer and pellet before sectioning. The ultrathin sections were prepared using Leica Ultracut UCT (Leica, Vienna, Austria) and contrasted with uranyl acetate and lead citrate. Sections were observed in a Tecnai 12 BioTWIN transmission electron microscope (FEI Company, Eindhoven, The Netherlands) at 100 kV. Digital images were taken using a magnification of 26,500× in a Veleta camera (Olympus Soft imaging Solutions, GmbH, Munster, Germany). All mitochondria of 6-7 different cells were snapped per condition and per independent experiment. Number of mitochondria-ER contacts sites (MERCS), MERCS length, ER and mitochondria profile areas, ER width and mitochondria aspect ratio (the ratio between the major and minor axes of mitochondria) were quantified. Number of MERCS per mitochondria was obtained by dividing number of MERCS per number of mitochondria profiles. Percentage of mitochondria surface covered by ER was measured by dividing the MERCS length by mitochondria perimeter and multiplying by 100. MERCS were considered when the distance between ER and mitochondria <40 nm.

Mitochondrial Movement Analysis

MitoDsRed-transfected striatal neurons were washed and incubated in Na medium (in mM: 140 NaCl, 5 KCl, 1 CaCl$_2$, 1 MgCl$_2$, 10 Glucose, 10 HEPES, pH 7.4) at 37° C. for mitochondrial movement studies. Neuronal projections were imaged every 5 seconds for a total of 145 frames, using a 63× objective with NA=1.4, on a Carl Zeiss Axio Observed Z1 inverted confocal microscope using the CSU-X1M spinning disc technology (Zeiss, Jena, Germany). Mitochondrial movement analysis was performed using the Kymograph Macro (Rietdorf and A 2008) in FIJI. Briefly, histograms were matched to the first frame to correct fluorescence variations using Bleach Correction plugin developed by Miura and Rietdorf, and time lapse-dependent x-y drift was corrected by applying the TurboReg plugin. ROIs were designated using a segmented line following mitochondria trajectory across projections. Kymographs generated in a x-y dimension (distance vs time) were used to obtain the slope from which mitochondrial velocity was calculated.

Seahorse Oxygen Respirometry

Oxygen consumption rate (OCR) in WT and hemizygous YAC128 cortical/striatal co-cultures and NSCs was measured using Seahorse XFe-24/96 flux analyzers (Seahorse Bioscience, Billerica, MA, USA) following the manufacturer's instructions. Cortical-striatal primary neurons were cultured in Seahorse XF96 V3 cell culture microplates (Agilent, catalog no: 101085-004) at a density of 20,000 cells/well. NSCs were seeded 30,000 cells/well onto an XF24 cell culture microplate (Agilent, catalog no: 102340-100) coated with Geltrex® and allowed to adhere for 24 h at 37° C. Pridopidine (0.1, 1 and/or 5 µM) was added, when indicated in the graphs, 24 h before the experiment. The sensor cartridge plate was incubated with immersed sensors in a non-CO$_2$ incubator at 37° C. for ~16 h (overnight). Prior to the experiments, cells were washed and incubated with XF assay medium (DMEM; Thermo Fisher Sci., catalog no: D5030) supplemented with glucose (20 mM for neurons; 17.5 mM for NSC), 1 mM pyruvate and 2 mM glutamine (for NSCs only), pH=7.4, at 37° C. The cell medium was aspirated gently to avoid disturbing cell monolayers. Baseline measurements of OCR were sampled prior to sequential injection of mitochondrial complex V inhibitor oligomycin (1 µM; Sigma-Aldrich, catalog no: 75351), protonophore Carbonyl cyanide-4-phenylhydrazone (FCCP) (0.5 µM for neurons and 0.3 µM for NSCs; Sigma-Aldrich, catalog no: C2920) and antimycin A (0.5 µM for neurons and 1 µM for NSCs; Sigma-Aldrich, catalog no: A8674) plus rotenone (0.5 µM for neurons and 1 µM for NSCs; Sigma-Aldrich, catalog no: R8875) to complete inhibit mitochondrial respiration. Accordingly, mitochondrial basal respiration, maximal respiration and ATP production was automatically calculated and recorded by the Seahorse software. Data was normalized for protein levels.

Mitochondrial Membrane Potential

Mitochondrial membrane potential ($\Delta\psi_m$) was assessed in cortical and striatal neurons using the positively changed fluorescent probe TMRM (tetramethylrhodamine methyl ester) (Thermo Fisher Sci., catalog no: T668) and in cortical/striatal co-cultures and lymphoblasts using an equivalent probe, TMRE (tetramethylrhodamine ethyl ester) (Abcam, catalog no. ab113852).

TMRM assay: Cortical and striatal neurons previously treated, when indicated, with pridopidine (0.1 and 1 µM; 24 h) were incubated with 150 nM TMRM (quenching conditions) in Na$^+$ medium for 30 min at 37° C. Under these conditions, retention of TMRM by mitochondria was studied to estimate changes in $\Delta\psi_m$. Basal fluorescence (503 nm excitation and 525 nm emission) was recorded using a microplate reader Spectrofluorometer Gemini EM (Molecular Devices, USA) for 4 min, followed by the addition of 2.5 µM FCCP plus 2.5 µg/mL oligomycin to produce maximal mitochondrial depolarization and mitochondrial probe release. TMRM release was calculated based in the differences in fluorescence before and after addition of oligomycin/FCCP.

TMRE assay: Primary neurons and lymphoblasts in suspension were cultured in 6-well plates. The cells were pretreated with/without pridopidine and hydrogen peroxide (H$_2$O$_2$) as per experimental condition followed by incubation with 25 nM TMRE diluted in complete cell culture media for 15 min at 37° C. Primary neurons were detached from the plate using 0.05% trypsin-EDTA and collected in 10% FBS-containing PBS and centrifuged at 1000 rpm for 5 min. The lymphoblasts also were centrifuged at 1000 rpm for 5 min. The cell pellets were re-suspended in 1% FBS-containing PBS and subjected to FACS analysis using Fortessa Flow cytometer (BD Biosciences) with a PE filter (545 nm).

Measurement of Mitochondrial H$_2$O$_2$ Levels

Coverslip-plated cortical and striatal neurons were pretreated with pridopidine (0.1 and 1 µM) for 24 h and incubated with the Mitochondria peroxy yellow 1 (MitoPY1) probe (8 µM; Tocris Bioscience, catalog no: 4428) in Na$^+$ medium for 30 min at 37° C. After incubation, MitoPY1 was washed out and neurons imaged at 1 min intervals for 30 min using LCI PlanNeofluar/1.3NA 63× lens on a Carl Zeiss Axio Observed Z1 inverted confocal microscope using the CSU-X1M spinning disc technology with Zen Black 2012 software (Zeiss, Jena, Germany). Fluorescence was recorded at 503 nm excitation and enhanced emission at 528 nm (Dickinson, Lin, and Chang 2013). After basal reading for 10 minutes, neurons were stimulated with antimycin A (2 µM). Specific MitoPY1 fluorescence in mitochondria was confirmed after co-incubating cells with MitoTracker Deep Red (300 nM; Thermo Fisher Sci., catalog no: M22426). Fluorescence intensity at each time point was analyzed with FUI using the time series analyzer plugin (v 3.0) (Balaji J. 2007).

NSCs were plated at 30,000 cells/well in 96-well assay plates coated with Geltex® for 24 h at 37° C. Afterwards, NSCs were incubated for another 24 h with 1 µM pridopidine. Prior to acquisition, cells were washed with HBSS (in mM: 137.9 NaCl, 1.3 $CaCl_2$, 0.5 $MgCl_2$-$6H_2O$ 0.4 $MgSO_4$-$7H_2O$, 5.3 KCl, 0.4 $KH_2PO_4$, 4.2 $NaHCO_3$, 0.3 $Na_2HPO_4$, 5.6 D-glucose, at pH 7.4) and incubated for 20 minutes with 10 µM MitoPY1 at 37° C. and 5% $CO_2$. MitoPY1 fluorescence was obtained with a Microplate Spectrofluorometer Gemini EM (Molecular Devices, USA) using wavelength parameters described above. Basal levels were measured for 10-15 minutes followed by exposure to 3 µM myxothiazol (mitochondrial complex III inhibitor. Sigma-Aldrich, catalog no: T5580) and measured for an additional 30 minutes. The results were calculated as RFU per 30,000 cells.

In isolated mitochondria, $H_2O_2$ levels were measured using the Amplex Red-horseradish peroxidase method. Briefly, 5 µg of isolated mitochondria was resuspended in mitochondrial reaction buffer (MRB, in mM: 100 sucrose, 100 KCl, 2 $KH_2PO_4$, 5 HEPES, 0.01 EGTA, 3 succinate, 3 glutamate, 0.1 ADP-K, pH 7.4) supplemented with 10 µM Amplex Red reagent (Thermo Fisher Sci., catalog no: A12222) and freshly prepared 0.5 units/mL horseradish peroxidase (Sigma-Aldrich, catalog no: 77332). The homogenate was then dispensed into a 96-multiwell plate and fluorescence was measured in a spectrofluorometer microplate reader by excitation at 570 nm and emission at 585 nm every 30 s, for 20 min. After 10 min of basal reading, mitochondria were challenged with antimycin A (2 µM). Results were analyzed as time-dependent changes in fluorescence.

CellROX Assay $H_2O_2$ (9.8 M stock) was dissolved in cell culture medium prior to experimentation. Primary neurons and lymphoblasts cultured on PDL-coated plates were treated with $H_2O_2$ (0-1 mM) for up to 6 hours. Oxidative stress was measured using the CellROX red reagent (Life Technologies, catalog no. C10422). Cells were treated with 5 µM CellRox red in complete medium, then incubated for 30 minutes. The cells were then washed with PBS and imaged on a Zeiss Axiovert inverted microscope (Zeiss, Jena, Germany) using a 10× objective. Exposure settings were maintained for all samples. Eight random fields were sampled, and the fluorescence intensity was measured using ImageJ software and normalized to the DAPI signal.

MTS Assay

Cell viability was assessed on lymphoblasts using the MTS assay, a measure of mitochondrial function and cell survival. The assay was performed according to the manufacturer's instructions (Promega, catalog no. G1112). Control and HD lymphoblasts were treated with 5 µM pridopidine and 0.1 mM $H_2O_2$ as indicated in figure legends. In the day of experiment, MTS reagent was added to the culture media (1:10) and incubated at 37° C. for 4 hours. Then, lymphoblasts were centrifuged at 145×g for 5 min and media was collected. The absorbance of the formazan dye produced by viable cells was quantified in the medium at OD=490 nm.

Immunoblotting

Cells were homogenized in RIPA buffer (50 mM Tris-HCl pH 7.4, 150 mM NaCl, 0.5% sodium deoxycholate, 1% Triton X-100, 0.1% SDS, 1 mM EDTA, 2 mM sodium orthovanadate, 50 mM sodium fluoride, 1 mM PMSF, 10 µg/ml aprotinin, and 10 µg/ml leupeptin). The cell lysates were transferred to microtubes and incubated for 30 min on ice, then centrifuged at 20,800×g for 15 min at 4° C. Proteins (25-50 µg cell lysate) were resolved by SDS-PAGE and transferred to a polyvinylidene difluoride membrane, which was then blocked for 1 h at room temperature in Odyssey blocking buffer diluted 1:1 with PBS. The membranes were probed overnight at 4° C. with the relevant primary antibodies followed by three washes with 0.1% Tween in PBS (PBST), and re-probing with appropriate fluorescently tagged secondary antibodies. After three washes with PBST, the membranes were scanned and quantified using an Odyssey fluorescent scanner (LICOR Biosciences).

Antibodies used for immunoblotting analysis include anti-rabbit Nrf2 (Cell signal tech, #12721, 1:1000), anti-mouse S1R (Santa Cruz Biotech, SC-137075, 1:500), and anti-mouse actin (Sigma-Aldrich, A5441, 1:20,000).

Gene Expression Analysis by qRT-PCR

RNA extraction and qRT-PCR procedures were performed as previously described (Ehrnhoefer et al. 2018). Briefly, RNA was extracted from cultured lymphoblasts using PureLink mini RNA extraction kit (Thermo Fisher Sci., catalog no: 12183018A). RNA (500 ng) was reverse transcribed using SuperScript II Reverse Transcriptase (Thermo Fisher Sci., catalog no: 18080093) according to manufacturer's instructions. The qPCR was performed using the ABI Prism 7500 Sequence Detection System (Applied Biosystems). Each sample was run in triplicate. Gene expression was normalized to Rpl13a or UBC mRNA.

In Vivo Study Design 1.5-month-old WT and hemizygous YAC128 mice (males and females in equal proportion) were divided into four groups. One WT mice group and one YAC128 mice group received pridopidine treatment (30 mg/kg dissolved in a volume of 100 µL/25 g), whereas the two remaining groups received an equivalent volume of vehicle (sterile water) by oral gavage for 45 consecutive days, until 3 months of age. Mice were divided 4 animals per cage enriched in corn-husk nesting material and paper rolls, each cage representing one individual experiment, for a total of 9 animals per group. Pridopidine was dissolved in deionized sterile water. Animals were weighed every week and the volume of treatment adjusted accordingly. Mice were behaviorally tested in rotarod immediately before commencing treatment and on the day before finishing treatment. Tests were conducted blindly at a set time during the day. Mice were sacrificed 24 h after administration of the final pridopidine dose, and mitochondria isolated from the striatum.

Rotarod Analysis

Motor learning and coordination were assessed on a rotarod apparatus (Letica Scientific Instruments, Panlab, Barcelona, Spain). Mice were allowed to adapt to the behavior room for 2 h before the behavior studies. Procedures were consistent for all subjects and tests made at minimal noise levels. The training phase consisted of four trails per day (120 s each) at 1-hour intervals, at a fixed speed of 14 rpm. In this test, mice must learn to run when placed on a constant rotating rod to prevent them from falling. Once the task is learned, the accelerating rotarod can be used to assess motor coordination and balance. The testing phase was carried out the following day on an accelerating rotarod from 4 to 40 rpm over 5 minutes and consisted of 3 trials, spaced 2 hours apart. Rotarod scores are the average of 3 trials. Experiments were performed blinded for genotype and treatment.

Isolation of Functional Mitochondria

The striatum was dissected from mouse brains washed once in ice-cold mitochondria isolation buffer (MIB: in mM, 225 mannitol, 75 sucrose, 1 EGTA, 5 HEPES-KOH, pH 7.2). Striatal mitochondria were isolated using discontinuous Percoll density gradient centrifugation as previously described (Ferreira et al. 2018). Briefly, striata were transferred to a 7 mL Dounce tissue grinder (Kontes Glass Co., Vineland, NJ, USA) and homogenized 8 times in 0.8 mL MIB supplemented with 1 mg/mL fatty acid free BSA using pestle with 0.07-0.12 mm clearance, followed by another 8 strokes with a pestle with 0.02-0.056 mm clearance. The final homogenate was then centrifuged at 1,100×g for 2 min, at 4° C. The supernatant was collected and mixed with freshy made 80% Percoll (GE Healthcare, catalog no. 17-5445-02) prepared in mitochondrial dilution buffer (MDB: in mM, 1000 sucrose, 50 HEPES-KOH, 10 EGTA, pH 7.0), to create a 5% Percoll solution, which was further carefully layered on the top of freshly made 10% Percoll (diluted from 80% Percoll in MIB). The mitochondrial fraction was pelleted by centrifugation at 18,500×g for 10 min at 4° C. The pellet was then resuspended in 1 mL of mitochondria washing buffer (MWB: in mM, 250 sucrose, 5 HEPES-KOH, 0.1 EGTA, pH 7.2) and centrifuged at 10,000×g for 5 min at 4° C. Mitochondrial pellet was again resuspended in a small volume of ice-cold MWB, to create a concentrated mitochondria solution, and kept on ice for further analysis for a maximum of 2 hours. Protein content of isolated mitochondria was quantified by Bio-Rad assay (Bio-Rad, catalog no. 5000006).

Mitochondrial Complex Activity

Five µg of isolated mitochondria diluted in mitochondrial assay solution (MAS: in mM, 70 sucrose, 220 mannitol, 10 $K_2HPO_4$, 5 $MgCl_2$, 1 EGTA, 2 HEPES-KOH) supplemented with 0.2% (w/v) fatty acid-free BSA, 10 mM pyruvate, 2 mM malate and 4 µM FCCP, were seeded in poly(ethylene-imine)-coated (1:15,000; Sigma-Aldrich, catalog no. 03880) XF24 seahorse plates by centrifugation at 2,000×g for 18 min, at 4° C. (Rogers et al. 2011; Ferreira et al. 2018). After centrifugation, the volume was adjusted to 450 µL and the Seahorse plate was equilibrated in a humidified C02-free incubator at 37° C. for 10-12 min. Sequential electron flow through of the electron transport chain was evaluated after sequential injection of succinate (10 mM; complex II substrate), antimycin A (4 µM; complex III inhibitor) and ascorbate/TMPD (N,N,N',N'-tetramethyl p-phenylenediamine) (10 mM/100 µM; electron donors to cytochrome C/complex IV)(Rogers et al. 2011; Ferreira et al. 2018).

Statistical Analysis

Results are expressed as mean t SEM (standard error of the mean) of the number of independent experiments or animals indicated in figure legends. Comparisons between multiple groups were performed by non-parametric one-way analysis of variance (ANOVA) using the Kruskal-Wallis test followed by Dunn multiple comparison test. Correction for multiple comparisons was done by two-way ANOVA followed by Tukey's post-hoc test. Comparison between two groups was performed by non-parametric Mann-Whitney test. The F-test was performed to analyze the interaction term. Outliers were detected using ROUT method (Q=1%). Significance was accepted at p<0.05. All analyses were performed using Prism software (GraphPad Version 8.0).

Example 2

Figure 1B:
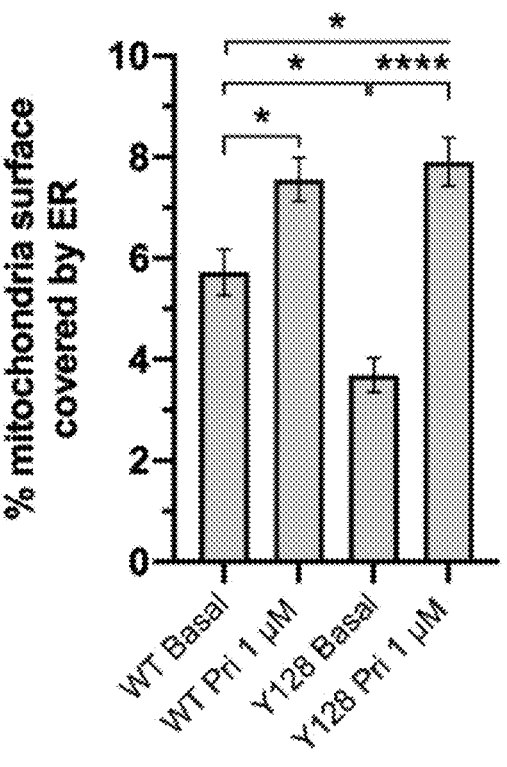
Figure 1C:
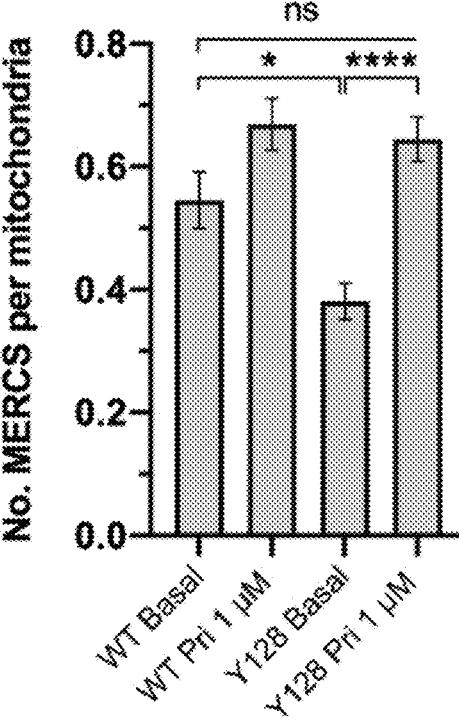
Figure 1D:
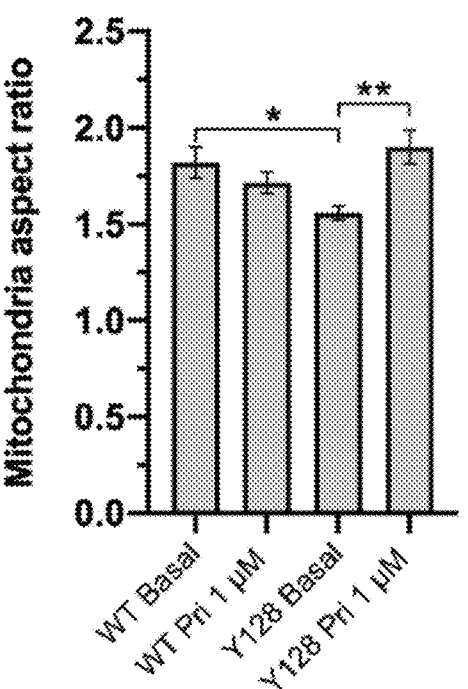

Pridopidine Promotes Mitochondria-ER Tethering and Stimulates Mitochondrial Dynamics and Respiration in HD Neuronal Models Mitochondria-ER contact sites are an important signaling platform. These tethering sites between mitochondria and ER control the amount of $Ca^{2+}$ that is buffered into mitochondria, impacting mitochondrial function, i.e. the activity of Krebs cycle enzymes, mitochondrial respiration and ROS production. Mitochondria-ER contact sites (MERCS) are disrupted in several neurodegenerative disorders (Rossi, Pizzo, and Filadi 2019). YAC128 (Y128) HD striatal neurons show a decreased number of mitochondria-ER contact sites (MERCS) per mitochondria (p=0.0274). The percent of mitochondrial surface covered by ER is also reduced compared to WT neurons (p=0.0141) (FIGS. 1A-1C). Concordantly, co-localization of $IP_3R3$, and S1R with mitochondria is reduced by ~40% in HD neurons (p=0.049 for $IP_3R$; p=0.0008 for S1R) (FIGS. 1F-1H). Thus, mitochondria-ER contact sites are decreased in neurodegenerative disease (e.g., HD (p=0.0329) (FIGS. 1A, 1E).

Mitochondrial morphology can also provide insight into mitochondrial function and is impaired in HD. Y128 neurons show a reduced aspect ratio (p=0.0343) (FIG. 1D, FIG. 1F), indicating a higher proportion of fragmented mitochondria. Changes in mitochondrial morphology indicate alterations in mitochondrial fusion and fission, which enable transport along the axon without affecting trafficking (Cherubini, Lopez-Molina, and Gines 2020; Lewis et al. 2018).

Pridopidine treatment (1 µM) restores the deficient mitochondria-ER connectivity in YAC128 striatal neurons by increasing the number of MERCS per mitochondria and the percent of mitochondrial surface in contact with ER (p<0.0001). Pridopidine additionally increases the proportion of elongated mitochondria in Y128 striatal neurons to WT levels (p=0.0044) (FIGS. 1A-1D, FIG. 1F). The increase in $IP_3R$ and S1R co-localization with mitochondria prompted by pridopidine treatment in Y128 neurons (p=0.0001 for $IP_3R$; p<0.0001 for S1R) suggests that pridopidine restores this important signaling platform. (FIGS. 1F-1H). Total S1R protein levels are also reduced in Y128 striatal neurons, and pridopidine treatment restores S1R levels to WT levels (FIG. 9).

Figure 1E:
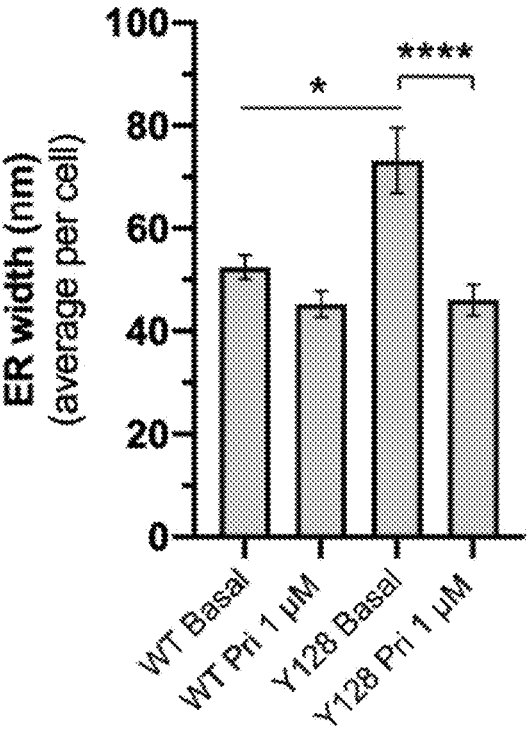
Figure 1F:
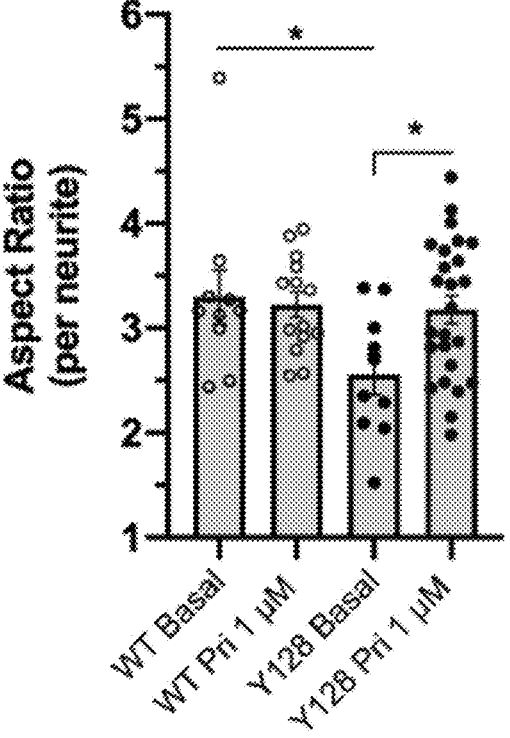
Figure 1G:
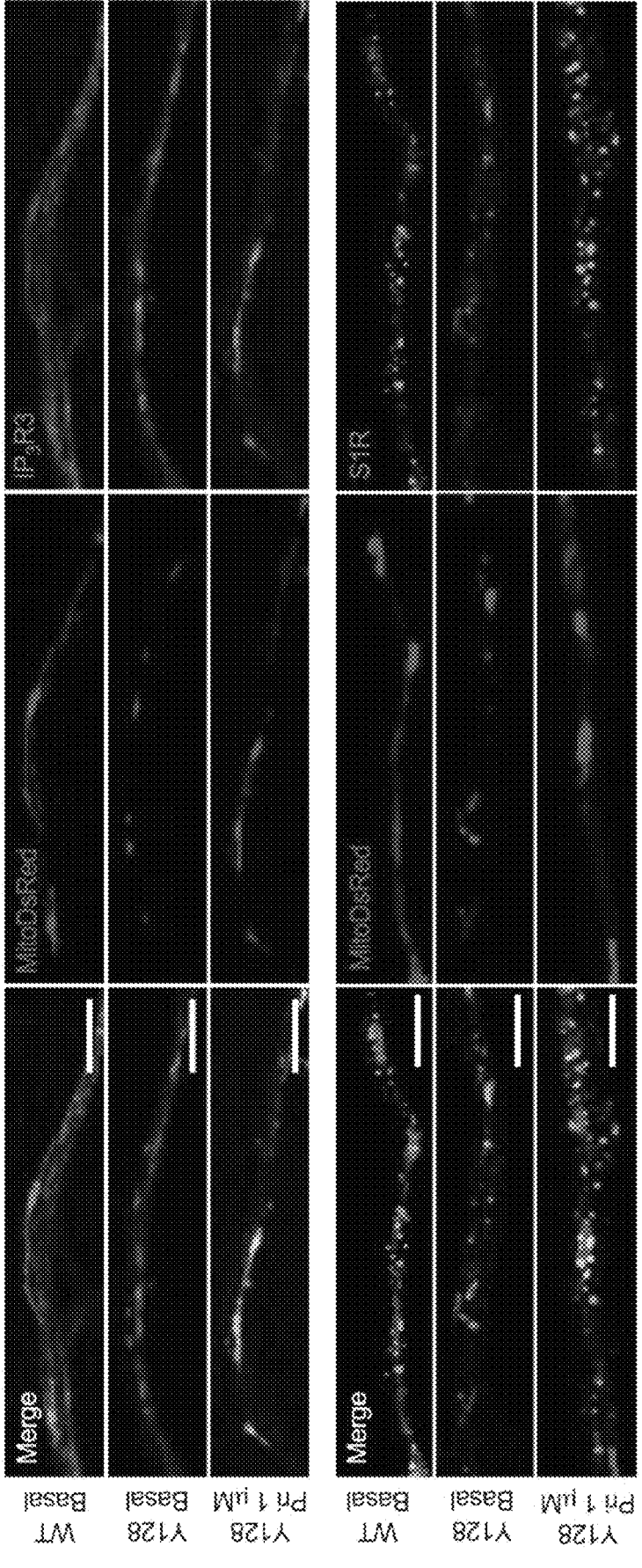

Furthermore, pridopidine restores the abnormal ER width observed in YAC128 neurons (p<0.0001) (FIG. 1E). In WT neurons, pridopidine also significantly increases the percent of mitochondrial surface in contact with ER (p=0.0339) (FIG. 1B).

Mitochondrial trafficking is necessary for nourishing high energetic demands in synaptic terminals and is therefore an indicator of proper mitochondrial function. YAC128 striatal neurons show decreased mitochondrial anterograde transport with approximately 90% of mitochondria in stationary phase (p=0.0169) (FIGS. 2A, 2B). Pridopidine treatment (1 µM) significantly increases the proportion of motile mitochondria (p=0.0286), re-establishing both anterograde and retrograde transport (FIGS. 2A-2B). Moreover, motile mitochondria in YAC128 neurons move at half the velocity of wild-type neurons (p=0.0218). This decrease was ameliorated following pridopidine treatment (1 µM) (p<0.05) (FIGS. 2A, 2C).

Y128 neurons show reduced basal and maximal respiration as well as compromised ATP production (FIGS. 3A-3D). Reduced respiration can be a result of the impaired mitochondrial dynamics and morphology demonstrated in HD neurons (FIGS. 1A-IK and 2A-2C). Treatment with pridopidine at 1 and 5 μM doses rescues maximal (p=0.0061 for 1 μM Pri, p=0.002 for 5 μM Pri) respiration in HD Y128 corticostriatal neurons, as well as ATP production (p=0.0358 for 5 μM Pri). Pridopidine shows a non-significant trend towards increasing basal respiration. (FIG. 3B (basal), FIG. 3C (maximal), FIG. 3D (ATP production). Pridopidine 1 μM also increases basal (p<0.001) and maximal (p<0.05) mitochondrial respiration, as well as ATP production in human iPSC-derived neural stem cells (NSCs) from a heterozygous HD patient (HD-iPSC) In WT neurons pridopidine enhances mitochondrial basal respiration (p=0.0058 for 1 μM Pri, p=0.0016 for 5 μM Pri) and ATP production (p=0.02 for 5 μM Pri) (FIGS. 3B, 3D). Pridopidine also increases mitochondrial basal (p=0.0043) and maximal respiration (p=0.0177) and shows a trend towards increasing ATP production in human iPSC-derived neural stem cells from a HD patient (HD-NSCs) (FIGS. 3E-3H).

Example 3

Early Pridopidine Treatment Rescues Mitochondrial Function in HD Cells

Mitochondrial membrane potential (MMP, $\Delta\Psi_m$) directly affects ATP production and is affected by mitochondrial $Ca^{2+}$ signaling. Y128 cortical and striatal neurons from two Y128 lines, expressing low and high levels of mHtt were assessed. Y128 cortical neurons exhibit lower MMP as a result of oligomycin and FCCP-induced mitochondrial dysfunction compared to wild-type cortical neurons (p<0.05), indicated by lower mitochondrial retention of TMRM observed by decreased fluorescence after complete mitochondrial depolarization with oligomycin and FCCP (p=0.0193 vs Y128 low; p=0.0222 vs Y128 high) (FIGS. 4A, 4B). In striatal neurons, here is a trend towards a reduction (FIG. 4C). Pridopidine (0.1 and 1 μM) significantly increases MMP in Y128 cortical and striatal neurons expressing both high and low levels of mHTT (Y128 high: p=0.015 for 0.1 μM Pri and p=0.0201 for 1 μM Pri in Ct neurons; p=0.0407 for 0.1 μM Pri and p=0.0017 for 1 μM Pri in St neurons. Y128 low: p=0.0008 for 0.1 μM Pri, and p=0.0303 for 1 μM Pri in Ct neurons; p=0.0274 for 0.1 μM Pri in St neurons) (FIGS. 4A-4C). These results indicate that the effect of pridopidine on mitochondrial function is independent of mHTT expression levels. In WT striatal neurons, 1 μM pridopidine also increases MMP (p=0.0013) (FIG. 4C).

Hydrogen peroxide ($H_2O_2$) was used as a more potent oxidative stimulus to evaluate MMP. Y128 neurons exposed to 0.1 mM $H_2O_2$ for 6 h show ~30% MMP compared to untreated (p<0.0001). Pridopidine 5 μM treatment administered 24 hours before the cytotoxic $H_2O_2$ stimulus completely reverts this $H_2O_2$-induced loss of MMP (p=0.001), showing MMP levels similar to Y128 neurons unchallenged by $H_2O_2$ (comparing the two right bars) (FIG. 4D).

A dose-response experiment in human lymphoblasrs shows that pridopidine demonstrates the characteristic dose-response bell shaped curve associated with S1R agonists, with the maximal effect achieved at 5 μM. Lymphoblasts were first treated with pridopidine for 24 h followed by an oxidative stimulus of 6 h with 0.1 mM $H_2O_2$. A higher dose of pridopidine (10 μM) is less efficacious and shows less restoration of membrane potential (p=0.1389)(FIG. 4E).

The recovery of mitochondrial function observed when pridopidine treatment is administered prior to $H_2O_2$ stimuli, is accompanied by a significant increase in cell viability of approximately 50% (p=0.0016) (FIG. 4F).

Example 4

Pridopidine Ameliorates Reactive Oxygen Species Production and Antioxidant Defense in HD Cell Models Higher susceptibility of mitochondria from Y128 neurons and HD lymphoblasts to $H_2O_2$ suggests that these cells exhibit increased oxidative stress. To test this, local $H_2O_2$ flux was measured with the fluorescent probe MitoPY1. The complex III inhibitor Antimycin A (AntA), which induces reactive oxygen species (ROS) production, stimulated mitochondrial dysfunction in cortical (p<0.01) and striatal (p=0.0001) YAC128 (Y128) neurons to show a significant 2-fold increase in mitochondrial-driven $H_2O_2$ levels compared to WT neurons. In both cortical and striatal neurons 1 μM pridopidine reverted the increased levels of mito-$H_2O_2$ prompted by AntA (p<0.0001 in cortical neurons, p<0.01 for 0.1 μM and p<0.0001 for 1 μM in striatal neurons) (FIGS. 5A-5C).

HD neuronal stem cells (NSCs) treated with the mitochondrial complex III inhibitor, myxothiazol (Myxo, 3 μM) show a large increase in mito-$H_2O_2$ levels compared to control NSCs (p=0.0365) (FIG. 5D). HD lymphoblasts also present a 3-fold increase in CellRox fluorescence, a different measure of mitochondrial ROS production, in response to $H_2O_2$ challenge (p=0.0206) (FIG. 5E). Pridopidine efficiently decreases ROS levels in all three cellular HD models assessed. In both cortical (FIG. 5B) and striatal (FIG. 5C) neurons, pridopidine reverts the increased levels of mito-$H_2O_2$ prompted by Ant A (4B; p<0.0001) (4C; p=0.0005 for 0.1 μM Pri, p<0.0001 for 1 μM Pri). In HD-NSCs, 1 μM pridopidine reduces (~42%) the observed increase in $H_2O_2$ levels induced by complex III inhibition (p=0.0075) (FIG. 5D). In HD lymphoblasts, pridopidine treatment (5 μM) decreases ROS levels by 57% under $H_2O_2$-challenged conditions (p=0.0001) (FIG. 5E).

The S1R modulates oxidative stress through activation of nuclear factor erythroid 2-related factor 2 (Nrf2) signaling and the downstream antioxidant response element (ARE) genes.

Impaired expression of the ARE genes downstream to Nrf2 suggest an impaired stress response in HD cells (Pal et al. 2012; Ribeiro et al. 2014), explaining the observed increase in ROS production (FIG. 5E). The expression of three Nrf2-ARE pathway-regulated genes: NAD(P)H dehydrogenase [quinone]1 (Nqo1), heme oxygenase 1 (Hmox1) and glutamate-cysteine ligase catalytic subunit (GCLc) demonstrate decreased mRNA levels in HD lymphoblasts (FIGS. 5F-5H). Two of the analyzed genes show significantly reduced mRNA expression in HD lymphoblasts (p=0.0372 for Ngo1 and p=0.0463 for Hmox1) and a trend for reduced mRNA levels of GCLc (p=0.0918). Pridopidine treatment significantly upregulates the expression of Nqo1 (p=0.0010) and Hmox1 (p=0.0308), and shows a trend towards upregulation of GCLc expression. These data support the role of pridopidine in regulating oxidative stress.

Example 5

The Beneficial Effects of Pridopidine on HD Mitochondria are Mediated by the S1R To further confirm that the effects of pridopidine are mediated by the S1R, the S1R was silenced in HD lymphoblasts by reducing protein levels by approximately 83% (FIGS. 6A, 6B). MMP was evaluated by TMRM, and oxidative stress was evaluated with CellRox staining. In S1R+/+ neurons, pridopidine treatment increases TMRM signal after $H_2O_2$ stimulation. In the absence of the S1R, the effect of pridopidine on mitochondrial membrane potential is abolished (p<0.0001) (FIG. 6C), indicating that pridopidine effects on mitochondrial functions are S1R-dependent.

Example 6

Early Pridopidine Treatment in YAC128 Mice Delays Onset of Motor Deficits and Regularizes Mitochondrial Abnormalities The neuroprotective effect of pridopidine was reproduced in vivo. WT and YAC128 mice at 1.5 months of age (pre-symptomatic) began treatment with either 30 mg/kg/day pridopidine or vehicle (sterile water) by oral gavage for 45 days (until 3 months of age; early symptomatic)(FIG. 7A). YAC128 mice exhibit motor deficits at 3 months of age in the rotarod performance test (Van Raamsdonk et al. 2005), therefore this test was applied before and after pridopidine treatment. At 1.5 months (pre-treated) Y128 mice displayed the same motor coordination as wild-type mice (FIG. 7B). At 3 months of age, vehicle-treated Y128 mice showed motor deficits compared to vehicle-treated wild-type mice, as observed by a reduced latency to fall during the accelerated rotarod test (p=0.0471) (FIG. 7C). Conversely, HD mice treated with pridopidine exhibit a significant motor improvement in the accelerated rotarod, compared to vehicle-treated HD mice (p=0.0270) (FIG. 7C).

After behavior analysis, functional mitochondria were isolated from striatum of all mice groups, and mitochondrial complexes activity was assessed by evaluating sequential electron flow through the electron transport chain by measuring OCR following sequential injections of succinate, antimycin A and ascorbate/TMPD (N,N,N',N'-tetramethyl p-phenylenediamine) that induced individual stimulation or inhibition of mitochondrial complexes II, III and IV, respectively, allowing the calculation of their activities (FIG. 7D) (Ferreira et al. 2018). Striatal mitochondria from vehicle-treated YAC128 mice show significantly higher activity of complexes II (p=0.0016) (FIG. 7E), III (p=0.0021) (FIG. 7F) and IV (p=0.0010) (FIG. 7G) compared to vehicle-treated wild-type mice, suggesting an early compensatory mechanism.

Increased complex activities in YAC128 HD mouse striatal cells is accompanied by increased mitochondrial $H_2O_2$ production, as measured by resorfin fluorescence (FIGS. 7H-7J) before (FIG. 7I) and after (FIG. 7J) inhibition of complex III with antimycin A (p=0.0276 in J; p=0.0219 in K). These results suggest that abnormal mitochondrial ROS production along with abnormal complex activity may underlie the HD mitochondrial phenotype. In vivo pridopidine treatment in YAC128 mice normalizes the activity of mitochondrial complexes H and III (p=0.0306 and p=0.0084, respectively) (FIGS. 7E, 7F). Pridopidine treatment also hinders the observed increase of $H_2O_2$ in HD mitochondria (FIGS. 7H-7J) Pridopidine treatment does not affect mitochondrial complex activities and $H_2O_2$ levels in wild-type mice.

Together, these data demonstrate neuroprotective effects of pridopidine in vivo in HD mice and suggest that regulation of oxidative stress is a key factor in the beneficial effect of pridopidine on mitochondrial function.

Discussion

Impaired ER-mitochondria connectivity, as is demonstrated in HD neurons, extensively disturbs mitochondrial respiration and ATP production. Pridopidine treatment significantly restores the mitochondria-ER connection, as well as mitochondrial and ER structure and function in YAC128 HD neurons, to WT levels. Pridopidine restoration of mitochondrial-ER coupling contributes to the protective effects of pridopidine on synaptic plasticity (Smith-Dijak et al. 2019) and spine density in HD models.

The data presented above show that pridopidine improves mitochondria-ER interaction in HD cells, and as a result many events that lie downstream to these contacts. These include enhancing mitochondrial respiration and ATP production, mechanisms highly regulated by $Ca^{2+}$ influx through the mitochondrial $Ca^{2+}$ uniporter (Niescier et al. 2018) (FIG. 9). Furthermore, pridopidine effectively reduces ROS levels via S1R activation in HD neural cells, human lymphoblasts and in adult YAC128 mouse mitochondria. Moreover, pridopidine treatment restores abnormal mitochondrial complex activity and $H_2O_2$ production and maintains motor capabilities of YAC12 HD mice. The protective effects of pridopidine are mediated via activation of the S1R as deletion of S1R expression abolishes them.

Pridopidine Mediates Regulation of Redox Status and Cell Survival Through S1R

Increased production of ROS and changes in redox homeostasis are major contributors to cellular death. Mitochondria are the primary source of ROS since about 1% of $O_2$ consumed generates superoxide anion due to the leakage of electrons at complexes I and III.

The observed multifaceted rescue of mitochondrial function by pridopidine at the cellular level translates to a beneficial effect in vivo. Treatment of pre-symptomatic YAC128 HD mice with pridopidine significantly improves their performance in the rotarod test, implying a delay in the onset of motor symptoms. This improved performance is likely to result from maintenance of neuronal function.

Conclusions

Modulation of S1R function has significant therapeutic potential due to its involvement in mitochondria-ER tethering and multiple downstream effects (FIG. 9 Rows A and B). In this study, we show that S1R activation by pridopidine rescues multiple mitochondrial functions, potentially contributing to the overall neuroprotective effect of pridopidine observed in preclinical and clinical studies.

Example 7

Materials and Methods-2

Materials

Tunicamycin (Cat.No. T7765), thapsigargin (Cat.No. T9033), puromycin (Cat.No. P8833), phosphatase inhibitor cocktail 2 (Cat.No. P5726) and 3 (Cat.No. P0044), trypan blue solution (Cat.No. T8154), and other common reagents were from Sigma. Protease inhibitor cocktail (Cat.No. 000000011873580001) was from Roche Applied Science. Pridopidine was from Prilenia (Israel).

Plasmids and Constructs:

Myc-tagged exon 1 Htt20Q and Htt96Q are subcloned into pTREhygro vectors controlled by pTet-Off regulatory plasmid, but all experiments were done in the absence of tetracycline or doxycycline, with expression on. Sigma-1R-YFP was a kind gift of Teruo Hayashi. H2a-GFP, Htt20Q cherry and Htt96Q cherry were as previously described (Leitman, Ulrich Hartl, and Lederkremer 2013).

Guide RNAs (gRNA) in PLV-U6g-EPCG lentiviral vector targeting human Sigma1-R (Cat.No. HS0000322318, HS0000322320 and HS0000322323) and a construct with a control gRNA (Cat.No. CRISPR12-IEA) were from Sigma-Aldrich. The vectors contain also the Cas9 gene and a selection marker.

Antibodies:

Rabbit anti-S1R receptor antibody (RRID:AB_2042518) for immunofluorescence staining was from Abcam and mouse anti-S1R (RRID:AB_2285870) for immunoblot from Santa Cruz. MitoTracker deep red FM (Cat.No. 8778), mouse anti-eIF2α (RRID:AB_836874), anti-CHOP (RRID:AB_2089254) and anti-myc (RRID:AB_331783) were from Cell Signaling (Beverly, MA); rabbit anti-P-eIF2α (RRID:AB_843062) from MBL, anti-GADD34 (RRID:AB_2237472) was from Santa Cruz and anti-ATF6 (RRID:AB_1019028) from Abnova. Mouse anti-GAPDH (RRID:AB_2107445) was from Chemicon International, anti-β-tubulin (RRID:AB_609915) and anti-actin (RRID:AB_262137) were from Sigma. Goat anti-rabbit IgG antibody conjugated to Cy3 (RRID:AB_2338006), goat anti-mouse IgG antibody—Cy2 (RRID:AB_2338746), goat anti-mouse IgG-DyLight549 (Cat.No. 115-505-062), goat anti-rabbit (RRID:AB_2307391) and anti-mouse IgG (RRID:AB_2338511) conjugated to HRP, were from Jackson ImmunoResearch (West Grove, PA). Goat anti-rabbit (RRID:AB_10680870) and goat anti-mouse IgG conjugated to DyLight650 (RRID:AB_1067931) were from Abcam.

Cell Culture, Media, and Transfections:

HEK 293 and NIH 3T3 cells (ATCC) were grown in DMEM supplemented with 10% bovine calf serum at 37° C. under 5% CO2. Transfections of HEK 293 cells were carried out according to the calcium phosphate method. STHdh$^{Q7/7}$ cells are a murine striatal cell line with a stable knock-in of the full-length wild type (WT) human Htt containing a polyglutamine stretch of 7 glutamines (Trettel et al. 2000). They were grown as before, at 33° C. in DMEM (Cat. No. 41965-039) (Gibco) plus 10% FCS (Cat. No. 04-007-1A) (Biological Ind., Israel), up to passage 20. No cell line used is listed as a commonly misidentified cell line. Cell lines were not authenticated. To reduce any risk of cross-contamination they were grown for a limited number of passages. Transient transfections of NIH 3T3 and STHdh$^{Q7/7}$ cells were performed using an MP-100 Microporator (Digital Bio) or ViaFect™ Transfection Reagent (Cat.No. E4981) (Promega), according to the manufacturer's protocols.

Htt96Q or Htt20Q expression plasmids were cotransfected with tetracycline-controlled pTet-Off regulatory plasmid at 1:3 ratio in all cases. To determine cell viability, transfected and treated cells were trypsinized and stained with 0.4% trypan blue solution 1:1 for 3 min at room temperature. The viability was assessed by counting white (live) and blue (dead) cells in a hemocytometer.

Production of S1R Knockout and Control HEK 293 Cells:

HEK 293 cells were transfected with plasmids carrying Cas9 and 3 different guide RNAs (gRNA) targeting human Sigma1-R and a control gRNA. Ten days after transfection and selection with puromycin, cell lysates of the pools of selected cells were tested for S1R knockout by immunoblotting. The results showed a high efficiency of the knockout for the 3 gRNAs tested. Subsequent cloning by dilution produced, after 4 weeks, several clones with complete knockout of Sigma1-R for each gRNA.

Primers and Real-Time PCR:

Total cell RNA was extracted with TRIzol reagent (Invitrogen) according to the manufacturer's instructions. Reverse transcription (RT) was performed with QuantaBio qScript cDNA synthesis kit (Cat.No. 95047-100). Real-time PCR was carried out using a CFX Connect Real-Time PCR Detection System (BioRad) and the amplifications were done using the SYBR Green PCR Master Mix (Cat.No. pb089617-100-1) (Pcrbio). Reactions were run in triplicates in three independent experiments. Housekeeping gene GAPDH was used as an internal control to normalize the variability of expression levels.

Primers for spliced XBP1 amplification were 5'-TGCT-GAGTCCGCAGCAGGTG-3' (SEQ ID NO: 1) and 5'-GCTGGCAGGCTCTGGGGAAG-3' (SEQ ID NO: 2), for S1R 5'-TGGGCTGAGATCTCGGATAC-3' (SEQ ID NO: 3) and 5'-AGGCCCGTGTACTACCGTCT-3' (SEQ ID NO: 4) and for GAPDH 5'-CCACATCGCTCAGACAC-CAT-3' (SEQ ID NO: 5) and 5'-CAACAATATCCACTT-TACCAGAGTTAA-3' (SEQ ID NO: 6).

Cell Lysis and Immunoblotting:

Cells were lysed in PBS containing 1% Triton X-100, 0.5% sodium deoxycholate with protease inhibitors and centrifuged to pellet insoluble aggregates, debris and nuclei. Phosphatase inhibitor cocktail 2 and 3 and 10 mM 0-glycerol phosphate were added to the lysis buffer to inhibit phosphatases for detection of phosphorylated proteins. Supernatants were separated from pellets and incubated in loading buffer for 5 min at 100° C., pellets were incubated for 10 min at 100° C. After SDS-PAGE and transfer to nitrocellulose membrane, blocking was done in 5% low-fat milk and 0.1% Tween-20 in PBS for 1 h. Incubation with the primary antibody was overnight at 4° C. and after three washes in 0.1% Tween-20 in PBS, incubation with the appropriate secondary antibody was for 1 h at room temperature. After washing, enhanced chemiluminescence assay was performed and the membrane was exposed and quantified in a Bio-Rad ChemiDocXRS Imaging System (Bio-Rad, Hercules, CA).

Filter Trap Assay:

HEK 293 cells were grown on 60 mm plates and transfected for the expression of myc-Htt96Q. Cells were collected 24 hours post-transfection. After washing with 1×PBS cells were resuspended in 100 μl of 1×PBS+ protease inhibitor cocktail. Sonication was done in a sonic bath for 3×10 sec (amp5-6), leaving on ice for 30 sec between the sonications. Cell debris were removed by centrifugation at 16,000×g for 15 min and protein concentration was measured in the supernatant using the BCA method. Samples containing 50 μg total protein were taken and the volume adjusted to 100 μl with 1% SDS in PBS. After incubation for 5 min at 100° C. sample duplicates were loaded on the slots of a nitrocellulose membrane pre-wet with 1% SDS in PBS in a dot-blotting apparatus. Slots were washed twice with 1 ml 1% SDS in PBS and the membrane was transferred to 5% milk blocking solution. Immunoblotting was performed as described above.

Immunofluorescence Microscopy and Fluorescence Quantification:

Briefly, cells grown for 24 h after transfection on coverslips in 24-well plates were fixed with 3% paraformaldehyde, followed by blocking with 50 mM glycine in PBS and normal goat IgG in PBS/2% BSA. The cells were incubated with primary antibodies for 1 h, washed and incubated for 30 min with secondary antibodies, followed by washes. Nuclei were stained with 4',6-diamidino-2-phenylindole (Cat.No. F6057) (Sigma). Confocal microscopy was done on a Zeiss laser scanning confocal microscope (LSM 510; Carl Zeiss, Jena, Germany) as described previously. ImageJ was used to quantify fluorescence intensity in images of treated individual cells compared to untreated cells with and without Htt96Q-mCherry aggregates and to calculate Mander's coefficients for colocalization studies.

Statistical Analysis:

The results are expressed as average f standard deviation or + standard error as stated. Student's t-test (two-tailed) was used to compare the averages of two groups. No exclusion criteria were pre-determined. The software used was Microsoft Excel 2016 for Mac. No randomization and/or sample size calculation were performed. Data were not assessed for normality. When mentioning "independent experiments" this refers to independent cell preparations. No test for outliers was conducted. Statistical significance was determined at P<0.05 (*), P<0.01 (), P<0.001 (*).

Example 8

Pridopidine Reduces mHtt-Induced ER Stress

The effect of pridopidine on mHtt-induced ER stress. ER stress levels were measured in a murine striatal cell line with a stable knock-in of the full-length wild type (WT) human Htt containing a polyglutamine stretch of 7 glutamines (STHdh$^{Q7/7}$). STHdh$^{Q7/7}$ cells are transfected with either mutant Htt96Q-mCherry or WT Htt20Q-mCherry constructs. When the polyQ-expanded Htt protein (96Q) exon1 fused to fluorescent mCherry protein is expressed, the levels and aggregation of the protein in individual cells can be followed using a fluorescence microscope. Co-expression of the Htt96Q construct with Htt7Q in the striatal cells mimics the typical heterozygous expression of pathogenic mHtt in HD patients. The cells are co-transfected with a plasmid for expression of H2a-GFP, a protein indicator of early stages of ER stress. H2a-GFP is a model misfolded secretory protein which, in response to ER stress, accumulates and concentrates in the juxtanuclear ER-derived quality control compartment (ERQC). Expression of Htt96Q-mCherry induces the expected strong accumulation of H2a-GFP, whereas the WT Htt20Q-mCherry protein has no such effect (FIGS. 10A-10F).

Most cells containing visible mutant Htt96Q-mCherry aggregates (typically one large aggregate per cell) show high levels of accumulated H2a-GFP (FIG. 10B), whereas most cells expressing Htt20Q-mCherry or Htt96Q-mCherry without visible aggregates show low levels of H2a-GFP (FIGS. 10A, 10D).

Pridopidine significantly reduces H2a-GFP accumulation in cells positive for mHtt aggregates, down to 40% of the untreated control, but does not alter H2a-GFP levels in cells without aggregates or in cells expressing Htt20Q-mCherry (FIGS. 10C, 10E). Pridopidine significantly reduces ER stress in a dose-dependent manner (from 0.03 to 150 μM) in cells with Htt96Q-mCherry aggregates (FIG. 10F).

Phosphorylation of eIF2α is a hallmark of ER stress. In HEK293 cells expressing Htt96Q-mCherry, eIF2α-phosphorylation (eIF2α-p) levels increase with time (FIGS. 11A-11B). Pridopidine reduces levels of eIF2α-phosphorylation in a dose-dependent manner (0 to 3 μM), down by 3.6 fold compared to the untreated control at 24 h and to a level close to that in Htt20Q expressing cells. At high doses of 30 and 150 μM, there was no effect of pridopidine on the phosphorylation of eIF2α. These results are consistent with the typical bell-shaped dose response curve for S1R agonists when measuring various cellular parameters. Cells expressing WT Htt20Q show lower levels of eIF2α phosphorylation and are unaffected by pridopidine treatment.

Pridopidine has similar ameliorating effects on eIF2α phosphorylation when the cause for ER stress is not mHtt toxicity. Thapsigargin (TG) treatment to induce ER stress enhances eIF2α-P levels, indicating that the cells undergo ER stress. Pridopidine reduces the TG-induced ER stress as measured by eIF2α-P, down to the levels of untreated cells and in a similar concentration range as in cells expressing Htt96Q and also showing a bell-shaped dose response (FIG. 11C, compare to FIG. 11A). This suggests that pridopidine reduction of ER stress is independent of the presence of mHtt.

Example 9

Elevated eIF2α-P Levels (PERK Pathway) Increase Several Downstream UPR Factors, Including CHOP and GADD34.

CHOP and GADD34 are downstream to eIF2α phosphorylation in the unfolder protein response (UPR) pathway. Both CHOP and GADD34 are increased in cells expressing mutant Htt96Q. Pridopidine treatment reduces CHOP and GADD34 levels by of 2.5- and 7-fold respectively, at 48 h (FIGS. 12A-12B), suggesting an overall reduction of the ER stress. Pridopidine does not affect these factors in cells expressing Htt20Q. Other UPR pathways are moderately reduced by pridopidine in Htt96Q-expressing cells, with a 35% reduction in ATF6 fragment and a 25% reduction in XBP-1s mRNA (IRE1 pathway) at 3 μM pridopidine (FIGS. 12C-12D). This indicates that the most pronounced effect of mutant Htt on ER stress is activation of the PERK branch (Leitman, Ulrich Hartl, and Lederkremer 2013).

Example 10

The Effect of Pridopidine on eIF2α Phosphorylation is Dependent on the Sigma-1 Receptor To assess the role of the S1R in eIF2α phosphorylation, CRISPR/Cas9 technology was used to genetically silence the S1R in HEK 293 cells (FIG. 13A). Lack of S1R (S1R$^{-/-}$) causes an increase of 1.5-fold in the levels of eIF2α-P as compared to S1R expressing control cells (S1R$^{-/-}$), both cell lines expressing Htt96Q. Thus, loss of S1R increases ER stress (FIG. 13B). Pridopidine significantly reduces eIF2α-P levels in the S1R$^{-/-}$ cells expressing Htt96Q, but not in the S1R$^{-/-}$ cells expressing Htt96Q. These results suggest that the reduction of mHtt-induced eIF2α phosphorylation by pridopidine is S1R-dependent.

Example 11

S1R Insoluble Levels and Subcellular Localization

Aggregated Htt96Q affects the subcellular localization of endogenous S1R, similarly to S1R-YFP (FIG. 14A). Treatment with pridopidine for 20 h does not change the pattern of S1R-YFP, which appears similar to untreated cells, in disperse puncta in Htt20Q-mCherry expressing cells and in intense patches in cells with Htt96Q-mCherry (FIG. 14A). However, S1R-YFP levels are further increased in a dose-dependent manner by pridopidine (by up to 47% above the levels in the untreated cells) in the presence of Htt96Q-mCherry but not Htt20Q-mCherry (FIGS. 14A-14B). Pridopidine also increases the Triton-insoluble levels of S1R-YFP (FIG. 14C) and also those of the endogenous S1R (FIG. 14D).

Under normal physiological conditions, the S1R is associated with the ER chaperone BiP. Upon ligand binding and activation, the S1R dissociates from BiP and can modulate the IP3R. Mutant Htt96Q elicits a significant 2-fold decrease in the colocalization of S1R with BiP-GFP (FIG. 15A graph) compared to cells expressing Htt20Q. Similar results are observed in cells expressing BiP-RFP, where pridopidine treatment restores S1R/BiP colocalization in cells expressing Htt96Q aggregates to normal, unstressed levels and similar to the level of colocalization in cells expressing Htt20Q (FIG. 15B graph). Pridopidine does not affect S1R/BiP colocalization in cells expressing Htt20Q.

Altogether, these results suggest that mHtt affects the physical state of the S1R, increases its half-life and redistributes it to non-MAM ER domains, which correlates with S1R/BiP segregation. Pridopidine further increases S1R stability and insolubility, and restores colocalization of S1R and BiP.

Example 12

Pridopidine Increases the Sequestration of mHtt into Protective Insoluble Aggregates in a S1R-Dependent Manner.

Soluble oligomeric forms of mHtt cause ER stress, which is mitigated by mHtt sequestration into large insoluble aggregates. To analyze whether pridopidine reduction of ER stress involves a change in the aggregation status of mHtt, mutant Htt96Q was expressed, and the formation of SDS-insoluble mHtt aggregates in S1R$^{-/-}$ cells and S1R$^{+/+}$ cells was compared using a filter trap assay. Pridopidine increases the amount of Htt96Q in SDS-insoluble aggregates in the S1R$^{+/+}$ cells by up to 35%. Untreated S1R$^{-/-}$ cells show increased levels of Htt96Q in SDS-insoluble aggregates, probably caused by changes in gene expression and cellular metabolism by the long-term absence of S1R. However, the effect of pridopidine was abolished in S1R−/− cells, together with some non-significant decrease in the levels of insoluble aggregates (FIG. 16A). However, the effect of pridopidine was abolished in S1R$^{-/-}$ cells, together with some non-significant decrease in the levels of insoluble aggregates (FIG. 16A). This indicates that the increase of mHtt sequestration into large aggregates by pridopidine is mediated by the S1R. Pridopidine does not alter the existence or not of visible Htt96Q-mCherry aggregates (FIGS. 10A-10F). Indeed, the percent of cells that show visible aggregates after expression of Htt96Q-mCherry for 24 h is unchanged (FIG. 16B). This suggests that pridopidine does not increase the number of cells with large aggregates, but rather induces an increase in recruitment of toxic soluble mHtt oligomers into the insoluble aggregates in each cell.

Discussion

These results suggest that pridopidine activation of the S1R significantly ameliorates mHtt-induced ER stress in cells expressing Htt96Q. In addition to causing ER stress by interference with ER-associated protein degradation, mHtt enhances the sensitivity of IP3R to IP3, resulting in a tonic calcium leakage that decreases ER Ca2+ levels, which is another contributor to ER stress. Pridopidine activation of the S1R modulates IP$_3$R transport of Ca$^{2+}$, which might in turn accelerate mHtt sequestration into much less toxic large aggregates, subsequently reducing ER stress. In YAC128 HD primary neuronal cultures, pridopidine suppresses abnormal ER Ca$^{2+}$ release through its activation of the S1R.

Pridopidine reduces eIF2α-P levels and other UPR markers, consistent with the reduction in ER stress.

The dramatic redistribution in the subcellular localization of S1R to a "patchy" pattern upon expression of mHtt, suggests translocation to a different subcellular compartment. The patchy appearance of S1R is in line with its reorganization into higher order oligomers and consistent with its segregation from BiP in ER subdomains. Pridopidine causes a further increase in the level of S1R, and in the S1R insoluble fraction, but only in the presence of mHtt and not with WT Htt (FIGS. 14A-14D). This is consistent with a requirement for oligomerization of S1R prior to pridopidine activation, which could induce a conformational change. The oligomerization of S1R could render the protein less amenable to degradation, therefore increasing its half-life. S1R conformational change, induced by pridopidine, could favor oligomerization or increase the resistance of the oligomers to degradation. Pridopidine restores the colocalization of S1R and BiP (FIGS. 15A-15B), which is consistent with the reduction in ER stress.

Pridopidine increases the fraction of mHtt present in insoluble aggregates, in a S1R-mediated mechanism (FIG. 16A). Pridopidine does not affect the number of cells showing large mHtt aggregates (FIG. 16B) indicating that it does not affect the probability of initiation of large aggregate formation by random seeding events, but rather causes an increased sequestration of mHtt to the insoluble aggregates in each cell.

Loss of function mutations in the S1R are directly linked to a familial form of ALS and to distal hereditary motor neuropathies (dHMN). Pridopidine shows S1R-mediated neuroprotective effects in models of ALS, PD and AD. As ER stress is a central feature in these diseases, the neuroprotective effects of pridopidine may be through S1R activation and reduction of ER stress.

REFERENCES

Bernard-Marissal, Nathalie, Jean-Jacques Medard, Hamid Azzedine, and Roman Chrast. 2015. "Dysfunction in Endoplasmic Reticulum-Mitochondria Crosstalk Underlies SIGMAR1 Loss of Function Mediated Motor Neuron Degeneration." Brain: A Journal of Neurology 138 (Pt 4): 875-90. https://doi.org/10.1093/brain/awv008.

Chambers, Stuart M, Christopher A Fasano, Eirini P Papapetrou, Mark Tomishima, Michel Sadelain, and Lorenz Studer. 2009. "Highly Efficient Neural Conversion of Human ES and IPS Cells by Dual Inhibition of SMAD Signaling." Nature Biotechnology 27 (3): 275-80. https://doi.org/10.1038/nbt.1529.

Cherubini, Marta, Laura Lopez-Molina, and Silvia Gines. 2020. "Mitochondrial Fission in Huntington's Disease Mouse Striatum Disrupts ER-Mitochondria Contacts Leading to Disturbances in Ca2+ Efflux and Reactive Oxygen Species (ROS) Homeostasis." Neurobiology of Disease. https://doi.org/10.1016/j.nbd.2020.104741.

Delli Carri, Alessia, Marco Onorati, Valentina Castiglioni, Andrea Faedo, Stefano Camnasio, Mauro Toselli, Gerardo Biella, and Elena Cattaneo. 2013. "Human Pluripotent Stem Cell Differentiation into Authentic Striatal Projection Neurons." Stem Cell Reviews and Reports 9 (4): 461-74. https://doi.org/10.1007/s12015-013-9441-8.

Delprat, Benjamin, Lucie Crouzier, Tsung Ping Su, and Tangui Maurice. 2020. "At the Crossing of ER Stress and MAMs: A Key Role of Sigma-1 Receptor?" In Advances in Experimental Medicine and Biology. https://doi.org/10.1007/978-3-030-12457-1_28.

Dickinson, Bryan C, Vivian S Lin, and Christopher J Chang. 2013. "Preparation and Use of MitoPY1 for Imaging Hydrogen Peroxide in Mitochondria of Live Cells." Nature Protocols 8 (6): 1249-59. https://doi.org/10.1038/nprot.2013.064.

Eddings, Chelsy R., Nicolas Arbez, Sergey Akimov, Michal Geva, Michael R. Hayden, and Christopher A. Ross. 2019. "Pridopidine Protects Neurons from Mutant-Huntingtin Toxicity via the Sigma-1 Receptor." Neurobiology of Disease. https://doi.org/10.1016/j.nbd.2019.05.009.

Ehrnhoefer, Dagmar E, Amber L Southwell, Meenalochani Sivasubramanian, Xiaofan Qiu, Erika B Villanueva, Yuanyun Xie, Sabine Waltl, et al. 2018. "HACE1 Is Essential for Astrocyte Mitochondrial Function and Influences Huntington Disease Phenotypes in Vivo." Human Molecular Genetics 27 (2): 239-53. https://doi.org/10.1093/hmg/ddx394.

Erpapazoglou, Zoi, François Mouton-Liger, and Olga Corti. 2017. "From Dysfunctional Endoplasmic Reticulum-Mitochondria Coupling to Neurodegeneration." Neurochemistry International. https://doi.org/10.1016/j.neuint.2017.03.021.

Ferreira, I. Luísa, Catarina Carmo, Luana Naia, Sandra I. Mota, and A. Cristina Rego. 2018. "Assessing Mitochondrial Function in In Vitro and Ex Vivo Models of Huntington's Disease." In Huntington's Disease, Methods in Molecular Biology, edited by Sophie V. Precious and et al., 415-42. Springer. https://doi.org/10.1007/978-1-4939-7825-0_19.

Francardo, Veronica, Michal Geva, Francesco Bez, Quentin Denis, Lilach Steiner, Michael R Hayden, and M Angela Cenci. 2019. "Pridopidine Induces Functional Neurorestoration Via the Sigma-1 Receptor in a Mouse Model of Parkinson's Disease." Neurotherapeutics, no. 16: 465-479. https://doi.org/10.1007/s13311-018-00699-9.

Fu, Zhong-Xiao, Xiao Tan, Huaqiang Fang, Pak-Ming Lau, Xianhua Wang, Heping Cheng, and Guo-Qiang Bi. 2017. "Dendritic Mitoflash as a Putative Signal for Stabilizing Long-Term Synaptic Plasticity." Nature Communications 8 (1): 31. https://doi.org/10.1038/s41467-017-00043-3.

Hayashi, Teruo, and Tsung Ping Su. 2007. "Sigma-1 Receptor Chaperones at the ER-Mitochondrion Interface Regulate Ca2+ Signaling and Cell Survival." Cell 131 (3): 596-610. https://doi.org/10.1016/j.cell.2007.08.036.

Herbert, Alex D., Antony M. Carr, and Eva Hoffmann. 2014. "FindFoci: A Focus Detection Algorithm with Automated Parameter Training That Closely Matches Human Assignments, Reduces Human Inconsistencies and Increases Speed of Analysis." Edited by Michael Lichten. PLoS ONE 9 (12): e114749. https://doi.org/10.1371/journal.pone.0114749.

Ionescu, Ariel, Tal Gradus, Topaz Altman, Roy Maimon, Noi Saraf Avraham, Michal Geva, Michael Hayden, and Eran Perlson. 2019. "Targeting the Sigma-1 Receptor via Pridopidine Ameliorates Central Features of ALS Pathology in a SOD1G93A Model." Cell Death & Disease 10 (3): 210. https://doi.org/10.1038/s41419-019-1451-2.

Leitman, Julia, F. Ulrich Hard, and Gerardo Z. Lederkremer. 2013. "Soluble Forms of PolyQ-Expanded Huntingtin Rather than Large Aggregates Cause Endoplasmic Reticulum Stress." Nature Communications. https://doi.org/10.1038/ncomms3753.

Lewis, Tommy L., Seok-Kyu Kwon, Annie Lee, Reuben Shaw, and Franck Polleux. 2018. "MFF-Dependent Mitochondrial Fission Regulates Presynaptic Release and Axon Branching by Limiting Axonal Mitochondria Size." Nature Communications 9 (1): 5008. https://doi.org/10.1038/s41467-018-07416-2.

Naia, Luana, and Ana Cristina Rego. 2018. "Isolation and Maintenance of Striatal Neurons." Bio-Protocol 8 (8). https://doi.org/10.21769/BioProtoc.2823.

Nicoleau, Camille, Christine Varela, Caroline Bonnefond, Yves Maury, Aurore Bugi, Laetitia Aubry, Pedro Viegas, Fany Bourgois-Rocha, Marc Peschanski, and Anselme L Perrier. 2013. "Embryonic Stem Cells Neural Differentiation Qualifies the Role of Wnt/β-Catenin Signals in Human Telencephalic Specification and Regionalization." STEM CELLS 31 (9): 1763-74. https://doi.org/10.1002/stem.1462.

Niescier, Robert F., Kido Hong, Dongkeun Park, and Kyung-Tai Min. 2018. "MCU Interacts with Miro1 to Modulate Mitochondrial Functions in Neurons." The Journal of Neuroscience 38 (20): 4666-77. https://doi.org/10.1523/JNEUROSCI.0504-18.2018.

Onofre, Isabel, Nuno Mendonça, Sara Lopes, Rui Nobre, Joana Barbosa de Melo, Isabel Marques Carreira, Cristina Januário, António Freire Gonçalves, and Luis Pereira de Almeida. 2016. "Fibroblasts of Machado Joseph Disease Patients Reveal Autophagy Impairment." Scientific Reports 6 (1): 28220. https://doi.org/10.1038/srep28220.

Pal, Arindam, Dominique Fontanilla, Anupama Gopalakrishnan, Young-Kee Chae, John L. Markley, and Arnold E. Ruoho. 2012. "The Sigma-1 Receptor Protects against Cellular Oxidative Stress and Activates Antioxidant Response Elements." European Journal of Pharmacology 682 (1-3): 12-20. https://doi.org/10.1016/j.ejphar.2012.01.030.

Park, In-Hyun, Natasha Arora, Hongguang Huo, Nimet Maherali, Tim Ahfeldt, Akiko Shimamura, M. William Lensch, Chad Cowan, Konrad Hochedlinger, and George Q. Daley. 2008. "Disease-Specific Induced Pluripotent Stem Cells." Cell 134 (5): 877-86. https://doi.org/10.1016/j.cell.2008.07.041.

Raamsdonk, Jeremy M Van, Jacqueline Pearson, Elizabeth J Slow, Sazzad M Hossain, Blair R Leavitt, and Michael R Hayden. 2005. "Cognitive Dysfunction Precedes Neuropathology and Motor Abnormalities in the YAC128 Mouse Model of Huntington's Disease." The Journal of Neuroscience: The Official Journal of the Society for Neuroscience 25 (16): 4169-80. https://doi.org/10.1523/JNEUROSCI.0590-05.2005.

Ribeiro, Marcio, Tatiana R Rosenstock, Ana M. Oliveira, Catarina R Oliveira, and A Cristina Rego. 2014. "Insulin and IGF-1 Improve Mitochondrial Function in a PI-3K/Akt-Dependent Manner and Reduce Mitochondrial Generation of Reactive Oxygen Species in Huntington's Disease Knock-in Striatal Cells." Free Radical Biology and Medicine 74 (September): 129-44. https://doi.org/10.1016/j.freeradbiomed.2014.06.023.

Rietdorf, J, and Seitz A. 2008. "Multi Kymograph." 2008.

Rogers, George W, Martin D Brand, Susanna Petrosyan, Deepthi Ashok, Alvaro A Elorza, David A Ferrick, and Anne N Murphy. 2011. "High Throughput Microplate Respiratory Measurements Using Minimal Quantities of Isolated Mitochondria." PloS One 6 (7): e21746. https://doi.org/10.1371/journal.pone.0021746.

Rossi, Alice, Paola Pizzo, and Riccardo Filadi. 2019. "Calcium, Mitochondria and Cell Metabolism: A Functional Triangle in Bioenergetics." Biochimica et Biophysica Acta—Molecular Cell Research. https://doi.org/10.1016/j.bbamcr.2018.10.016.

Ryskamp, Daniel, Lili Wu, Jun Wu, Dabin Kim, Michal Geva, Gerhard Rammes, and Ilya Hayden, Michael-Bezprozvanny. 2018. "Pridopidine Stabilizes Mushroom Spines in Mouse Models of Alzheimer's Disease by Acting on the Sigma-1 Receptor." Neurobiology of Disease 124 (December 2018): 489-504. https://doi.org/10.1016/j.nbd.2018.12.022.

Smith-Dijak, Amy I., Wissam B. Nassrallah, Lily Y. J. Zhang, Michal Geva, Michael R. Hayden, and Lynn A. Raymond. 2019. "Impairment and Restoration of Homeostatic Plasticity in Cultured Cortical Neurons from a Mouse Model of Huntington Disease." Frontiers in Cellular Neuroscience. https://doi.org/10.3389/fncel.2019.00209.

Smith-dijak, Amy I, Wissam Nassrallah, Lily Zhang, Michal Geva, Michael Hayden, and Lynn Raymond. n.d. "Impairment and Restoration of Homeostatic Plasticity in Cultured Cortical Neurons from a Mouse Model of Huntington Disease."

Trettel, Flavia, Dorotea Rigamonti, Paige Hilditch-Maguire, Vanessa C. Wheeler, Alan H. Sharp, Francesca Persichetti, Elena Cattaneo, and Marcy E. MacDonald. 2000. "Dominant Phenotypes Produced by the HD Mutation in STHdh(Q111) Striatal Cells." Human Molecular Genetics. https://doi.org/10.1093/hmg/9.19.2799.

Vallese, Francesca, Lucia Barazzuol, Lorenzo Maso, Marisa Brini, and Tito Cali. 2020. "ER-Mitochondria Calcium Transfer, Organelle Contacts and Neurodegenerative Diseases." In Advances in Experimental Medicine and Biology. https://doi.org/10.1007/978-3-030-12457-1_29.

Veeresh, Pabbala, Harpreet Kaur, Deepaneeta Sarmah, Leela Mounica, Geetesh Verma, Vignesh Kotian, Radhika Kesharwani, et al. 2019. "Endoplasmic Reticulum-Mitochondria Crosstalk: From Junction to Function across Neurological Disorders." Annals of the New York Academy of Sciences. https://doi.org/10.1111/nyas.14212.

---

What is claimed is:

1. A method of treating, suppressing, or inhibiting mitochondrial myopathy in a subject by administering to the subject pridopidine or a pharmaceutically acceptable salt thereof, and the mitochondrial myopathy is selected from the group consisting of Mitochondrial DNA depletion syndrome (MDS), Neuropathy, Wolfram Syndrome, Chronic Progressive External Ophthalmoplegia (C/PEO), Dominant Optical Atrophy (DOA), or a combination thereof, and wherein the Neuropathy is not Optic neuropathy.

2. The method of claim 1, wherein said pridopidine is in its neutral/base form or a pharmaceutically acceptable salt form.

3. The method of claim 1, wherein said pridopidine is pridopidine hydrochloride.

4. The method of claim 1, wherein said composition is administered in the form of an inhalable powder, an injectable, a liquid, a gel, a solid, a capsule, eye drops or a tablet.

5. The method of claim 1, wherein said composition is administered in a multiparticulate delivery vehicle comprising pellets, beads, granules, microparticles, nanoparticles, or a combination thereof.

6. The method of claim 1, wherein said composition is administered once, twice, or three times a day.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: XBP1

<400> SEQUENCE: 1
tgctgagtcc gcagcaggtg                                              20

<210> SEQ ID NO 2
<211> LENGTH: 20
<212> TYPE: DNA
<213> ORGANISM: Artificial Sequence
<220> FEATURE:
<223> OTHER INFORMATION: XBP1

<400> SEQUENCE: 2
gctggcaggc tctggggaag                                              20

<210> SEQ ID NO 3
<211> LENGTH: 20
<212> TYPE: DNA
<213> ORGANISM: Artificial Sequence
<220> FEATURE:
<223> OTHER INFORMATION: S1R

<400> SEQUENCE: 3
tgggctgaga tctcggatac                                              20

<210> SEQ ID NO 4
<211> LENGTH: 20
<212> TYPE: DNA
<213> ORGANISM: Artificial Sequence
<220> FEATURE:
<223> OTHER INFORMATION: S1R

<400> SEQUENCE: 4
aggcccgtgt actaccgtct                                              20

<210> SEQ ID NO 5
<211> LENGTH: 20
<212> TYPE: DNA
<213> ORGANISM: Artificial Sequence
<220> FEATURE:
<223> OTHER INFORMATION: GAPDH

<400> SEQUENCE: 5
ccacatcgct cagacaccat                                              20
```

-continued

```
<210> SEQ ID NO 6
<211> LENGTH: 27
<212> TYPE: DNA
<213> ORGANISM: Artificial Sequence
<220> FEATURE:
<223> OTHER INFORMATION: GAPDH

<400> SEQUENCE: 6
caacaatatc cactttacca gagttaa                                                      27
```